United States Patent
Barber et al.

(10) Patent No.: US 6,531,307 B1
(45) Date of Patent: Mar. 11, 2003

(54) ADENOVIRAL VECTORS ENCODING A CYTOKINE AND A CONDITIONALLY LETHAL GENE

(75) Inventors: Jack R. Barber, San Diego, CA (US); Harry E. Gruber, San Diego, CA (US); Douglas J. Jolly, Leucadia, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 08/455,014

(22) Filed: May 31, 1995

Related U.S. Application Data

(62) Division of application No. 08/155,944, filed on Nov. 18, 1993, now abandoned, which is a continuation-in-part of application No. 08/139,994, filed on Oct. 20, 1993, now abandoned, which is a continuation of application No. 07/965,084, filed on Oct. 22, 1992, now abandoned.

(51) Int. Cl.[7] .................... C12N 15/861; C12N 15/00; A61K 48/00; C07H 21/04
(52) U.S. Cl. .................. 435/235.1; 435/320.1; 435/194; 424/93.2; 536/23.1; 514/44
(58) Field of Search .............. 424/93.21; 435/320.1, 435/194, 235.1; 514/44; 536/23.1

(56) References Cited

U.S. PATENT DOCUMENTS

| | | |
|---|---|---|
| 4,603,112 A | 7/1986 | Paoletti et al. |
| 4,663,281 A | 5/1987 | Gillies et al. ............ 435/69.1 |
| 4,677,064 A | 6/1987 | Mark et al. ............ 435/69.1 |
| 4,738,922 A | 4/1988 | Haseltine et al. ........ 435/69.3 |
| 4,752,565 A | 6/1988 | Folks et al. .............. 435/5 |
| 4,769,330 A | 9/1988 | Paoletti et al. |
| 5,026,635 A | 6/1991 | Ferguson et al. .......... 435/5 |
| 5,081,021 A | 1/1992 | Mizuno et al. ........... 435/69.5 |
| 5,091,309 A | 2/1992 | Schlesinger et al. |
| 5,246,924 A | 9/1993 | Fox et al. ................ 514/50 |
| 5,304,489 A | 4/1994 | Rosen ................... 435/320.1 |
| 5,306,631 A | 4/1994 | Harrison et al. ......... 435/172.3 |
| 5,324,655 A | 6/1994 | Kriegler et al. ........... 435/357 |
| 5,399,346 A | 3/1995 | Anderson et al. ........ 424/93.21 |
| 5,529,774 A | 6/1996 | Barba et al. ............. 424/93.21 |
| 5,604,293 A | 2/1997 | Fiddes et al. ............. 530/399 |
| 5,631,236 A * | 5/1997 | Woo et al. |
| 5,635,399 A | 6/1997 | Kriegler et al. ......... 435/320.1 |
| 5,674,486 A * | 10/1997 | Sobol et al. ............ 424/93.21 |
| 5,691,177 A | 11/1997 | Gruber et al. |
| 6,013,638 A * | 1/2000 | Crystal et al. |

FOREIGN PATENT DOCUMENTS

| | | |
|---|---|---|
| AU | B 19201/88 | 1/1989 |
| EP | 0 288 163 A2 | 10/1988 |
| EP | 0 334 301 A1 | 9/1989 |
| EP | 0 415 731 A2 | 3/1991 |
| EP | 440 219 A1 | 8/1991 |
| EP | 0 476 953 A2 | 3/1992 |
| FR | 2 606 030 | 6/1988 |
| FR | 0 273 782 A1 | 7/1988 |
| WO | WO 85/05629 | 12/1985 |
| WO | WO 86/00930 | 2/1986 |
| WO | WO 88/00971 * | 2/1988 |
| WO | WO 89/01972 | 3/1989 |
| WO | WO 89/01973 | 3/1989 |
| WO | WO 90/07936 | 7/1990 |
| WO | WO 90/11092 | 10/1990 |
| WO | WO 91/02805 | 3/1991 |
| WO | WO 92/15693 | 9/1992 |
| WO | WO 93/02556 * | 2/1993 |
| WO | WO 93/04167 | 3/1993 |
| WO | WO 93/07906 | 4/1993 |
| WO | WO 93/08844 | 5/1993 |
| WO | WO 93/10218 * | 5/1993 |
| WO | WO 93/21959 * | 11/1993 |
| WO | WO 94/21792 | 9/1994 |

OTHER PUBLICATIONS

Berkner (1988) Development of adenovirus vectors for the expression of heterologous genes. Bio Techniques 6:616–629, 1988.*

Field et al., "Isolation and Characterization of Acyclovir-resistant Mutants of Herpes Simplex Virus," *Journal of General Virology* 49: 115–124, 1980.

Berkner, "Development of Adenovirus Vectors for the Expression of Heterologous Genes," *BioTechniques* 6(7): 616–629, 1988.

Rosenfeld et al., "Adenovirus–Mediated Transfer of a Recombinant α1–Antitrypsin Gene to the Lung Epithelium in Vivo," *Science* 252: 431–434, 1991.

Toohey et al., "Multiple Hormone–Inducible Enhancers as Mediators of Differential Transcription," *Molecular and Cellular Biology* 6(12): 4526–4538, 1986.

Schrewe et al., "Cloning of the Complete Gene for Carcinoembryonic Antigen: Analysis of Its Promoter Indicates a Region Conveying Cell Type–Specific Expression," *Molecular and Cellular Biology* 10(6):2738–2748, 1990.

Doppler et al., "Prolactin and glucocorticoid hormones synergistically induce expression of transfected rat β–casein gene promoter constructs in a mammary epithelial cell line," *Proc. Natl. Acad. Sci. USA* 86: 104–108, 1989.

(List continued on next page.)

*Primary Examiner*—David Guzo
*Assistant Examiner*—Gerald G. Leffers, Jr.
(74) *Attorney, Agent, or Firm*—Donald Pochopien; Alisa A. Harbin; Robert P. Blackburn

(57) ABSTRACT

The present invention provides recombinant viral vectors carrying a vector construct which directs the expression of a gene product (eg. HSVTK) that activates a compound with little or no cytotoxicity into a toxic product. Also provided are methods of destroying or inhibiting pathogenic agents in a warm blooded animal, comprising the step of administering to the animal a viral vector such as that described above, in order to inhibit or destroy the pathogenic agent.

23 Claims, 25 Drawing Sheets

OTHER PUBLICATIONS

Mullen et al., "Transfer of the bacterial gene for cytosine deaminase to mammalian cell confers lethal sensitivity to 5–fluorocytosine: A negative selection system," *Proc. Natl. Acad. Sci. USA* 89: 33–37, 1992.

Searle et al., "The potential of carboxypeptidase $G_2$–antibody conjugates as anti–tumour agents. I. Preparation of antihuman chorionic gonadotropin–carboxypeptidase $G_2$ and cytotoxicity of the conjugate against JAR choriocarcinoma cells in vitro," *British Journal of Cancer* 53: 377–384, 1986.

Hatzoglou et al., "Hormonal Regulation of Chimeric Genes Containing the Phosphoenolpyruvate Carboxykinase Promoter Regulatory Region in Hepatoma Cells Infected by Murine Retroviruses," *Journal of Biological Chemistry* 263(33): 17798–17808, 1988.

Deng et al., "The Mouse Thymidylate Synthase Promoter: Essential Elements Are in Close Proximity to the Transcriptional Initiation Sites," *Molecular and Cellular Biology* 9(9): 4079–4082, 1989.

Rosen et al., "Intragenic cis–acting art gene–responsive sequences of the human immunodeficiency virus," *Proc. Natl. Acad. Sci. USA* 85: 2071–2075, 1988.

Sabin and Boulger, "History o Sabin attenuated poliovirus oral live vaccine strains," *Journal of Biological Standardization* 1: 115–118, 1973.

Irvin, "Purification and Partial Characterization of the Antiviral Protein from *Phytolacca americana* Which Inhibits Eukaryotic Protein Synthesis," *Archives of Biochemistry and Biophysics* 169: 522–528, 1975.

Yap and Ada, "Transfer of specific sytitoxic T lymphocytes protects mice inoculated with influenza virus," *Nature* 273: 238–239, 1978.

Mulligan et al., "Synthesis of rabbit β–globulin in cultured monkey kidney cells following infection with SV40 β–globulin recombinant genome," *Nature* 277: 108–114, 1979.

Irvin et al., "Purification and Propeties of a Second Antiviral Protein from *Phytolacca americana* which inactivates Eukaryotic Ribosomes," *Archives of Biochemistry and Biophysics* 200(2): 418–425, 1980.

Stirpe et al., "Gelonin, a New Inhibitor of Protein Synthesis, Nontoxic to Intact Cells," *Journal of Biological Chemistry* 255(14): 6947–6953, 1980.

Parnes et al., "Mouse $β_2$–microglobulin cDNA clones: A screening procedure for cDNA clones corresponding to rare mRNAs," *Proc. Natl. Acad. Sci. USA* 78(4): 2253–2257, 1981.

Barbieri et al., "Purification and partial characterization of another form of the antiviral protein from the seeds of *Phytolacca americana* L. (pokeweed)," *Biochem. J.* 203: 55–59, 1982.

McMichael et al., "Cytotoxic T–Cell Immunity to Influenza," *New Eng. J. Med.* 309(1): 13–17, 1983.

Panicali et al., "Construction of live vaccines by using genetically engineered poxviruses: Biological activity of recombinant vaccinia virus expressing influenza virus hemagglutinin," *Proc. Natl. Acad. Sci. USA* 80: 5364–5368, 1983.

Ball et al., "Monoclonal Antibodies to Myeloid Differentiation Antigens: In Vivo Studies of Three Patients With Acute Myologenous Leukemia," *Blood* 62(6): 1203–1210, 1983.

Mekalanos et al., "Cholera toxin genes: nucleotide sequence, deletion analysis and vaccine development," *Nature* 306: 551–557, 1983.

Dubensky et al., "Direct transfection of viral and plasmid DNA into the liver or spleen of mice," *Proc. Natl. Acad. Sci. USA* 81: 7529–7533, 1984.

Stanton et al., "Nucleotide sequence comparison of normal and translocated murine c–myc genes," *Nature* 310: 423–425, 1984.

Eglitis et al., "Gene Expression in Mice After High Efficiency Retroviral–Mediated Gene Transfer," *Science* 230: 1395–1398, 1985.

Keller et al., "Expression of a foreign gene in myeloid and lymphoid cells derived from multipotent haematopoietic precursors," *Nature* 318: 149–154, 1985.

Coussens et al., "Tyrosine Kinase Receptor with Extensive Homology to EGF Receptor Shares Chromosomal Location with neu Oncogene," *Science* 230: 1138–1139, 1985.

Lamb, et al., "Nucleotide sequence of cloned cDNA coding for preproricin," *Eur. J. Biochem* 148: 265–270, 1985.

Tweten et al., "Diptheria Toxin—Effect of substituting aspartic acid for glutamic acid 148 on ADP ribosyltransferase activity," *J. Biol. Chem.* 260: 10392–10394, 1985.

Rosenberg et al., "Observations on the systemic administration of autologous lymphokine–activated killer cells and recombinant interleukin–2 to patients with metastatic cancer," *New Eng. J. Med.* 313(23): 1485–1492, 1985.

Furman et al., "Phosphorylation of 3'–azido–3'–deoxythymidine and selective interaction of the 5'–triphosphate with human immunodeficiency virus reverse transcriptase," *Proc. Natl. Acad. Sci. USA* 83: 8333–8337, 1986.

Lifson, et al., "AIDS Retrovirus Induced Cytopathology: Giant Cell Formation and Involvement of CD4 Antigen," *Science* 232: 1123–1127, 1986.

Lifson et al., "Role of envelope glycoprotein carbohydrate in human immunodeficiency virus (HIV) infectivity and virus–induced cell fusion," *Journal of Experimental Medicine* 164: 2101–2106, 1986.

McDougal et al., "Binding of HTLV–III/LAV to T4+ T Cells by a Complex of the 110K Viral Protein and T4 Molecule," *Science* 231: 382–385, 1986.

Pert et al., "Octapeptides deduced from the neuropeptide receptor–like pattern of antigen T4 in brain potently inhibit human immunodeficiency virus receptor binding and T–cell infectivity," *Proc. Natl. Acad. Sci. USA* 83: 9254–9258, 1986.

To et al., "Inhibition of Retroviral Replication by Anti–Sence RNA," *Molecular and Cellular Biology* 6: 4758–4762, 1986.

Goodbourn et al., "The Human β–Interferon Gene Enhancer Is under Negative Control," *Cell* 45: 601–610, 1986.

Armentano et al., "Effect of Internal Viral Sequences on the Utility of Retroviral Vectors," *Journal of Virology* 61(5); 1647–1650, 1987.

Krissansen et al., "Chromosomal locations of the gene coding for the CD3 (T3) γ subunit of the human and mouse CD3/T–cell antigen receptor complexes," *Immunogenetics* 26: 258–266, 1987.

Ledley, "Somatic gene therapy for human disease: Background and prospects. Part I," *Journal of Pediatrics* 110(1): 1–8, 1987.

Wang and Huang, "pH–sensitive immunoliposomes mediate target–cell–specific delivery and controlled expression of a foreign gene in mouse," *Proc. Natl. Acad. Sci. USA 84:* 7851–7855, 1987.

Jackson et al., "Nucleotide sequence analysis of the structural genes for Shiga–like toxin I encoded by bacteriophage 900J from *Escherichia coli,*" *Microbial Pathogenesis 2:* 147–153, 1987.

Maher III and Dolnick, "Specific Hybridization Arrest of Dihydrofolate Reductase mRNA in Vitro Using Anti–Sense RNA or Anti–sense Oligonucleotides," *Archives of Biochemistry and Biophysics 253*(1): 214–220, 1987.

Carroll and Collier, "Active Site of *Pseudomonas aeruginosa* Exotoxin A," *Journal of Biological Chemistry 262*(18): 8707–8711, 1987.

Bzik et al., "Molecular cloning and sequence analysis of the *Plasmodium falciparum* dihydrofolate reductase–thymidylate synthase gene," *Proc. Natl. Acad. Sci. USA 84:* 8360–8364, 1987.

Calderwood et al., "Nucleotide sequence of the Shiga–like toxin genes of *Escherichia coli,*" *Proc. Natl. Acad. Sci. USA 84:* 4364–4368, 1987.

Wallner et al., "Primary structure of lymphocyte function–associated antigen 3 (LFA–3): The Ligand of the T Lymphocyte CD2 Glycoprotein," *Journal of Experimental Medicine 166:* 923–932, 1987.

Tal et al., "Human HER2 (neu) Promoter: Evidence for Multiple Mechanisms for Transcriptional Initiation," in *Molecular and Cellular Biology 7*(7): 2597–2601, 1987.

Dillman, "Antibody Therapy," *Principles of Cancer Biotherapy,* Chapter 13: 395–432, 1987.

Mendelson et al., "Expression and Rescue of a Nonselected Marker from an Integrated AAV Vector," *Virology 166:* 154–165, 1988.

Simmons et al., "ICAM, an adhesion ligand of LFA–1, is homologous to the neural cell adhesion molecule NCAM," *Nature 331:* 624–627, 1988.

Bodner et al., "The Pituitary–Specific Transcription Factor GHF–1 Is a Homeobox–Containing Protein," *Cell 55:* 505–518, 1988.

Ingraham, et al., "A Tissue–Specific Transcription Factor Containing a Homeodomain Specifies a Pituitary Phenotype," *Cell 55:* 519–529, 1988.

Anderson et al., "A conserved sequence in the T–cell receptor β–chain promoter region," *Proc. Natl. Acad. Sci. USA 85:* 3551–3554, 1988.

Ohlsson et al., "A beta–cell–specific protein binds to the two major regulatory sequences of the insulin gene enhancer," *Proc. Natl. Acad. Sci. USA 85:* 4228–4231, 1988.

Evans et al., "An engineered poliovirus chimaera elicits broadly reactive HIV–1 neutralizing antibodies," *Nature 339:* 385–388, 1989.

Felgner et al., "Lipfection: A highly efficient, lipid–mediated DNA–transfection procedure," *Proc. Natl. Acad. Sci. USA 84:* 7413–7417, 1987.

Fisher–Hoch et al., "Protection of rhesus monkeys from fatal Lassa fever by vaccination with a recombinant vaccinia virus containing the Lassa virus glycoprotein gene," *Proc. Natl. Acad. Sci USA 86:* 317–321, 1989.

Moss and Flexner, "Vaccinia Virus Expression Vectors," *Annals of the N.Y. Academy of Sciences 569:* 86–103, 1989.

Kit, "Recombinant–derived modified–live herpesvirus vaccines," *Adv. Exp. Med. Biol. 251:* 219–236, 1989.

Luytjes et al., "Amplification, Expression, and Packaging of a Foreign Gene by Influenza Virus," *Cell 59:* 1107–1113, 1989.

Samulski et al., "Helper–Free Stocks of Recombinant Adeno–Associated Viruses: Normal Integration Does Not Require Viral Gene Expression," *Journal of Virology 63*(9): 3822–3828, 1989.

Wu et al., "Targeting Genes: Delivery and Persistent Expression of a Foreign Gene Driven by Mammalian Regulatory Elements in Vivo," *Journal of Biological Chemistry 264*(29): 16985–16987, 1989.

Xiong et al., "Sindbis Virus: An Efficient, Broad Host Range Vector for Gene Expression in Animal Cells," *Science 243:* 1188–1191, 1989.

Sanchez and Holmgren, "Recombinant system for overexpression of cholera toxin B subunit in *Vibrio cholerae* as a basis for vaccine development," *Proc. Natl. Acad. Sci. USA 86:* 481–485, 1989.

Swift et al., "Differential requirements for cell–specific elastase I enhancer domains in transfected cells and transgenic mice," *Genes & Development 3:* 687–696, 1989.

Benvenisty et al., "Separate cis–regulatory elements confer expression of phophoenolpyruvate carboxykinase (GTP) gene in different cell lines," *Proc. Natl. Acad. Sci. USA 86:* 1118–1122, 1989.

Fan and Maniatis, "Two different virus–inducible elements are required for human β–interferon gene regulation," *EMBO Journal 8*(1): 101–110, 1989.

Winoto and Baltimore, "A novel, inducible and T cell–specific enhancer located at the 3' end of the T cell receptor α locus," *EMBO Journal 8*(3): 729–733, 1989.

Camper and Tilghman, "Postnatal expression of the α–fetoprotein gene is enhancer independent," *Genes & Development 3:* 537–546, 1989.

Karlsson et al., "Individual Protein–Binding Domains of the Insulin Gene Enhancer Positively Activate β–Cell–Specific Transcription," *Molecular and Cellular Biology 9:* 823–827, 1989.

Baldwin and Burden, "Muscle–specific gene expression controlled by a regulatory element lacking a MyoD1–binding site," *Nature 341:* 716–720, 1989.

McDonnell et al., "Reconstitution of the Vitamin D–Responsive Osteocalcin Transcription Unit in *Saccharomyces cerevisiae,*" *Molecular and Cellular Biology 9:* 3517–3523, 1989.

van Assendelft et al., "The β–Globin Dominant Control Region Activates Homologous and Heterologous Promoters in a Tissue–Specific Manner," *Cell 56:* 969–977, 1989.

Feuerman et al., "Tissue–Specific Transcription of the Mouse α–Fetoprotein Gene Promoter Is Dependent on HFN–1," *Molecular and Cellular Biology 9:* 4204–4212, 1989.

Vaulont et al., "Analysis by Cell–Free Transcription of the Liver–Specific Pyruvate Kinase Gene Promoter," *Molecular and Cellular Biology,* 9: 4409–4415, 1989.

Kerner et al., "Sequence elements in the human osteocalcin gene confer basal activation and inducible response to hormonal vitamin $D_3$," *Proc. Natl. Acad. Sci. USA 86:* 4455–4459, 1989.

Gross and Merrill, "Tymidine kinase synthesis is represssed in nonreplicating muscle cells by a translational mechanism that does not affect the polysomal distribution of thymidine kinase mRNA," *Proc. Natl. Acad. Sci. USA 86:* 4987–4991, 1989.

Tussey and Felder, "Tissue–specific genetic variation in the level of mouse alcohol dehydrogenase is controlled transcriptionally in kidney and posttranscriptionally in liver," *Proc. Natl. Acad. Sci. USA 86:* 5903–5907, 1989.

Forrester et al., "Molecular analysis of the human β–globin locus activation region," *Proc. Natl. Acad. Sci. USA 86:* 5439–5443, 1989.

Flexner et al., "Attenuation and immunogenicity in primates of vaccinia virus recombinants expressing human interleukin–2," *Vaccine 8:* 17–21, 1990.

Collins et al., "Primary Amino Acid Sequence of α–Trichosanthin and Molecular Models for Abrin A–chain and α–Trichosanthin," *Journal of Biological Chemistry* 265(15): 8665–8669, 1990.

Kerr et al., "Antibody–penicillin–V–amidase conjugates kill antigen–positive tumor cells when combined with doxorubicin phenoxyacetamide," *Cancer Immunol. Immunother. 31:* 202–206, 1990.

Markose et al., "Vitamin D–mediated modifications in protein–DNA interactions at two promoter elements of the osteocalcin gene," *Proc. Natl. Acad. Sci. USA 87:* 1701–1705, 1990.

Acsadi et al., "Human dystrophin expression in mdx mice after intramuscular injection of DNA constructs," *Nature 352:* 815–818, 1991.

Williams et al., "Introduction of foreign genes into tissues of living mice by DNA–coated microprojectiles," *Proc. Natl. Acad. Sci. USA 88:* 2726–2730, 1991.

Wood et al., "Preproabrin: genomic cloning, characterisation and the expression of the A–chain in *Escherichia coli,*" *European Journal of Biochemistry 198:* 723–732, 1991.

Evensen et al., "Direct Molecular Cloning and Expression of Two Distinct Abrin A–chains," *Journal of Biological Chemistry* 266(11): 6848–6852, 1991.

Curiel et al., "High–Efficiency Gene Transfer Mediated by Adenovirus Coupled to DNA–Polylysine Complexes," *Human Gene Therapy 3:* 147–154, 1992.

Rabinovitz, "The pleiotypic response to amino acid deprivation is the result of interactions between components of the glycolysis and protein synthesis," *FEBS 302*(2): 113–116, 1992.

Vrudhula et al., "Prodrugs of Doxorubicin and Melphalan and Their Activation by a Monoclonal Antibody–Penicillin–G Amidase Conjugate," *J. Med. Chem. 36:* 919–923, 1993.

Adam et al., "Identification of a Signal in a Murine Retrovirus That is Sufficient for Packaging of Nonretroviral RNA into Virions," *J. Virology,* 62(10): 3802–3806 (Oct., 1988).

Anderson, F.W., "Human Gene Therapy," *Science,* 256:808–813 (May 8, 1992).

Baltimore, "Intracellular Immunization," *Nature,* 335:395–396 (1988).

Cepko et al., "Construction and Applications of a Highly Transmissible Murine Retorvirus Shuttle Vector," *Cell,* 37:1053–1062, (Jul., 1984).

Cone et al., "Regulated Expression of a Complete Human β–Globin Gene Encoded by a Transmissible Retrovirus Vector," *Mol. & Cell. Biol.,* 7(2):887–897 (Feb., 1987).

Cournoyer et al., "Gene Therapy of the Immune System," *Ann. Rev. Immunol.,* 11:297–329 (1993).

Danos et al., "Safe and Efficient Generation of Recombinant Retroviruses with Amphotropic and Ecotropic Host Ranges," *Proc. Nat'l. Acad. Sci., USA,*85:6460–6464, (Sep., 1988).

Dayton et al., "The Trans–Activator Gene of the Human T Cell Lymphotropic Virus Type III Is Required for Replication," *Cell,* 44:941–947 (Mar. 28, 1986).

Dzierzak et al., "Lineage–Specific Expression of a Human β–Globin Gene In Murine Bone Marrow Transplant Recipients Reconstituted With Retrovirus–transduced Stem Cells," *Nature,* 331:35–41, (Jan. 7, 1988).

Felber et al., "A Quantitative Bioassay for HIV–1 Based On Trans–Activation," *Science,* 239:184–187 (Jan. 8, 1988).

Felgner et al., "Lipofection: A Highly Efficient, Lipid–Mediated DNA–Transfection Procedure," *Proc. Nat'l. Acad. Sci., USA,* 84:7413–1417 (Nov. 1987).

Frankel et al., "Dimerization of the Tat Protein from Human Immunodeficiency Virus: A Cysteine–Rich Peptide Mimics the Normal Metal–Linked Dimer Interface," *Proc. Nat'l Acad. Sci., USA,* 85:7297–6300 (Sep., 1988).

Frankel et al., "Tat Protein From Human Immunodeficiency Virus Forms A Metal–Linked Dimer," *Science,* 240:70–73, (Apr., 1988).

Friedman et al., "Expression of a Truncated Viral Trans–Activator Selectively Impedes Lytic Infection By Its Cognate Virus," *Nature,* 335:452–454 (Sep. 29, 1988).

Furman et al., "Inhibition of Herpes Simplex Virus–Induced DNA Polymerase Activity and Vital DNA Replication by 9–(2–Hydroxyethoxymethyl)guanine and Its Triphosphate," *J. Virology,* 32(1):72–77 (Oct. 1979).

Ganz et al., "Defensins Natural Peptide Antibiotics . . . ," *J. Clin. Invest.,*76:1427–1435 (Oct., 1985).

Goelz, S.E., "Hypomethylation of DNA from Benign and Malignant Human Colon Neoplasms," *Science,* 228:187–190 (Apr. 12, 1985).

Graham et al., "A New Technique for the Assay of Infectivity of Human Adenovirus 5 DNA," *J. Virology,* 52:456–467 (1973).

Guild et al., "Development of Retrovirus Vectors Useful for Expressing Genes in Cultured Murine Embryonal Cells and Hematopoietic Cells in Vivo," *J. Virol.,* 62(10): 3795–3801 (1988).

Haynes, B.F., "Scientific and Social Issues of Human Immunodeficiency Virus Vaccine Development," *Science,* 260:1279–1286 (May 28, 1993).

Hirsch, M.S., "Aids Commentary: Azidothymidine," *J. Infect., Dis.,* 157(3):427–431 (1988).

Ho et al., "A T–Cell–Specific Transcriptional Enhancer Element 3' of $C_\alpha$ the Human T–Cell Receptor a Locus," *Proc. Nat'l. Acad. Sci., USA,* 86:6714–6718 (Sep., 1989).

Johnston et al., "Present Status and Future Prospects for HIV Therapies," *Science,* 260:1286 (May 28, 1993).

Kantoff et al., "Correction of Adenosine Deaminase Deficiency in Cultured Human T and B Cells by Retrovirus–mediated Gene Transfer," *Proc. Natl. Acad. Sci., USA,* 83:6563 (Sep. 1986).

Kriegler et al., "Transformation Mediated by the SV40 T Antigens: Separation of the Overlapping SV40 Early Genes with a Retroviral Vector," *Cell,* 38:483–491 (Sep., 1984).

Malim et al., The HIV–1 rev trans–Activator Acts Through a Structured Target Sequence to Activate Nuclear Export of Unspliced Vital mRNA, *Nature,* 338:254–257 (1989).

Maniatis et al., *Molecular Cloning: A Laboratory Manual,* Cold Spring Harbor Laboratory, Cold Spring Harbor Press, Cold Spring Harbor N.Y., pp. 22–26 (1982).

Maniatis et al., "Regulation of Inducible and Tissue–Specific Gene Expression," *Science,* 236:1237–1245 (Jun. 5, 1987).

Mansour et al., "Disruption Of The Proto–Oncogene int–2 In Mouse Embryo Derived Stem Cells: A General Strategy for Targeting Mutations to NonSelectable Genes," *Nature*, 336:348–352 (Nov. 1988).

Mariman, E.C.M., "New Strategies for AIDS Therapy and Prophylaxis," *Nature*, 318:414 (1985).

Miller et al., "Redesign of Retrovirus Packaging Cell Lines to Avoid Recombination Leading To Helper Virus Production," *Mol. Cell. Biol.*, 6(8):2895–2902 (Aug. 1986).

Mitsuya et al., "Strategies for Antiviral Therapy for AIDS," *Nature*, 325:773–778 (Feb. 26, 1987).

Moolten, F.L., "An Alternative to the Magic Bullet Paradigm for Specific Cancer Therapy," *Medical Hypotheses*, 24:43–51 (1987).

Moolten, F.L., "Tumor Chemosensitivity Conferred by Inserted Herpes Thymidine Kinase Genes: Paradigm for a Prospective Cancer Control Strategy," *Cancer Research*, 46:5276–5281 (Oct., 1986).

Muesing et al., "Regulation of mRNA Accumulation by a Human Immunodeficiency Virus Trans–Activator Protein," *Cell*, 48:691–701 (1987).

Nabel et al., "Alternative Mechanisms for Activation of Human Immunodeficiency Virus Enhancer in T Cells," *Science*, 239:1299–1302 (1988).

Overhauser et al., "Generation of Glucocorticoid Responsive Moloney Murine Leukemia Virus by Insertion of Regulatory Sequences from Murine Mammary Tumor Virus into the Long Terminal Repeat," *J. Virol.*, 54(1):133–144 (1985).

Palmiter et al., "Cell Lineage Ablation In Transgenic Mice By Cell Specific Expression Of A Toxin Gene," *Cell*, 80:435–443 (1987).

Patarca et al., "rpt–1, An Intracellular Protein From Helper/Inducer T Cells That Regulates Gene Expression of Interleukin 2 Receptor and Human Immunodeficiency Virus Type 1," *Proc. Nat'l Acad. Sci.*, 85:2733–2737 (1988).

Peterlin et al., "Elevated Levels of mRNA Can Account for the Trans–activation of Human Immunodeficiency Virus," *Proc. Nat'l Acad. Sci., USA*, 83:9734–9738 (Dec., 1986).

Phelps et al., "The Human Papillomavirus Type 16 E7 Gene Encodes Transactivation and Transformation Functions Similar to Those of Adenovirus EIA," *Cell*, 53:539–547 (May 20, 1988).

Piatak et al., "Expression of Soluble and Fully Functional Ricin A Chain in *Escherichia coli* is Temperature–Sensitive," *J. Biol. Chem.*, 263(10):4837–4843 (1988).

Selsted et al., "Primary Structures of Three Human Neutrophil Defensins," *J. Clin. Invest.*, 76:1436–1439 (Oct., 1985).

Shinnick et al., "Nucleotide Sequence of Moloney Murine Leukaemia Virus," *Nature*, 293:543–548 (1981).

Smith et al., "Blocking of HIV–1 Infectivity by a Soluble, Secreted Form of the Antigen," *Science*, 238:1704–1707 (Dec. 18, 1987).

Sodroski et al., "Trans–Acting Transcriptional Regulation of Human T–Cell Leukemia Virus Type III Long Terminal Repeat," *Science*, 22:171–173 (Jan. 11, 1985).

Sodroski et al., "Location Of The Trans–Activating Region On The Genome of Human T–Cell Lymphotropic Virus Type III," *Science*, 229:74–77 (Jul. 5, 1985).

Tellier et al., "New Strategies for AIDS Therapy and Prophylaxis," *Nature*, 318:414 (1985).

Treisman, "Identification of a Protein–Binding Site That Mediates Transcriptional Response of the C–fos Gene to Serum Factors," *Cell*, 46:567–574 (Aug. 15, 1986).

Van Beveran et al., "Nucleotide Sequence of the Genome of a Murine Sarcoma Virus," *Cell*, 27:97–108 (1981).

Walbot et al., "Plant Development and Ribozymes for Pathogens," *Nature*, 334:196–197 (Jul. 21, 1988).

Wasmoen et al., "Biochemical and Amino Acid Sequences Analysis of Human Eosinophil Granule Major Basic Protein," *J. Biol. Chem.*, 263:12559–12563 (1988).

Yee et al., "Gene Expression From Transcriptionally Disabled Retroviral Vectors," *Proc. Nat'l Acad. Sci., USA*, 84:5197–5201 (Aug., 1987).

Yu et al., "Self–Inactivating Retroviral Vectors Designed for Transfer of Whole Genes into Mammalian Cells," *Proc. Nat'l Acad. Sci., USA*, 83:3194–3198 (May, 1986).

Maxwell et al., "Regulated Expression of a Diptheria Toxin A–Chain Gene Transfected Into Human Cells: Possible Strategy For Inducing Cancer Cell Suicide," *Cancer Research*, 46:4660–4664 (1986).

Maxwell et al., "Regulated Expression of a Transfected Toxin Gene," *J. Cell. Biochem.*, Supplement 10D:39 (Abstract N93) (1986).

Maxwell et al., "HTLV–Regulated Expression of a Transfected Diptheria Toxin Gene," *J. Cell. Biochem.*, Supplement 11D:67 (Abstract P314) (1987).

Harrison et al., "Toward HIV–Regulated Expression of a Diptheria Toxin A Gene In Transfected Cells," *J. Cell. Biochem.*, Supplement 13B:302 (Abstract G418) (Jan. 21, 1989).

Verma et al., "Expression and Regulation of Rat Growth Hormone Gene in Mouse Fibroblasts," In: *Eukaryotic Viral Vectors*, Gluzman, Y. (Ed.), Cold Spring Harbor Laboratory, pp. 159–164 (1982).

Arnold et al., "Vaccine Development for Aids Through Molecular Surgery of a Human Common Cold Virus Surface," *J. Cell. Biochem.*, L401:145 (1990).

Buseyne et al., "Detection of HIV–Specific Cell–mediated Cytotoxicity in the Peripheral Blood from Infected Children," *J. Immunology*, 150(8):3569–3581 (1993).

Carmichael et al., "Quantitative Analysis of the Human Immunodeficiency Virus Type 1 (HIV–1)–Specific Cytotoxic T Lymphocyte (CTL) Response at Different Stages of HIV–1 Infection: Differential CTL Responses to HIV–1 and Epstein–Barr Virus in Late Disease," *J. Exp. Med.*, 177:249–256 (1993).

Chada et al., "Cross–Reactive Lysis of Human Targets Infected with Prototypic and Clinical Human Immunodeficiency Virus Type 1 (HIV–1) Strains by Murine Anti–HIV–1 IIIB env–Specific Cytotoxic T Lymphocytes," *J. Virol.* 67(6):3409–3417 (1993).

Dadaglio et al., "Enhancement of HIV–specific Cytotoxic T Lymphocytes Responses by Zidovudine (AZT) Treatment," *Clin. Ex. Immunol.*, 87:7–14 (1992).

De Baetselier et al., "Differential Expression of H–2 Gene Products in Tumour Cells is Associated with Their Metastatogenic Properties," *Nature*, 288:179–181 (1980).

Doherty et al., "Recombinant Vaccinia Viruses and the Development of Immunization Strategies Using Influenza Virus," *J. Inf. Disease*, 159(6):1119–1122 (1989).

Ellrodt et al., "The Hidden Dangers of AIDS Vaccination," *Nature*, 325:765 (1987).

Fauci et al., "Development and Evaluation of a Vaccine for Human Immunodeficiency Virus (HIV) Infection," *Ann. Intern. Med.*, 110:373–385 (1989).

Holt et al., "Inducible Production of c–fos Antisense RNA Inhibits 3T3 Cell Proliferation," *Proc. Nat'l Acad. Sci., USA*, 83:4794–4798 (1986).

Hu et al., "Effect of Immunization with a Vaccinia–HIV env Recombinant on HIV Infection of Chimpanzees," *Nature*, 328:721–723 (1987).

Hussey et al., "A Soluble CD4 Protein Selectively Inhibits HIV Replication and Syncytium Formation," *Nature*, 331:78–81 (1988).

Izant & Weintraub, "Constitutive and Conditional Suppression of Exogenous and Endogenous Genes by Anti–Sense RNA," *Science*, 229:345–352 (1985).

Joly et al., "Cell–Mediated Suppression of HIV–Specific Cytotoxic T Lymphocytes," *J. Immunol.*, 143(7):2193–2201 (1989).

Lathe et al., "Tumor Prevention and Rejection With Recombinant Vaccinia," *Nature*, 326:878–880 (1987).

Ledley et al., "Retroviral–mediated Gene Transfer of Human Phenylalanine Hydroxylase into NIH 3T3 and Hepatoma Cells," *Proc. Nat'l Acad. Sci.*, 83:409–413 (Jan., 1986).

Lotze et al., "Recent Advances in Cellular Immunology: Implications for Immunity to Cancer," *Immunology*, 11:190–193 (1990).

McCormick, D., "Human Gene Therapy: The First Round," *BioTechnology*, 3(8):689–693 (1985).

McCune et al., "Endoproteolytic Cleavage of gp160 Is Required for the Activation of Human Immunodeficiency Virus," *Cell*, 53:55–67 (1988).

Mercola et al., "Insertion of a New Gene of Viral Origin into Bone Marrow Cells of Mice," *Science*, 208:1033–1035 (1980).

Miedema et al., "Maintenance of High Level Cytotoxic T–Cell (CTL) Response in Long–Term Survivors of HIV Infection," *J. Cell. Biochem.*, Supplement 17D:75 (Abstract N350) (1993).

Mulligan, R.C., "Construction of Highly Transmissible Mammalian Cloning Vehicles Derived from Murine Retroviruses," *Experimental Manipulation of Gene Expression*, 8:155–173 (1983).

Mosier et al., "Resistance to Human Immunodeficiency Virus 1 Infection of SCID Mice Reconstituted With Peripheral Blood Leukocytes from Donors Vaccinated With Vaccinia gp160 and Recombinant gp160," *Proc. Nat'l Acad. Sci., USA*, 90:2443–2447 (1993).

Newell et al., "Herpes Simplex Virus–Induced Stromal Keratitis: Role of T–Lymphocyte Subsets in Immunopathology," *J. Virol.*, 63(2):769–775 (1989).

Salk, J., "Prospects for the Control of AIDS by Immunizing Seropositive Individuals," *Nature*, 327:473–476 (1987).

Shinitzky et al., "Cancer Immunotherapy With Autologous and Allogeneic Vaccines: A Practical Overview," *EORTC Gentitourinary Group Monograph Basic Research and Treatment of Renal Cell Carcinoma Metastasis*, 9:95–125 (1990).

Strebel et al., "The HIV 'A' (sor) Gene Product is Essential for Virus Infectivity," *Nature*, 358:728–730 (1987).

Temin, H.M., "Retrovirus Vectors: Promise and Reality," *Science*, 246:983 (1989).

Torpey, III et al., "Effects of Adoptive Immunotherapy with Autologous CD8+ T Lymphocytes on Immunologic Parameters: Lymphocytes Subsets and Cytotoxic Activity," *Clinical Immunol. & Immunopath.*, 68(5):263–272 (1993).

Voss et al., "Potential Significance of the Cellular Immune Response against the Macaque Strain of Simian Immunodeficiency Virus ($SIV_{MAC}$) in Immunized and Infected Rhesus Macaques," *J. Gen. Virology*, 73:2273–2281 (1992).

Yasutomi et al., "Simian Immunodeficiency Virus–Specific CD8+ Lymphocyte Response in Acutely Infected Rhesus Monkeys," *J. Virol.*, 67(3):1707–1711 (1993).

Zagury et al., "Immunization Against AIDS in Humans," *Nature*, 326:249–250 (1987).

Czarniecki et al., "Synergistic Antiviral and Antiproliferative Activities of *Escherichia coli*–Derived Human Alpha, Beta, and Gamma Interferon," *J. of Virology*, 49(2):490–496 (Feb., 1984).

Davison et al., "The Complete DNA Sequence of Varicella–Zoster Virus," *J. Gen. Virol.*, 67:1759–1816 (1986).

Deen et al., "A Soluble Form of CD4 (T4) Protein Inhibits AIDS Virus Infection," *Nature*, 331:82–84 (Jan. 7, 1988).

Howell et al., "Gene Therapy for Thioguanine–resistant Human Leikemia," *Mol. Biol. Med.*, 4:157–168 (1987).

Katoh et al., "Inhibition of Retroviral Protease Activity by an Aspartyl Proteinase Inhibitor," *Nature*, 329:654–656 (Oct. 15, 1987).

Rein et al., "Myristylation Site in $Pr65^{gag}$ is Essential for Virus Particle Formation by Moloney Murine Leukemia Virus," *Proc. Nat'l Acad. Sci., USA*, 83:7246–7250 (Oct., 1986).

Sleckman et al., "Expression and Function of CD4 in Murine T–Cell Hybridoma," *Nature*, 328:351–353 (Jul. 23, 1987).

Stratowa et al., "Recombinant Retroviral DNA Yielding High Expression of Hepatitis B Surface Antigen," *EMBO J.*, 1(12):1573–1578 (1982).

Tabin et al., "Adaptation of a Retrovirus as a Eukaryotic Vector Transmitting the Herpes Simplex Virus Thymidine Kinase Gene," *Mol. & Cell. Biology*, 2(4):426–436 (Apr., 1982).

Temin, H.M., "Retrovirus Vectors for Gene Transfer: Efficient Integration Into and Expression of Exogenous DNA in Vertebrate Cell Genomes," In: *Gene Transfer*, Kucherlapati (Ed.), Plenum Press, New York, pp. 149–187 (1986).

Wachsman et al., "HTLV x Gene Mutants Exhibit Novel Transcriptional Regulatory Phenotypes," *Science*, 235:674–677 (Feb. 6, 1987).

Lang et al., "Expression of a Hemopoietic Growth Factor cDNA in a Factor–Dependnet Cell Line Results in Autonomous Growth and Tumorigenicity," *Cell*, 43:531–542 (1985).

Kuriyama et al., "Gene therapy for the treatment of hepatoma by retroviral–mediated gene–transfer of the herpes–simplex virus thymidine kinase gene," *Int. Hepatol. Commun.* 1(5):253–259 (1993).

Kuriyama et al. (b), "A potential approach for gene therapy targeting hepatoma using a liver–specific promoter on a retroviral vector," *Cell Struct. Funct.*, 16:503–510 (1991).

Pizer et al., "A mammalian cell line designed to test the mutagenic activity of anti–herpes nucleosides," *Int. J. Cancer*, 40:114–121 (1987).

Besnard et al. "Selection against expression of the *Escherichia coli* gene gpt in hprt + mouse teratocarcinoma and hybrid cells," *Mol. Cell. Biol.*, 7(11):4139–4141 (Nov. 1987).

Borrelli et al., "Targeting of inducible toxic phenotype in animal cells," *Proc. Nat. Acad. Sci. USA*, 85:7572–7576 (Oct. 1988).

Nelson, et al. "Gene replacement therapy for inborn errors of purine metabolism," *Cold Spring Harbor Symp. Quant. Biol.* 51(2):1065–1071 (1986).

Trucco, "Molecular mechanisms involved in the etiology and pathogenesis of autoimmune diseases," *Clin. Investig.* 70:756–765 (1992).

Bachmann, et al., "In Vivo versus In Vitro Assays for Assessment of T– and B–cell Function," *Immunological Techniques*, 6:320–326 (1994).

Chan, et al., "Mammalian Sarcoma–Leukemia Viruses. I. Infection of Feline, Bovine, and Human Cell Cultures With Snyder–Theilen Feline Sarcoma Virus," *Journal of the Natl. Cancer Inst.*, 52(2):473–478 (Feb. 1974).

Donner, et al., "McDonough Feline Sarcoma Virus: Characterization of the Molecularly Cloned Provirus and Its Feline Oncogene (v–fms)," *Journal of Virology*, 41(2):489–500 (Feb. 1982).

Jolly, et al., "Variable Stability of a Selectable Provirus After Retroviral Vector Gene Transfer Into Human Cells," *Molecular and Cellular Biology*, 6(4):1141–1147 (Apr. 1986).

Lee, Robert E., "Gene Therapy: clipping the wings of nature's own gene transfer vectors," *Can. Med. Assoc. J.*, 134:311–313 (Feb. 15, 1986).

Ruscetti, et al., "Three Independent Isolates of Feline Sarcoma Virus Code for Three Distinct gag–x Polyproteins," *Journal of Virology*, 35(1):259–264 (Jul. 1980).

Suter, et al., "Cytotoxic Immune Response of Puppies to Feline Sarcoma Virus Induced Tumors," *Veterinary Immunology and Immunopathology*, 7:131–138 (1984).

Willis, et al., "Partial Phenotypic Correction of Human Lesch–Nyhan (Hypoxanthine–Guanine Phosphoribosyl-transferase–deficient) Lymphoblasts with a Transmissible Retroviral Vector," *The Journal of Biological Chemistry*, 259(12):7842–7849 (Jun. 25, 1984).

Klein, G., "Tumor Antigens," *Ann. Rev. Microbiol.* 20:223–252 (1966).

Hellström, "Cellular Immunity Against Tumor Antigens," *Adv. Cancer Res.* 12:167–223 (1969).

Bishop, J.M., "Cancer Genes Come Of Age," *Cell* 32:1018–1020 (1983).

Hellström and Hellström, "Oncogene–associated Tumor Antigens as Targets for Immunotherapy," *FASEB J.* 3:1715–1722, (1989).

Miller, et al., "Treatment of B–Cell Lymphoma With Monoclonal Anti–Idiotype Antibody," *New England J. Med.* 306:517–522, (1982).

Bartram et al., "Translocation of c–abl Oncogene Correlates with the Presence of a Philadelphia Chromosome in chronic Myelocytic Leukaemia," *Nature* 306:277–280 (1983).

Yasukawa and Zarling, "Human Cytotoxic T Cell Clones Directed Against Herpes Simplex Virus–Infected Cells. III. Analysis of Viral Glycoproteins Recognized by CTL Clones by Using Recombinant Herpes Simplex Viruses," *J. Immunol.* 134(4):2679–2682, 1985.

Zarling, et al., "Human Cytotoxic T Cell Clones Directed Against Herpes Simplex Virus–Infected Cells. IV. Recognition and Activation by Cloned Glycoproteins gB and gD," *J. Immunol.* 136(12):4669–4673 (1986).

Zarling, et al., "Herpes Simplex Virus (HSV)–Specific Human T–Cell Clones Recognize HSV Glycoprotein D Expressed by a Recombinant Vaccinia Virus," *J. Virol.* 59(2);506–509 (1986).

Torseth, et al., "Native and Recombinant Herpes Simplex Virus Type 1 Envelope Protein Induce Human Immune T–Lymphocyte Responses," *J. Virol.* 61(5):1532–1539 (1987).

Caruso et al., "Regression of established macroscopic liver metastases after in situ transduction of a suicide gene," *Proc. Natl. Acad. Sci., USA*, 90:7024–7028, Medical Sciences (Aug. 1993).

Chen et al., "Combination Suicide and Cytokine Gene Therapy for Hepatic Metastases of Colon Carcinoma: Sustained Antitumor Immunity prolongs Animal Survival," *Cancer Research*, 56:3758–3762 (Aug. 15, 1996).

DiMaio et al., "Directed enzyme po–drug gene therapy for pancreatic cancer in vivo," *Surgery*, 116(2):203–213 (Aug. 1994).

Hurford et al., "Gene therapy of metastatic cancer by in vivo gene targeting," *Nature Genetics*, 10:430–435 (Aug. 1995).

O'Malley et al., "Adenovirus–mediated Gene Therapy for Human Head and Neck Squamous Cell Cancer in a Nude Mouse Model," *Cancer Research*, 55:1080–1085 (Mar. 1995).

O'Malley et al., "Combination Gene Therapy for Oral Cancer in a Murine Model," *Cancer Research*, 56:1737–1741 (Apr. 15, 1996).

Tanaka et al., "Adenovirus–mediated Prodrug Gene Therapy for Carcinoembryonic Antigen–producing Human Gastric Carcinoma Cells In Vitro," *Cancer Research*, 56:1341–1345 (Mar. 15, 1996).

Trinh et al., "Enzyme/Prodrug Gene Therapy: Comparison of Cytosine Deaminase/5–Fluorocytosine Versus Thymidine Kinase/Ganciclovir Enzyme/prodrug Systems in a Human Colorectal Carcinoma Cell Line," *Cancer Research*, 55:4808–4812 (Nov. 1, 1995).

Yang et al., "Gene Therapy of Metastatic Pancreas Cancer with Intraperitoneal Injections of Concentrated Retroviral Herpes simplex Thymidine Kinase Vector Supernatant and Ganciclovir," *Annals of Surgery* 224(3):405–417 (1996).

Yamamoto et al., "Cloning and Sequencing of Mouse Tyrosinase cDNA", *Jpn. J. Genet.*, 62:271–274 (1987).

Kwon, et al., *Biochem. & Biophys. Research Communications*, 153(3):1301–1309 (Jun. 30, 1988).

Ruppert et al., "Multiple Transcripts of the Mouse Tyrosinase Gene are Generated by Alternative Splicing," *EMBO Journal*, 7(9):2715–2722 (1988).

Ram et al., "Summary of Results and Conclusions of the Gene Therapy of Malignant Brain Tumors: Clinical Study," J. Neurosurg., 82:Abstract 343A (Feb. 1995).

Bordignon, "Transfer of the HSV–TK Gene into Donor Peripheral Blood Lymphocytes for In Vivo Modulation of Donor Anti–Tumor Immunity After ALLO–BMT," *Brit. J. Of Haemat.93*:306 Abstract 1162 (1996).

Mavilio et al., "Peripheral Blood Lymphocytes as Target Cells of Retroviral–Mediated Gene Transfer," *Blood*, 83(7): 1988–1997 (Apr. 11, 1994).

Bonini et al., "HSV–TK Gene Transfer into Donor Lymphocytes for Control of Allogeneic Graft–Versus–Leukemia," *Science*, 276:1719–1724 (Jun. 13, 1997).

Lundwall, et al., "Molecular Cloning of Human Prostate Specific Antigen cDNA," *FEB*, 214(2):317–322 (Apr. 1987).

Schulz, et al., "Sequence of a cDNA Encoding the Complete Mature Human Prostate Specific Antigen (PSA) and an Unspliced Leader Sequence," *Nucleic Acids Res.*, 16(13):6226 (1988).

Riegman, et al., "Molecular Cloning and Characterization of Novel Prostate Antigen cDNAs," *Biochem. Biophys. Res. Comm.,* 155(1):181–188 (Aug. 30, 1988).

Lundwall, et al., "Characterization of the Gene for Prostate–specific Antigen, a Human Glandular Kallikrein," *Biochem. Biophys. Res. Comm.,* 161(3):1151–1159 (Jun. 30, 1989).

Calabretta, et al., "Altered Expression of $G_1$ specific Genes in Human Malignant Myeloid Cell", *PNAS, USA,* 83:1495–1498 (Mar. 1986).

Huber, et al., "Retroviral–Mediated Gene Therapy For The Treatment Of Hepatocellular Carcinoma: An Innovative Approach for Cancer Therapy," *PNAS, USA,* 88:8039–8043 (Sep. 1991).

Austin and Huber, "A First Step in the Development of Gene Therapy for Colorectal Carcinoma: Cloning, Sequencing, and Expression of *E. coli* Cytosine Deaminase," *Mol. Pharm.,* 43:380–387 (1993).

Huber et al., "In Vivo Antitumor Activity of 5–Fluorocytosine on Human Colorectal Carcinoma Cells Genetically Modified to Express Cytosine Deaminase," *Cancer Research,* 53:4618–4626 (Oct. 1, 1993).

Huber et al., "Metabolism of 5–Fluorocytosine to 5–Fluorouracil in Human Colorectal Tumor Cells Transduced with the cytosine Deaminase Gene: Significant Antitumor Effects When Only a Small Percentage of Tumor Cells Express Cytosine Deaminase," *PNAS USA,* 91:8302–8306 (Aug. 1994).

Sawyer et al., "Mapping the Varicella Zoster Virus Deoxypyrimidine Kinase Gene and Preliminary Identification of its Transcript," *Virology,* 149:1–9 (1986).

Haj–Ahmad et al., "Development of a Helper–Independent Adenovirus Vector and Its Use in the Transfer of the Herpes Simplex Virus Thymidine Kinase gene," *J. of Virology,* 57(1):267–274 (Jan. 1986).

Chen et al., "Combination Gene Therapy for Liver Metastasis of Colon Carcinoma In Vivo," *PNAS USA,* 92:2577–2581 (Mar. 1995).

Vile et al., "Systemic Gene Therapy of Murine Melanoma Using Tissue Specific Expresesion of the HSVtk Gene Involves an Immune Component," *Cancer Res.* 54:6228–6232 (1994).

Oldfield, et al., "Gene Therapy for the Treatment of Brain Tumors Using Intra–Tumoral Transduction with the Thymidine Kinase Gene and Intravenous Ganciclovir," *Human Gene Therapy,* 4:39–69.

Hirochika et al., "Functional Mapping of the Human Papillomavirus Type 11 Transcriptional Enhancer and its Interaction with the trans–acting E2 Proteins", *Genes & Develop.,* 2:54–67 (1988).

Caruso et al., "Gene Therapy Against Cancer and HIV Infection Using the Gene Encoding Herpes Simplex Virus Thymidine Kinase," *Molecular Medicine Today:* pp. 212–217 (May 1996).

Shibahara et al. "Cloning And Expression of cDNA Encoding Mouse Tyrosinase," *Nucleic Acids Research,* 14(6):2413–2427 (1986).

Ledley, Somatic Gene Therapy for Human Disease: Background and Prospects, Part II, *The Journal of Pediatrics,* 110(2):167–174 (Feb., 1987).

Sorge, et al., "Complete Correction of the Enzymatic Defect of Type I Gaucher Disease Fibroblasts by Retroviral–Mediated Gene Transfer," *Proc. Natl. Acad., Sci. USA* 84:906–909 (Feb. 1987).

Palmer, et al., "Efficient Retrovirus–Mediated Transfer and Expression of a Human Adenosine Deaminase Gene In Diploid Skin Fibroblasts from an Adenosine Deaminase–Deficient Human," *Proc. Natl. Acad. Sci. USA* 84:1055–1059 (Feb. 1987).

Hwang, et al., "Expression of Genes Introduced into Cells by Retroviral Infection Is More Efficient Than That of Genes Introduced Into Cells by DNA Transfection," *Journal of Virology,* 50(2):417–424 (May 1984).

Davidson, et al., "The Complete DNA Sequence of Varicella–Zoster Virus," *J. Gen. Virol.* 67:1759–1816 (1986).

Culver, et al., "In Vivo Gene Transfer with Retroviral Vector–Producer Cells for Treatment of Experimental Brain Tumors," *Science,* 256:1550–1552 (Jun. 12, 1992).

Ram et al., "In Situ Retroviral–mediated Gene Transfer for the Treatment of Brain Tumors in Rats," *Cancer Research,* 53:83–88 (Jan. 1, 1993).

Cone et al., "High–efficiency Gene Transfer Into Mammalian Cells: Generation of Helper–free Recombinant Retrovirus with Broad Mammalian Host Range," *Proc. Natl. Acad. Sci. USA,* 81:6349–6353 (Oct. 1984).

* cited by examiner

ADENOVIRAL VECTORS ENCODING A CYTOKINE AND A CONDITIONALLY LETHAL GENE

CROSS-REFERENCE TO RELATED APPLICATIONS

This application is a division of U.S. Ser. No. 08/155,944, filed Nov. 18, 1993, now abandoned, which is a continuation-in-part of U.S. Ser. No. 08/139,994, filed Oct. 20, 1993, now abandoned, which is a continuation of U.S. Ser. No. 07/965,084, filed Oct. 22, 1992, now abandoned.

TECHNICAL FIELD

The present invention relates generally to viral vectors, and more specifically, to recombinant viral vectors which are capable of delivering vector constructs to susceptible target cells. These vector constructs are typically designed to deliver a gene product which is capable of activating a compound with little or no activity into an active product.

BACKGROUND OF THE INVENTION

Although many bacterial diseases are, in general, easily treated with antibiotics, very few effective treatments exist for many viral, cancerous, and other diseases, including genetic diseases. For example, cancer now accounts for one-fifth of the total mortality in the United States, and is the second leading cause of death. Briefly, cancer is typically characterized by the uncontrolled division of a population of cells. This uncontrolled division typically leads to the formation of a tumor, which may subsequently metastasize to other sites.

Cancer, in general, represents a class of diseases which are very difficult to treat. For example, although primary solid tumors can generally be treated by surgical resection, a substantial number of patients that have solid tumors also possess micrometastases beyond the primary tumor site. If treated with surgery alone, many of these patients will experience recurrence of the cancer. Therefore, in addition to surgery many cancers are now also treated with cytotoxic chemotherapeutic drugs (e.g., vincristine, vinblastine, cisplatin, methotrexate, 5-FU, etc.) and/or radiation therapy. One difficulty with this approach however, is that radiotherapeutic and chemotherapeutic agents are toxic to normal tissues, and often create life-threatening side effects. In addition, these approaches often have extremely high failure/remission rates (up to 90% depending upon the type of cancer).

Various other therapies have thus been attempted, in an effort to bolster or augment an individual's own immune system to eliminate cancer cells. Several such therapies have utilized bacterial or viral components as adjuvants, in order to stimulate the immune system to destroy the tumor cells. Examples of such components include BCG, endotoxin, mixed bacterial vaccines, interferons ($\alpha$, $\beta$, and $\gamma$), interferon inducers (e.g., *Brucella abortus*, and various viruses), and thymic factors (e.g. thymosin fraction 5, and thymosin alpha-1) (see generally "Principles of Cancer Biotherapy," Oldham (ed.), Raven Press, New York, 1987). Such agents have generally been useful as adjuvants and as nonspecific stimulants in animal tumor models, but have not yet proved to be generally effective in humans.

Lymphokines have also been utilized in the treatment of cancer. Briefly, lymphokines are secreted by a variety of cells, and generally have an effect on specific cells in the generation of an immune response. Examples of lymphokines include Interleukins (IL)-1, -2, -3, and -4, as well as colony stimulating factors such as G-CSF, GM-CSF, and M-CSF. Recently, one group has utilized IL-2 to stimulate peripheral blood cells in order to expand and produce large quantities of cells which are cytotoxic to tumor cells (Rosenberg et al., *N. Engl. J. Med.* 313:1485–1492, 1985).

Others have suggested the use of antibody-mediated anti-cancer therapies. Briefly, antibodies may be developed which recognize certain cell surface antigens that are either unique, or more prevalent on cancer cells compared to normal cells. These antibodies, or "magic bullets," may be utilized either alone or conjugated with a toxin in order to specifically target and kill tumor cells (Dillman, "Antibody Therapy," *Principles of Cancer Biotherapy*, Oldham (ed.), Raven Press, Ltd., New York, 1987). For example, Ball et al. (*Blood* 62:1203–1210, 1983) treated several patients with acute myelogenous leukemia with one or more of several monoclonal antibodies specific for the leukemia, resulting in a marked decrease in circulating leukemia cells during treatment. Similarly, others have utilized toxin-conjugated antibodies therapeutically to treat a variety of tumors, including, for example, melanomas, colorectal carcinomas, prostate carcinomas, breast carcinomas, and lung carcinomas (see Dillman, supra). One difficulty however, is that most monoclonal antibodies are of murine origin, and thus hypersensitivity against the murine antibody may limit its efficacy, particularly after repeated therapies. Common side effects include fever, sweats and chills, skin rashes, arthritis, and nerve palsies.

Therefore cancer has, as a general rule, been very difficult to treat utilizing either conventional or experimental pharmaceutical compositions.

Likewise, viral diseases have been very difficult to treat with conventional pharmaceutical compositions. In general, such pharmaceuticals have lacked specificity, exhibit a high overall toxicity, and have generally been found to be therapeutically ineffective.

Other techniques which have been developed for treating viral diseases involve the elicitation of an immune response to a pathogenic agent (i.e., the virus) through the administration of a noninfectious form of the virus (such as a killed virus), thereby providing antigens which act as an immunostimulant. Such an approach has proved useful for certain viruses (e.g., polio) but not for other viruses (e.g., HIV).

A more recent approach for treating viral diseases, such as acquired immunodeficiency syndrome (AIDS) and related disorders, involves blocking receptors on cells susceptible to infection by HIV from receiving or forming a complex with viral envelope proteins. For example, Lifson et al. (*Science* 232:1123–1127, 1986) demonstrated that antibodies to CD4 (T4) receptors inhibited cell fusion (syncytia) between infected and noninfected CD4 presenting cells in vitro. A similar CD4 blocking effect using monoclonal antibodies has been suggested by McDougal et al. (*Science* 231:382–385, 1986). Alternatively, Pert et al. (*Proc. Natl. Acad. Sci. USA* 83:9254–9258, 1986) reported the use of synthetic peptides to bind T4 receptors and block HIV infection of human T-cells, and Lifson et al. (*J. Exp. Med.* 164:2101, 1986) reported blocking both syncytia and virus/T4 cell fusion by using a lectin which interacts with a viral envelope glycoprotein, thereby blocking it from being received by CD4 receptors.

An alternative technique for inhibiting a pathogenic agent, such as a virus (which transcribes RNA), is to provide antisense RNA which complements at least a portion of the transcribed RNA, thereby inhibiting translation (To et al., *Mol. Cell. Biol.* 6:758,1986).

A major shortcoming, however, of the techniques described above is that they do not readily lend themselves to control the time, location or extent to which a drug, antigen, blocking agent or antisense RNA is utilized. In particular, since the above techniques require exogenous application of the treatment agent (i.e., exogenous to the sample in an in vitro situation), they are not directly responsive to the presence of the pathogenic agent. For example, it may be desirable to have an immunostimulant expressed in increased amounts immediately following infection by the pathogenic agent. In addition, in the case of antisense RNA, large amounts would be required for useful therapy in an animal, which under current techniques would be administered without regard to the location at which it is actually needed, that is, in cells infected with the pathogenic agent.

As an alternative to exogenous application, techniques have been suggested for producing treatment agents endogenously. More specifically, proteins expressed from viral vectors based on DNA viruses, such as adenovirus, simian virus 40, bovine papilloma, and vaccinia viruses, have been investigated. By way of example, Panicali et al. (*Proc. Natl. Acad. Sci. USA* 80:5364, 1983) introduced influenza virus hemagglutinin and hepatitis B surface antigens into the vaccinia genome and infected animals with the virus particles produced from such recombinant genes. Following infection, the animals acquired immunity to both the vaccinia virus and the hepatitis B antigen.

A number of difficulties however have been experienced to date with viral vectors based upon DNA viruses. These difficulties include: (a) the production of other viral proteins which may lead to pathogenesis or the suppression of the desired protein; (b) the capacity of the vector to uncontrollably replicate in the host, and the pathogenic effect of such uncontrolled replication; (c) the presence of wild-type virus which may lead to viremia; and (d) the transitory nature of expression in these systems. These difficulties have virtually precluded the use of viral vectors based on DNA viruses in the treatment of viral, cancerous, and other nonbacterial diseases, including genetic diseases.

Due to the nontransitory nature of their expression in infected target cells, retroviruses have been suggested as a useful vehicle for the treatment of genetic diseases (for example, see F. Ledley, *The Journal of Pediatrics* 110:1, 1987). However, in view of a number of problems, the use of retroviruses in the treatment of genetic diseases has not yet been widely accepted. Such problems relate to: (a) the apparent need to infect a large number of cells in inaccessible tissues (e.g., brain); (b) the need to cause these vectors to express in a very controlled and permanent fashion; (c) the lack of cloned genes; (d) the irreversible damage to tissue and organs due to metabolic abnormalities; and (e) the availability of other partially effective therapies in certain instances.

The present invention provides novel compositions and methods for treating a variety of diseases (e.g., viral diseases, cancer, genetic diseases and others), and further provides other, related advantages.

SUMMARY OF THE INVENTION

Briefly stated, the present invention provides recombinant viral vectors and methods of using such vectors for the treatment of a wide variety of pathogenic agents. Within one aspect of the invention, recombinant viral vectors are provided carrying a vector construct which directs the expression of a gene product capable of activating an otherwise inactive precursor into an active inhibitor of a pathogenic agent. Within one embodiment of the invention, the pathogenic agent is a virus-infected cell. Within another embodiment, the gene product is Herpes Simplex Virus Thymidine Kinase or Varicella Zoster Virus Thymidine Kinase. Within yet another embodiment, the inactive precursor is AZT.

Within another aspect of the present invention, recombinant viral vectors are provided carrying a vector construct which directs the expression of a gene product that activates a compound with little or no cytotoxicity into a toxic product. Within other aspects, recombinant viral vectors are provided carrying a vector construct which directs the expression of a gene product that activates a compound with little or no cytotoxicity into a toxic product in the presence of a pathogenic agent, thereby affecting localized therapy to the pathogenic agent. Within one embodiment, the gene product is Herpes Simplex Virus Thymidine Kinase, or Varicella Zoster Virus Thymidine Kinase. Within other embodiments, the gene product is selected from the group consisting of *E. coli* guanine phosphoribosyl transferase, alkaline phosphatase, fungal cytosine deaminase, carboxypeptidease G2, and Penicillin-V amidase. Within yet other embodiments, the pathogenic agent is a virus-infected cell, a cell infected with bacteria, a tumor cell, or a cell infected with a parasite.

Within other aspects of the invention, recombinant viral vectors are provided which direct the expression of a protein that is toxic upon processing or modification by a protein derived from a pathogenic agent. Within one embodiment, the protein which is toxic upon processing or modification is proricin.

Within yet another aspect of the invention, recombinant viral vectors are provided carrying a vector construct comprising a cytotoxic gene under the transcriptional control of an event-specific promoter, such that upon activation of the event-specific promoter the cytotoxic gene is expressed. Within various embodiments, the event-specific promoter is a cellular thymidine kinase promoter, or a thymidylate synthase promoter. Within another embodiment, the event-specific promoter is activated by a hormone. Within yet other embodiments, the cytotoxic gene is selected from the group consisting of ricin, abrin, diptheria toxin, cholera toxin, gelonin, pokeweed, antiviral protein, tritin, Shigella toxin, and Pseudomonas exotoxin A.

Within another aspect of the present invention, recombinant viral vectors are provided comprising a cytotoxic gene under the transcriptional control of a tissue-specific promoter, such that upon activation of the tissue-specific promoter the cytotoxic gene is expressed. Within various embodiments, the tissue-specific promoter is the phosphoenolpyruvate carboxykinase (PEPCK) promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, α or β globin promoter, T-cell receptor promoter, the osteocalcin promoter the IL-2 promoter, IL-2 receptor promoter, whey (wap) promoter, and the MHC Class II promoter.

Within yet another aspect of the present invention, viral vectors are provided carrying a vector construct comprising a cytotoxic gene under the transcriptional control of both an event-specific promoter and a tissue-specific promoter, such that the cytotoxic gene is maximally expressed only upon activation of both the event-specific promoter and the tissue-specific promoter. Representative event-specific and tissue-specific promoters have been discussed above. Within one preferred embodiment, the event-specific promoter is thymidine kinase, and the tissue-specific promoter is selected from the group consisting of the casein promoter and the HER2/neu promoter.

Within other aspects of the invention, viral vectors similar to those described above are provided, except that, in place of (or in addition to) the vector construct which directs the expression of a cytotoxic gene, the viral vector carries a vector construct which directs the expression of a gene product that activates a compound with little or no cytotoxicity into a toxic product.

Within other aspects of the present invention, the vector contructs described above may also direct the expression of additional non-vector derived genes. Within one embodiment the non-vector derived gene encodes a protein, such as an immune accessory molecule. Representative examples of immune accessory molecules include IL-1, IL-2, IL-3, IL-4, IL-5, IL-6, IL-7, IL-8, IL-9, IL-10, IL-11, IL-12, B7, B7-2, GM-CSF, CD3, ICAM-1, β-microglobulin, LFA-3, HLA Class I, and HLA Class II molecules. Within one preferred embodiment, the protein is gamma-interferon.

Within other aspects of the present invention, methods are provided for inhibiting or destroying pathogenic agents in a warm-blooded animal, comprising administering to a warm-blooded animal a recombinant viral vector as described above, such that the pathogenic agent is inhibited or destroyed. As utilized herein, it should be understood that the term "destroyed" refers to the destruction of cells which are responsible for a disease state, which destruction may result in only partial destruction of the disease (e.g., tumors may be only partially destroyed). Within various embodiments, the recombinant viral vector is administered in vivo, or alternatively, ex vivo. Within yet other embodiments, the pathogenic agent is a virus-infected cell, a cell infected with bacteria, or a tumor cell.

Within other aspects of the present invention, producer cells are provided which generate a recombinant viral vector as described above. Within another aspect, methods are provided for destroying pathogenic agents in a warm blooded animal, comprising administering to the animal such producer cells, in order to destroy the pathogenic agent.

Within another aspect of the present invention, methods are provided for destroying a pathogenic agent in a warm blooded animal, comprising the step of administering to the warm blooded animal nucleic acids which encode a gene product that activates a compound with little or no cytotoxicity into a toxic product, such that the pathogenic agent is destroyed.

Within yet another aspect of the invention, pharmaceutical compositions are provided, comprising a recombinant viral vector as described above, in combination with a pharmaceutically acceptable carrier or diluent.

These and other aspects of the present invention will become evident upon reference to the following detailed description and attached drawings. In addition, a number of patents, patent applications, and other publications are disclosed below which describe in more detail certain procedures or compositions (e.g., plasmids, etc.), and are therefore incorporated by reference in their entirety.

DETAILED DESCRIPTION OF THE INVENTION

Figure 1:
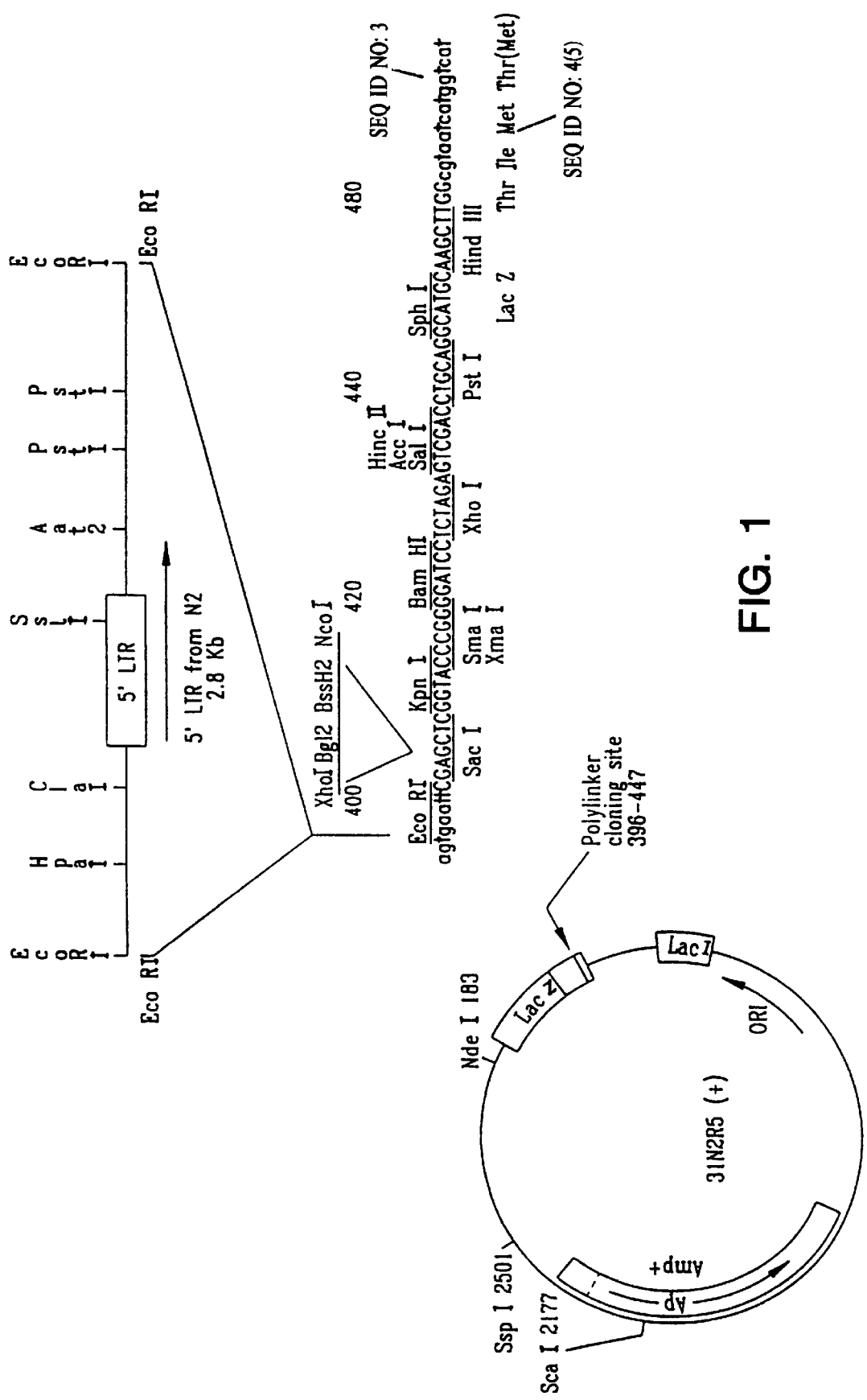
FIG. 1 is a schematic illustration of p31N2R5(+).

Prior to setting forth the invention, it may be helpful to an understanding thereof to first set forth definitions of certain terms that will be used hereinafter.

"Vector construct" refers to an assembly which is capable of directing the expression of the sequence(s) or gene(s) of interest. The vector construct must include transcriptional promoter/enhancer or locus defining element(s), or other elements which control gene expression by other means such as alternate splicing, nuclear RNA export, post-translational modification of messenger, or post-transcriptional modification of protein. In addition, the vector construct must include a sequence which, when transcribed, is operably linked to the sequence(s) or gene(s) of interest and acts as a translation initiation sequence.

Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct must include a packaging signal, long terminal repeats (LTRs), and positive and negative strand primer binding sites appropriate to the retrovirus used (if these are not already present).

"Pathogenic agent" refers to a cell which is responsible for a disease state. Representative examples of pathogenic agents include tumor cells, autoreactive immune cells, hormone secreting cells, cells which lack a function that they would normally have, cells that have an additional inappropriate gene expression which does not normally occur in that cell type, and cells infected with bacteria, viruses, or other intracellular parasites. In addition, as used herein "pathogenic agent" may also refer to a cell which over-expresses or inappropriately expresses a retroviral vector (e.g., in the wrong cell type), or which has become tumorigenic due to inappropriate insertion into a host cell's genome.

"Tissue-specific promoter" refers to transcriptional promoter/enhancer or locus defining elements, or other elements which control gene expression as discussed above, which are preferentially active in a limited number of tissue types. Representative examples of such tissue-specific promoters include the PEPCK promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, $\alpha$ or $\beta$ globin promoters, T-cell receptor promoter, or the osteocalcin promoter.

"Event-specific promoter" refers to transcriptional promoter/enhancer or locus defining elements, or other elements which control gene expression as discussed above, whose transcriptional activity is altered upon response to cellular stimuli. Representative examples of such event-specific promoters include thymidine kinase or thymidilate synthase promoters, $\alpha$ or $\beta$ interferon promoters and promoters that respond to the presence of hormones (either natural, synthetic or from other non-host organisms, e.g., insect hormones).

As noted above, the present invention provides recombinant viral vectors and methods of using such vectors for the treatment of a wide variety of pathogenic agents. Within one aspect of the invention, recombinant viral vectors are provided carrying a vector construct which directs the expression of a gene product capable of activating an otherwise inactive precursor into an active inhibitor of a pathogenic agent. As will be evident to one of skill in the art given the disclosure provided herein, a wide variety of inactive precursors may be converted into active inhibitors of a pathogenic agent. For example, antiviral nucleoside analogues such as AZT or ddC are metabolized by cellular mechanisms to the nucleotide triphosphate form in order to specifically inhibit retroviral reverse transcriptase, and thus viral replication (Furmam et al., *Proc. Natl. Acad. Sci. USA* 83:8333–8337, 1986). Recombinant viral vectors which direct the expression of a gene product (e.g., a protein) such as Herpes Simplex Virus Thymidine Kinase (HSVTK) or Varicella Zoster Virus Thymidine Kinase (VZVTK) which assists in metabolizing antiviral nucleoside analogues to their active form are therefore useful in activating nucleoside analogue precursors (e.g. AZT or ddC) into their active form.

Within one embodiment of the invention, the HSVTK gene may be expressed under the control of a constitutive macrophage or T-cell-specific promoter, and introduced into macrophage or T-cells. Constitutive expression of HSVTK results in more effective metabolism of nucleotide analogues such as AZT or ddC to their biologically active nucleotide triphosphate form, and thereby provides greater efficacy, delivery of lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, may also be utilized within the context of the present invention. A detailed description of several representative viral vectors is set forth in more detail below in Example 1.

Within a related aspect of the present invention, recombinant viral vectors are provided carrying a vector construct which directs the expression of a gene product that activates a compound with little or no cytotoxicity into a toxic product. Briefly, a wide variety of gene products which either directly or indirectly activate a compound with little or no cytotoxicity into a toxic product may be utilized within the context of the present invention. Representative examples of such gene products include HSVTK and VZVTK which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAU, FIAC, DHPG) to HSVTK, phosphorylates the drug into its corresponding active nucleotide triphosphate form.

Representative examples of other gene products which may be utilized 35 within the context of the present invention include: *E. coli* guanine phosphoribosyl transferase which converts thioxanthine into toxic thioxanthine monophosphate (Besnard et al., *Mol. Cell. Biol.* 7:4139–4141, 1987); alkaline phosphatase, which will convert inactive phosphorylated compounds such as mitomycin phosphate and doxorubicin-phosphate to toxic dephosphorylated compounds; fungal (e.g. *Fusarium oxysporum*) or bacterial cytosine deaminase which will convert 5-fluorocytosine to the toxic compound 5-fluorouracil (Mullen, PNAS 89:33, 1992); carboxypeptidase G2 which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds (see generally, Vrudhula et al., *J. of Med. Chem.* 36(7):919–923, 1993; Kern et al., *Canc. Immun. Immunother.* 31(4):202–206, 1990).

Within a related aspect of the present invention, recombinant viral vectors are provided carrying a vector construct which directs the expression of a gene product that activates a compound with little or no cytotoxicity into a toxic product in the presence of a pathogenic agent, thereby affecting localized therapy to the pathogenic agent. In this case, expression of the gene product from the recombinant viral vector is limited to situations wherein an entity associated with the pathogenic agent, such as an intracellular signal identifying the pathogenic state, is present, thereby avoiding destruction of nonpathogenic cells. This cell-type specificity may also be conferred at the level of infection, by targeting recombinant virus carrying the vector to cells having or being susceptible to the pathogenic condition.

Within one aspect of this method, recombinant viral vectors are provided carrying a vector construct comprising a cytotoxic gene under the transcriptional control of an event-specific promoter, such that upon activation of the event-specific promoter the cytotoxic gene is expressed. Numerous event-specific promoters may be utilized within the context of the present invention, including for example, promoters which are activated by cellular proliferation (or are otherwise cell-cycle dependent) such as the thymidine kinase or thymidilate synthase promoters (Merrill, *Proc. Natl. Acad. Sci. USA* 86:4987–91, 1989; Deng et al., *Mol. Cell. Biol.* 9:4079–82, 1989); promoters such as the α or β interferon promoters which are activated when a cell is infected by a virus (Fan and Maniatis, *EMBO J.* 8(1) :101–110, 1989; Goodbourn et al. *Cell* 45:601–610, 1986); and promoters which are activated by the presence of hormones (e.g. estrogen response promoters; see Toohey et al., *Mol. Cell. Biol.* 6:4526–38, 1986).

Within a preferred embodiment, a recombinant viral vector (preferably, but not necessarily, a recombinant MLV retrovirus) carries a vector construct containing a cytotoxic gene expressed from an event-specific promoter, such as a cell cycle-dependent promoter (e.g., human cellular thymidine kinase or transferrin receptor promoters), which will be transcriptionally active primarily in rapidly proliferating cells, such as tumors. In this manner, rapidly replicating cells which contain factors capable of activating transcription from these promoters are preferentially destroyed by the cytotoxic agent produced by the vector construct.

Within another aspect of this method, recombinant viral vectors are provided comprising a cytotoxic gene under the transcriptional control of a tissue-specific promoter, such that upon activation of the tissue-specific promoter the cytotoxic gene is expressed. A wide variety of tissue-specific promoters may be utilized within the context of the present invention. Representative examples of such promoters include: liver-specific promoters such as phosphoenolpyruvate carboxykinase ("PEPCK") (Hatzogiou et al., *J. Biol. Chem.* 263: 17798–808, 1988; Benvenisty et al., *Proc. Natl. Acad. Sci. USA* 86:1118–22, 1989; Vaulont et al., *Mol. Cell. Bio.* 9:4409–15, 1989); B cell specific promoters such as the IgG promoter; breast carcinoma or hepatocellular carcinoma specific promoters such as Carcinoembryonic Antigen promoter (CEA) (Schrewe et al., *Mol. and Cell. Biol.* 10:2738, 1990); pancreatic acinar cell specific promoters such as the elastase promoter (Swift et al., *Genes Develop.* 3:687–96, 1989); breast epithelial specific promoters such as the casein promoter (Doppler et al., *Proc. Natl. Acad. Sci. USA* 86:104–08, 1989); erythoid specific-transcription promoters which are active in erythroid cells, such as the porphobilinogen deaminase promoter (Mignotte et al., *Proc. Natl. Acad. Sci. USA* 86:6458–52, 1990); α or β globin specific promoters (van Assendelft et al., *Cell* 56:969–77, 1989, Forrester et al., *Proc. Natl. Acad. Sci. USA* 86:5439–43, 1989); promoters which regulate skeletal muscle such as the myo-D binding site (Burden, *Nature* 341:716, 1989; Weintraub et al., *Proc. Natl. Acad. Sci. USA* 86:5434–38, 1989); promoters which are specific for β cells of the pancrease, such as the insulin promoter (Ohlsson et al., *Proc. Natl. Acad. Sci. USA* 85:4228–31, 1988; Karlsson et al., *Mol. Cell. Biol.* 9:823–27, 1989); promoters which are specific for the pituitary gland, such as the growth hormone factor promoter (Ingraham et al., *Cell* 55:519–29, 1988; Bodner et al., *Cell* 55:505–18, 1988); promoters which are specific for melanosomes, such as the tyrosine hydroxylase promoter; liver-specific promoters such as the albumin promoter and the alphafetoprotein promoter (Feuerman et al., *Mol. Cell. Biol.* 9:4204–12, 1989; Camper and Tilghman, *Genes Develop.* 3:537–46, 1989); breast carcinoma specific promoters such as the HER2/neu promoter (Tal et al., *Mol and Cell. Biol.* 7:2597, 1987); liver-specific promoters such as the alcohol dehydrogenase promoter (Felder, *Proc. Natl. Acad. Sci. USA* 86:5903–07, 1989); T-cell specific promoters such as the T-cell receptor promoter (Anderson et al., *Proc. Natl. Acad. Sci. USA* 85:3551–54, 1988; Winoto and Baltimore, *EMBO J.* 8:729–33, 1989); bone-specific promoters such as the osteocalcin promoter (Markose et al., *Proc. Natl. Acad. Sci. USA* 87:1701–1705, 1990; McDonnell et al., *Mol. Cell. Biol.* 9:3517–23, 1989; Kerner et al., *Proc. Natl. Acad. Sci. USA* 86:4455–59, 1989) the IL-2 promoter, IL-2 receptor promoter, the whey (wap) promoter, and the MHC Class II promoter.

A variety of other elements which control gene expression may also be utilized within the context of the present invention, including for example locus-defining elements such as the β-globin gene and the T cell marker CD2. In addition, elements which control expression at the level of splicing and nuclear export are the β-globin intron sequences, the rev and rre elements in HIV–1, and the CTE element in the D-type masonpfizer monkey retrovirus.

Within preferred embodiments of the invention, the gene producing the cytotoxic agent is under control of a tissue-specific promoter, where the tissue specificity corresponds to the tissue of tumor origin. Since the viral vector preferentially integrates into the genome of replicating cells (for example, normal liver cells are not replicating, while those of a hepatocarcinoma are), these two levels of specificity (viral integration/replication and tissue-specific transcriptional regulation) lead to preferential killing of tumor cells.

Within yet another related aspect of the present invention, viral vectors are provided carrying a vector construct comprising a cytotoxic gene under the transcriptional control of both an event-specific promoter and a tissue-specific promoter, such that the cytotoxic gene is maximally expressed only upon activation of both the event-specific promoter and the tissue-specific promoter. In particular, by utilizing such vectors, the cytotoxic gene product is expressed only in cell types satisfying both criteria (e.g., in the example above, combined promoter elements are functional only in rapidly dividing liver cells). Within preferred embodiments of the invention, the number of transcriptional promoter elements may also be increased, in order to improve the stringency of cell-type specificity.

Transcriptional promoter/enhancer elements as discussed above need not necessarily be present as an internal promoter (lying between the viral LTRs for retroviruses), but may be added to or replace the transcriptional control elements in the viral LTRs which are themselves transcriptional promoters, such that condition-specific (i.e., event or tissue specific) transcriptional expression will occur directly from the modified viral LTR. In this case, either the condition for maximal expression will need to be mimicked in retroviral packaging cell lines (e.g., by altering growth conditions, supplying necessary transregulators of expression or using the appropriate cell line as a parent for a packaging line), or the LTR modification is limited to the 3' LTR U3 region, to obtain maximal recombinant viral titres. In the latter case, after one round of infection/integration, the 3' LTR U3 is now also the 5' LTR U3, giving the desired tissue-specific expression. Similarly, for other viral vectors, the promoters may be exogenous, or hybrids with normal viral promoter elements.

A wide variety of cytotoxic genes may be utilized within the context of the present invention. Representative examples include proteins such as ricin (Lamb et al., *Eur. J.*

Biochem. 148:265–270, 1985), abrin (Wood et al., *Eur. J. Biochem.* 198:723–732, 1991; Evensen, et al., *J. of Biol. Chem.* 266:6848–6852, 1991: Collins et al.,*J. of Biol. Chem.* 265:8665–8669, 1990; Chen et al., *Fed. of Eur. Biochem Soc.* 309:115–118, 1992), diphtheria toxin (Tweten et al., *J. Biol. Chem.* 260:10392–10394, 1985), cholera toxin (Mekalanos et al., *Nature* 306:551–557, 1983; Sanchez & Holmgren, *PNAS* 86:481–485, 1989), gelonin (Stirpe et al., *J. Biol. Chem.* 255:6947–6953, 1980), pokeweed antiviral protein (Irvin, *Pharmac. Ther.* 21:371–387, 1983), antiviral protein (Barbieri et al., *Biochem. J.* 203:55–59, 1982; Irvin et al., *Arch. Biochem. & Biophys.* 200:418–425, 1980; Irvin, *Arch. Biochem. & Biophys.* 169:522–528, 1975), tritin, Shigella toxin (Calderwood et al., *PNAS* 84:4364–4368, 1987; Jackson et al., *Microb. Path.* 2:147–153, 1987), and Pseudomonas exotoxin A 15 (Carroll and Collier, *J. Biol. Chem.* 262:8707–8711, 1987), herpes simplex virus thymidine kinase (HSVTK) (Field et al., *J. Gen. Virol.* 49:115–124, 1980), and *E. coli.* guanine phosphoribosyl transferase.

Within other embodiments of the invention, the cytotoxic gene may be an antisense sequence which inhibits, for example, tumor cell growth, viral replication, or a genetic disease by preventing the cellular synthesis of critical proteins needed for cell growth. Examples of such antisense sequences include antisense thymidine kinase, antisense dihydrofolate reductase (Maher and Dolnick, *Arch. Biochem. & Biophys.* 253:214–220, 1987; Bzik et al., *PNAS* 84:8360–8364, 1987), antisense HER2 (Coussens et al., *Science* 230:1132–1139, 1985), antisense ABL (Fainstein, et al., *Oncogene* 4:1477–25 1481, 1989), antisense Myc (Stanton et al., *Nature* 310:423–425, 1984) and antisense ras, as well as antisense sequences which block any of the enzymes in the nucleotide biosynthetic pathway. In addition, cytotoxic genes may encode tumor proliferation inhibitors such as p53, retinoblastoma (Rb), and MCC and APC for colorectal carcinoma.

Within a further embodiment of the invention antisense RNA may be utilized as a cytotoxic gene in order to induce a potent Class I restricted response. Briefly, in addition to binding RNA and thereby preventing translation of a specific mRNA, high levels of specific antisense sequences may be utilized to induce the increased expression of interferons (including gamma-interferon), due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA Antisense RNA which forms a mismatch with actin RNA is particularly preferred.

Within other aspects of the invention, recombinant viral vectors are provided carrying a vector construct which directs the expression of a gene product that activates a compound with little or no cytotoxicity into a toxic product. Within preferred embodiments of the invention, the recombinant viral vectors direct the expression of a gene product that activates a compound with little or no cytotoxicity into a toxic product in the presence of a pathogenic agent, thereby affecting localized therapy to the pathogenic agent.

For example, within one embodiment of the invention, the recombinant viral vector carries a vector construct which directs the expression of the herpes simplex virus thymidine kinase ("HSVTK") gene downstream, and under the transcriptional control of an HIV promoter (which is known to be transcriptionally silent except when activated by HIV tat protein). Briefly, expression of the tat gene product in human cells infected with HIV and carrying the vector construct causes increased production of HSVTK. The cells (either in vitro or in vivo) are then exposed to a drug such as ganciclovir, acyclovir or its analogues (FIAU, FIAC, DHPG). As noted above, these drugs are known to be phosphorylated by HSVTK (but not by cellular thymidine kinase) to their corresponding active nucleotide triphosphate forms. Acyclovir and FIAU triphosphates inhibit cellular polymerases in general, leading to the specific destruction of cells expressing HSVTK in transgenic mice (see Borrelli et al., *Proc. Nat. Acad. Sci. USA* 85:7572, 1988). Those cells containing the recombinant vector and expressing HIV tat protein are selectively killed by the presence of a specific dose of these drugs.

Figure 17:
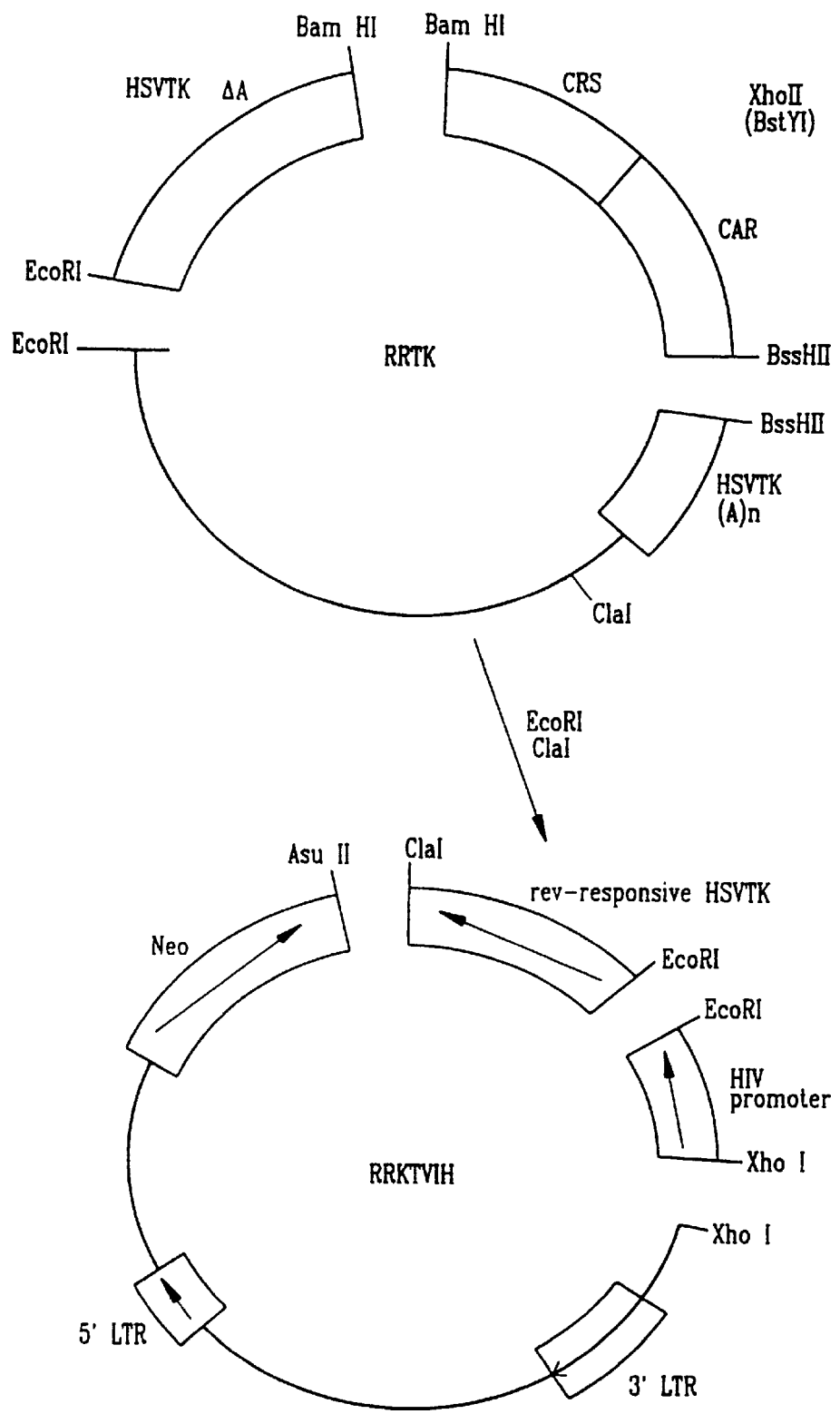
FIG. 17 is a schematic illustration of pRRKTVIH.

Within one embodiment of the invention, expression of the conditionally lethal HSVTK gene may be made even more HIV-specific by including cis-acting elements in the transcript ("CRS/CAR"), which require an additional HIV gene product, rev, for optimal activity (Rosen et al., *Proc. Natl. Acad. Sci. USA* 85:2071, 1988). Such a tat- and rev-responsive vector (RRKTVIH) has been constructed (see FIG. 17) and amphotropic virus has been generated. More generally, cis elements present in mRNAs have been shown in some cases to regulate mRNA stability or translatability. Sequences of this type (i.e., post-transcriptional regulation of gene expression) may be used for event- or tissue-specific regulation of vector gene expression. In addition, multimerization of these sequences (i.e., rev-responsive "CRS/CAR" or tat-responsive "TAR" elements for HIV) may be utilized in order to generate even greater specificity.

It should be noted that all these kinds of conditional activation of an inactive precursor into an active product in cells may also be achieved using other viral vectors such as adeno-associated viral vectors, including those with a shorter term effect, e.g., adenovirus vectors and others mentioned below. Such vectors are capable of efficiently entering cells and expressing proteins encoded by the vector over a period of time from a couple of days to a month or so. This period of time should be sufficient to allow killing of cells which are infected by both HIV and the recombinant virus, leading to HIV dependent activation of expression of a gene carried by the recombinant virus. This gene expression would then allow conversion of an inactive precursor into an active (e.g., lethal) product. In addition, physical methods of gene transfer may be utilized if they are sufficiently efficient.

In a manner similar to the preceding embodiment, vector constructs may be generated which carry a gene for phosphorylation, phosphoribosylation, ribosylation, or other metabolism of a purine- or pyrimidine-based drug. Such genes may have no equivalent in mammalian cells, and might come from organisms such as a virus, bacterium, fungus, or protozoan. Representative examples include: *E. coli* guanine phosphoribosyl transferase ("gpt") gene product, which converts thioxanthine into thioxanthine monophosphate (see Besnard et al., *Mol. Cell. Biol.* 7:4139–4141, 1987); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase which will convert 5-fluorocytosine to the toxic compound 5-fluorouracil (Mullen, *PNAS* 89:33, 1992); carboxypeptidase G2 which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds. Conditionally lethal gene products of this type have potential application to many presently known purine- or pyrimidine-based anticancer drugs, which often require intracellular ribosylation or phosphorylation in order to become effective cytotoxic agents. The conditionally lethal gene product could also metabolize a nontoxic drug, which is not a purine or pyrimidine analogue, to a cytotoxic form (see Searle et al., *Brit. J. Cancer* 53:377–384, 1986).

Mammalian viruses in general tend to have "immediate early" genes which are necessary for subsequent transcriptional activation from other viral promoter elements. Gene products of this nature are excellent candidates for intracellular signals (or "identifying agents") of viral infection. Thus, conditionally lethal genes from transcriptional promoter elements responsive to these viral "immediate early" gene products could specifically kill cells infected with any particular virus. Additionally, since the human α and β interferon promoter elements are transcriptionally activated in response to infection by a wide variety of nonrelated viruses, the introduction of vectors expressing a conditionally lethal gene product like HSVTK, for example, from these viral-responsive elements (VRE) could result in the destruction of cells infected with a variety of different viruses.

Within other aspects of the invention, recombinant viral vectors are provided which carry a gene specifying a product which is not in itself toxic, but when processed or modified by a protein, such as a protease specific to a viral or other pathogen, is converted into a toxic form. For example, the recombinant retrovirus could carry a gene encoding a proprotein for ricin A chain, which becomes toxic upon processing by the HIV protease. More specifically, a synthetic inactive proprotein form of the toxic ricin or diphtheria A chains could be cleaved to the active form by arranging for the HIV virally encoded protease to recognize and cleave off an appropriate "pro" element.

Within yet another aspect of the invention, viral vectors are provided which express a "reporting product" on the surface of the target cells in response to the presence of an identifying agent in the cells (such as HIV tat protein). This surface protein can be recognized by a cytotoxic agent, such as antibodies for the reporting protein, or by cytotoxic T-cells. In a similar manner, such a system can be used as a detection system to simply identify those cells having a particular gene which expresses an identifying protein, such as the HIV tat gene.

Within other aspects of the present invention, recombinant viral vectors are provided which direct the expression of a vector construct which encodes a ribozyme which will cleave and inactivate RNA molecules essential for viability of the vector infected cell. By making ribozyme production dependent on an intracellular signal corresponding to the pathogenic state, such as HIV tat, toxicity is specific to the pathogenic state.

Generation of Recombinant Viral Vectors

As noted above, the present invention provides compositions and methods comprising recombinant viral vectors. Particularly preferred recombinant viral vectors for use within the present invention include recombinant retroviral vectors and recombinant adenovirus vectors. The construction of recombinant retroviral vectors is described in greater detail in an application entitled "Recombinant Retroviruses" (U.S. Ser. No. 07/586,603, filed Sep. 21, 1990, now abandoned, which is hereby incorporated by reference in its entirety). These recombinant retroviral vectors may be used to generate transduction competent retroviral vector particles by introducing them into appropriate packaging cell lines (see U.S. Ser. No. 07/800,921, which is hereby incorporated by reference in its entirety). Similarly, adenovirus vectors may also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282.

In particular, proceeding in a 5' to 3' direction, an adenovirus (Ad) genome, which is a DNA based genome, has four structural units designated as early (E) regions 1–4, i.e., E1, E2, E3 and E4, and five late (L) regions designated as L1 through L5. Berkner at 616. The genome is capped by an inverted terminal repeat (ITR) sequence of approximately 100–165 bp, depending upon stereotype. Berkner at 617.

The E1 region is divided into two subregions, an E1a region and an E1b region. Berkner at 616. The E1a region contains the major transcriptional activators, such as the major late promoter (MLP). Id. at 616. The E1a region is also involved in transcriptional transactivation of viral and cellular genes as well as transcriptional repression of other sequences. Id. The E1b region is involved in protecting DNA sequences during viral infection. Id. Mutations in E1b sequences exhibit diminished late viral mRNA accumulations as well as impairment in blocking host cellular transport normally observed late in adenovirus infection. Id. at 616–617.

The combined E1a and E1b subregions (i.e., the E1 region) represent the only adenovirus sequences required for cellular transformation. Berkner at 616. The E2 region encodes proteins required for viral replication. Id. at 617. The E3 region is totally dispensable for growth in vitro and is involved in suppressing cellular immunity in vivo. Id. The E4 region plays a role in viral DNA replication, late mRNA synthesis, host cell protein synthesis shut off and viral assembly. Id.

At least part of the ITR is required for replication. Berkner at 617 citing Bernstein et al., "Template Requirements for in vivo Replication of Adenovirus DNA," *Mol. Cell. Biol.*, 6:2115–2124 (1986); Hay et al., "Replication of Adenoviruses Minichromosomes," *J. Mol. Biol.*, 175:493–510 (1984); Hay, et al., "The Origin of Adenovirus DNA Replication: Minimal DNA Sequence Requirement In vivo," *EMBO J.* 4:421–426 (1985); and Hay et al., "Viable Viruses With Deletions in The Left Inverted Terminal Repeat Define the Adenovirus Origin Of DNA Replication," *J. Gen. Virol.*, 67:321–332 (1986). The ITR sequences alone are not sufficient for replication in human cells. Berkner at 617.

There are forty-one serotypes of adenovirus. Berkner at 618. Of these, extensive genetic and biochemical characterization have been performed on Ad2 and Ad5. Id. at 618. Based upon these studies, it is theoretically possible to substitute up to 7.5 kb of heterologous sequences into an adenovirus, generating a viable, conditional, helper-independent Ad vector. Id. at 618. This result is due to the large genome size, to deletions which can be made in the dispensable E3 region and in E1 using complementation on 293 cells, and to the fact that Ad recombinants of 106 $m\mu$ (i.e., 38 kb) in size can be packaged into virions. Id. at 618–620. As of the time of Berkner (1988), the longest reported insert contained in a viable Ad recombinant was 5 kb. Berkner at 620 citing Ghosh-Choudhury, "Protein IX, a Minor Component of the Human Adenovirus Capsid, Is Essential For the Packaging of Full Length Genomes," *EMBO J.* 6:1733–1739 (1987).

The advantages of adenoviruses as potential vectors for human gene therapy are as follows: (i) recombination is rare;

(ii) there were no known associations of human malignancies with adenoviral infections despite common human infection with adenoviruses; (iii) the virus genome (which is a linear, double stranded piece of DNA) can be manipulated to accommodate foreign genes of up to 7.0 to 7.5 Kb in length and vaccine. Rosenfield, "Adenovirus—Mediated Transfer of a Recombinant α1-antitrypsin Gene to the Lung Epithelium In Vivo," *Science*, 252: 431–434 (19, 1991) at 431, col. 2.

Efficient transformation of host cells has been observed for recombinant adenoviruses having substitutions in the E1 region by DNA sequences encoding neomycin resistance or the SV40 early region (i.e., T antigen). Berkner at 623–624 citing van Doren, et al., "Efficient Transformation of Human Fibroblasts by Adenovirus-simean Virus 40 Recombinants," *Mol. Cell. Biol.*, 4:1653–1656 (1984) and van Doren, et al., "Infection of Eukaryotic cells by helper-independent recombinant adenoviruses: Early region 1 is not obligatory for integration of viral DNA, *J. Virol.* 50:606–614 (1984).

Similarly, Rosenfield (1991) discloses a recombinant adenovirus having the gene encoding human α1-antitrypsin successfully infected rat lung epithelium and expressed the α1-antitrypsin gene. The recombinant adenovirus of Rosenfield had a deletion in the E3 region (that permits encapsidation of the recombinant genome) and a deletion of portions of the E1a coding sequence (that impairs viral replication) but contains an insert of a α1-antitrypsin expression cassette. See Rosenfield at FIG. 1. The human α1-antitrypsin expression cassette consisted of the 5' ITR and origin of replication followed by the encapsidation signal, the E1a enhancer, the Ad2 major late promoter (MLP), the Ad2 tripartite leaders 1–3, the α1-antitrypsin gene and an SV40 polyadenylation signal. Id. In Rosenfield, the above described vector construct was used to successfully infect and express human $\alpha_1$-antitrypsin in rat lungs in vitro and in vivo. In addition, other cells infected by recombinant adenoviruses having E1 deletions include human fibroblasts [van Doren, *J. Virology*, 50:606–614 (1984)]; and tk$^-$ mouse cells transformed to a tk$^+$ phenotype by an E1 region-deleted Ad recombinant substituted in the E3 region by the tk gene. See Berkner at 624, col. 1 citing Haj-Ahmad, et al., *J. Virol.*, 57:267–274 (1986).

Adenoviral transformants having E3 deletions replaced with genomic inserts are also useful in transforming eukaryotic cells. See Berkner at page 642, citing to Ghosh-Choudhury, *Biochem. Biophys. Res. Scam.*, 147:964–973 (1987) for transforming CHO cells to express DHFR; and citing to Karlson, *EMBO J.* 5:2377–2385 (1986) for using Ad transformants to transfer Neo$^R$ to hematopoietic cells. Karlson reflects the utility of adenoviruses in delivering two genes, e.g., the Neo$^R$ inserted in the E3 deletion and a β-globin or α–β hybrid globin gene in the E1 region, which genes were expressed in a tissue-specific manner. See Berkner at 624, col. 1 discussing Karlson.

The transformation efficiency of adenoviral vectors is higher than obtained using DNA transfection, but significantly less than obtained with retroviruses. Berkner at 624, col. 1. Adenoviruses offer certain advantages over retroviruses, including no rearrangement of intron-containing genes or inhibition due to polyadenylation signals, as observed with the latter. Id. at cols. 1–2.

For Ad transformants having gene inserts that are expressed during the late phases of the adenoviral infection (e.g., E3 or later), the adenoviral tripartite leader sequence is required to obtain any translation. Berkner at 624, col. 3. Seventy fold differences in translation are observed between constructs having a small portion of the tripartite leader sequence versus the same gene proceeded by almost all of the tripartite leader sequence. Berkner at 624, col. 3. Thus, adenoviral vectors may be readily prepared and utilized given the above described disclosure and the knowledge in the art.

Vector constructs of the present invention may also be utilized with other viral vectors, including for example poliovirus (Evans et al., *Nature* 339:385–388, 1989, and Sabin, *J. of Biol. Standardization* 1:115–118, 1973); rhinovirus (Arnold, *J. Cell. Biochem.* L401–405, 1990); pox viruses, such as canary pox virus or vaccinia virus (Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112 and 4,769,330; WO 89/01973); SV40 (Mulligan et al., *Nature* 277:108–114, 1979); influenza virus (Luytjes et al., *Cell* 59:1107–1113, 1989; McMicheal et al., *The New England Journal of Medicine* 309:13–17, 1983; and Yap et al., *Nature* 273:238–239, 1978); parovirus such as adeno-associated virus (Samulski et al., *Journal of Virology* 63:3822–3828, 1989, and Mendelson et al., *Virology* 166:154–165, 1988); herpes (Kit, *Adv. Exp. Med. Biol.* 215:219–236, 1989); SV40; HIV; measles (EP 0 440,219); corona virus and Sindbis virus (Xiong et al., *Science* 234:1188–1191, 1989; U.S. Pat. Nos. 5,091,309 and 5,217,879).

Within other aspects of the present invention, the vector contructs described above may also direct the expression of additional non-vector derived genes. Within one embodiment, the non-vector derived gene encodes a protein, such as an immune accessory molecule. Representative examples of immune accessory molecules include IL-1, IL-2, IL-3, IL-4, IL-5, IL-6, IL-7 (U.S. Pat. No. 4,965,195), IL-8, IL-9, IL-10, IL-11, IL-12, B7, B7-2, GM-CSF, CD3 (Krissanen et al., *Immunogenetics* 26:258–266, 1987), ICAM-1 (Simmons et al., *Nature* 331:624–627, 1988), β-microglobulin (Parnes et al., *PNAS* 78:2253–2257, 1981), LFA3 (Wallner et al., *J. Exp. Med.* 166(4):923–932, 1987), HLA Class I, and HLA Class II molecules. Within one preferred embodiment, the non-vector derived gene encodes gamma-interferon.

Sequences which encode the above-described non-vector derived genes (e.g., immune accessory molecules), as well as the cytotoxic genes discussed above, may be readily obtained from a variety of sources. For example, plasmids which contain sequences that encode immune accessory molecules may be obtained from a depository such as the American Type Culture Collection (ATCC, Rockville, Md.), or from commercial sources such as British Bio-Technology Limited (Cowley, Oxford England). Representative sources sequences which encode the above-noted anti-tumor agents include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No. 67024 (which contains a sequence which encodes Interleukin-1), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6). It will be evident to one of skill in the art that one may utilize either the entire sequence of the protein, or an appropriate portion thereof which encodes a protein having biological activity.

Alternatively, known cDNA sequences which encode cytotoxic genes or other non-vector derived genes may be obtained from cells which express or contain such sequences. Briefly, within one embodiment mRNA from a cell which expresses the gene of interest is reverse transcribed with reverse transcriptase using oligo dT or random primers. The single stranded cDNA may then be amplified by PCR (see U.S. Pat. Nos. 4,683,202, 4,683,195 and 4,800,159. See also PCR Technology: Principles and Applications for DNA Amplification, Erlich (ed.), Stockton Press, 1989 all of which are incorporated by reference herein in their entirety) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Sequences which encode the above-described genes may also be synthesized, for example, on an Applied Biosystems Inc. DNA synthesizer (e.g., ABI DNA synthesizer model 392 (Foster City, Calif.)).

Pharmaceutical Composition

Within another aspect of the invention, pharmaceutical compositions are provided, comprising a recombinant viral vector as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for either surface administration, injection, oral, or rectal administration.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2, and 150 mM NaCl. In this case, since the recombinant vector represents approximately 1 mg of material, it may be less than 1% of high molecular weight material, and less than 1/100,000 of the total material (including water). This composition is stable at −70 C for at least six months.

Pharmaceutical compositions of the present invention may also additionally include factors which stimulate cell division, and hence, uptake and incorporation of a recombinant retroviral vector. Representative examples include Melanocyte Stimulating Hormone (MSH), for melanomas or epidermal growth factor for breast or other epithelial carcinomas.

Particularly preferred methods and compositions for preserving recombinant viruses are described in U.S. applications entitled "Methods for Preserving Recombinant Viruses" (U.S. Ser. No. 08/135,938, filed Oct. 12, 1993, now abandoned, and U.S. Ser. No. 08/153,342, filed Nov. 15, 1993, now abandoned, which are incorporated herein by reference in their entirety).

Methods of Administration

Within other aspects of the present invention, methods are provided for inhibiting or destroying pathogenic agents in a warm-blooded animal, comprising administering to a warm-blooded animal a recombinant viral vector as described above, such that the pathogenic agent is inhibited or destroyed. Within various embodiments of the invention, recombinant viral vectors may be administered in vivo, or ex vivo as described in greater detail below. Alternatively, the cytotoxic genes, gene products, vector constructs or viral vectors of the present invention may also be administered to a patient by a variety of other methods. Representative examples include transfection by various physical methods, such as lipofection (Felgner et al., *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991); liposomes of several types (see e.g., Wang et al., *PNAS* 84:7851–7855, 1987); $CaPO_4$ (Dubensky et al., *PNAS* 81:7529–7533, 1984); DNA ligand (Wu et al, *J. of Biol. Chem.* 264:16985–16987, 1989); administration of nucleic acids alone (WO 90/11092); or administration of DNA linked to killed adenovirus (Curiel et al., *Hum. Gene Ther.* 3: 147–154, 1992).

Within one embodiment of the invention, a patient suffering from a non-metastatic, but otherwise untreatable tumor such as glioblastoma, astrocytoma, or other brain tumor, may be treated by injecting purified, concentrated HSVTK vector directly into the tumor. The vector is preferentially integrated and expressed in tumor cells since only growing cells are transducible with retroviral vectors. The vector may express HSVTK in an unregulated fashion or, to promote greater tumor specificity, may express HSVTK from a tissue or event specific promoter which is preferentially expressed in the tumor. For instance, a vector which expresses HSVTK from the CEA promoter may be utilized to treat breast or liver carcinomas. Multiple injections (>10) of vector (approximately 1 ml with a titer of $1 \times 10^7 – 1 \times 10^8$ cfu) can be delivered over an extended period of time (>3 months) since the purified vector contains non-immunogenic quantities of protein (<1 mg protein per $1 \times 10^7$ cfu). Thus, injections may continue until a large fraction of the tumor cells have become transduced. Vector may be delivered stereotactically before or after debulking surgery or chemotherapy. After in vivo transduction has occurred, the transduced tumor cells may be eliminated by treating the patient with pro-drugs which are activated by HSVTK, such as acyclovir or ganiclovir.

Within another aspect of the present invention, methods are provided for destroying pathogenic agents in a warm blooded animal, comprising administering to the animal Vector Producing Cells (also termed "VCLs" or "producer cells"), in order to destroy the pathogenic agent. Within a preferred embodiment, the VCLs may be injected directly into a tumor, thereby allowing for the continual production of retroviral vector in vivo and an increase in the efficiency of transduction.

One difficulty with the direct injection of VCLs however, is that in certain instances a very potent immune response may result, thus making such therapy feasible for only a very short term (<2 weeks). Therefore, within preferred embodiments of the invention the immune response against VCLs may be minimized by selecting packaging cell lines made from autologous or HLA-matched human cells. In addition, in order to further limit the immune response against viral structural proteins expressed by the VCLs, the cells may be enclosed in a structure, such as a bead or a bag, which has a semi-permeable membrane, allowing vector particles to diffuse into the tumor, but preventing host immune cells from passing through the membrane and thereby generating an immune response. Methods which decrease the immune response allow additional time for in vivo transduction to occur, and thus improves the therapy. In each case, the VCL is preferably destroyed by treatment with acyclovir or ganiclovir after it has accomplished its role in the in vivo transduction of cells.

Within another embodiment of the invention, metastatic, but highly localized cancers such as ovarian, neuroblastoma and cervical carcinomas (which are metastatic, but typically remain localized to the peritoneal cavity) may be treated according to the methods of the present invention. Within this embodiment, vector or VCLs may be injected directly into the peritoneal cavity. Within a particularly preferred approach, rapidly growing tumors are preferentially transduced in vivo by a HSVTK vector, and may be subsequently destroyed by administering acyclovir or ganiclovir to the patient.

Within yet another embodiment of the invention, viral vectors or VCLs may be injected into the pleural cavity for the treatment of pleural carcinomatosis arising from lung, breast or colon carcinomas, or by intrathecal injection for the treatment of meningeal carcinomatosis.

Within another embodiment of the invention, patients with metastatic, disseminated cancer may also be treated according to the methods of the present invention. For instance, primary pancreatic carcinomas or colorectal carcinomas that have metastasized to, for example, the liver, may be injected directly with viral vector or VCL of the present invention by inserting a syringe, possibly targeted by stereotaxis, through the body wall. Tumors in the lung or colon may similarly be accessed by bronchoscopy or sigmoidoscopy, respectively. Tumor cells which have been transduced in vivo by, for example, a vector which expresses HSVTK, may then be destroyed by administration of acyclovir or ganciclovir to the patient.

Within preferred embodiments of the invention, in addition to administration of a cytotoxic gene or gene products (e.g., HSVTK) as described above, a variety of additional therapeutic compositions may be co-administered or sequentially administered to a warm-blooded animal, in order to inhibit or destroy a pathogenic agent. Such therapeutic compositions may be administered directly, or, within other embodiments, expressed from independent vector constructs. Alternatively, a single vector which directs the expression of both a cytotoxic gene or gene product, and a gene which encodes the therapeutic composition (e.g., a non-vector derived gene as discussed above) may be administered to the warm-blooded animal, in order to inhibit or destroy a pathogenic agent. Within a particularly preferred embodiment, vector or VCLs which deliver and express both the HSVTK gene and a gene coding for an immune accessory molecule, such as human γ-IFN, may be administered to the patient. In such a construct, one gene may be expressed from the vector LTR and the other may utilize an additional transcriptional promoter found between the LTRs, or may be expressed as a polycistronic mRNA, possibly utilizing an internal ribosome binding site. One example of such a provector is found in Example 10. After in vivo gene transfer, the patient's immune system is activated due to the expression of γ-IFN. After this has occurred, the overall tumor burden itself may be reduced by treating the patient with acyclovir or ganiclovir, allowing more effective immune attack of the tumor. Infiltration of the dying tumor with inflammatory cells, in turn, increases immune presentation and further improves the patient's immune response against the tumor.

In addition to cancer, as noted above the methods of the present invention may be utilized to destroy or inhibit other pathogenic agents. For example, viral vectors of the present invention may be administered to human T-cell and/or macrophage/monocyte cell lines, in order to increase their resistance to HIV in the presence of AZT or ddC, as compared to the same cells without viral vector treatment. Treatment with AZT may be at lower than normal levels to avoid toxic side effects, but still efficiently inhibit the spread of HIV.

Within a preferred embodiment of the invention, susceptible T-cells or monocytes may be targeted with vectors which carry VSV G, HIV env or hybrid env, in order to direct absorption of vector particles to $CD4^+$ cells. For example, viral vectors may be targeted by producing vector particles which will infect cells using the HIV env protein (gp120) as a receptor. Such HIV-tropic viruses may, within preferred embodiments be produced from an MLV-based packaging cell line constructed from cells which have naturally high levels of CD4 protein (for example, Sup T1 cells) and/or CD26 protein in their cell membrane, or from any cell type "engineered" to express such proteins. The resultant virions, which form by budding from the cell membrane itself, contain the CD4 (and/or CD26) proteins in their membrane. Since membranes containing CD4 (and CD26) are known to fuse with membranes carrying HIV env, these virions should fuse with cells containing HIV env and result in the specific infection of HIV-infected cells which have gp120 on their surface. Such a packaging cell line may require the presence of an MLV env protein to allow proper virion assembly and budding to result in infectious virions. If so, an MLV env which does not infect human cells (such as ecotropic env) would be used such that viral entry will occur only through the CD4 (and/or CDCC)/HIV env interaction and not through the MLV env cell receptor, which would presumably not depend upon the presence of HIV-env for infection. Alternatively, the requirement for MLV env may be satisfied by a hybrid envelope where the amino-terminal binding domain has been replaced by the amino-terminal HIV-env binding domain of CD4 and/or CD26. This inversion of the normal virus-receptor interaction can be used for all types of viruses whose corresponding cellular receptor has been identified.

As will be understood by one of ordinary skill in the art given the disclosure provided herein, any of the vector constructs described herein may be delivered not only as a viral vector, but as direct nucleic acid vectors. Such vectors may be delivered utilizing any appropriate physical method of gene transfer.

The following examples are offered by way of illustration, and not by way of limitation.

EXAMPLES

Example 1

Construction of Vectors

A Construction of Plasmids Containing Vector LTR Sequences

All of the following retroviral vectors are based on the N2 (Keller et al., *Nature* 318:149–154, 1985). Briefly, 5' and 3' Eco RI LTR fragments (2.8 and 1.0 kb, respectively) (Armentano, *J. Vir.* 61:1647, 1987; Eglitis, *Science* 230:1395, 1985) are initially subcloned into the Eco RI site of plasmids SK+ (Stratagene, San Diego, Calif.) and pUC31. pUC31 is a modification of pUC19 (Stratagene, San Diego, Calif.) carrying additional restriction sites (Xho I, Bgl II, BssH II, and Nco I) between the Eco RI and Sac I sites of the polylinker. Plasmid N2R3+/− is thereby created from ligation of the SK⁺ plasmid with the 1.0 kb 3' LTR fragment. The plasmids p31N2R5+/− and p31N2R3+/− are constructed from the ligation of pUC31 with the 2.8 kb 5' LTR and packaging signal (ψ) or the 1.0 kb 3' LTR fragment, respectively. In each case N2 refers to the vector source, R refers to the fact that the fragment is an Eco RI fragment, 5 and 3 refer to 5' or 3' LTRs, and + or − refers to the orientation of the insert (see FIGS. 1–6 for examples of LTR subclones).

In one case, a 1.2 kb Cla I/Eco RI 5' LTR and ψ fragment from N2 is subcloned into the same sites of an SK⁺ vector. This vector is designated pN2CR5. In another case, the 5' LTR containing a 6 bp deletion of the splice donor sequence (Yee et al., Cold Spring Harbor, Quantitative Biology, 51:1021, 1986) is subcloned as a 1.8 kb Eco RI fragment into pUC31. This vector is designated p31N25Δ[+], FIG. 6.

B. Construction of Plasmids Containing HSVTK and HIV Promoter

The coding region and transcriptional termination signals of HSV-1 thymidine kinase gene (HSVTK) are isolated as a 1.8 kb Bgl II/Pvu II fragment from plasmid 322TK (3.5 kb Bam HI fragment of HSV-1 (McKnight et al.) cloned into Bam HI of pBR322 (ATCC No. 31344)) and cloned into Bgl II/Sma I-digested pUC31. This construct is designated pUCTK For constructs which require deletion of the terminator signals, pUCTK is digested with Sma I and Bam HI and the 0.3 kb fragment containing the $(A)_n$ signal is removed. The remaining coding sequences and sticky-end Bam HI overhang are reconstituted with a double-stranded oligonucleotide made from the following oligomers:

5' GAG AGA TGG GGG AGG CTA ACT GAG 3' (SEQUENCE ID. NO. 1)

5' GAT CCT CAG TTA GCC TCC CCC ATC TCT C 3' (SEQUENCE ID. NO. 2)

Figure 7:
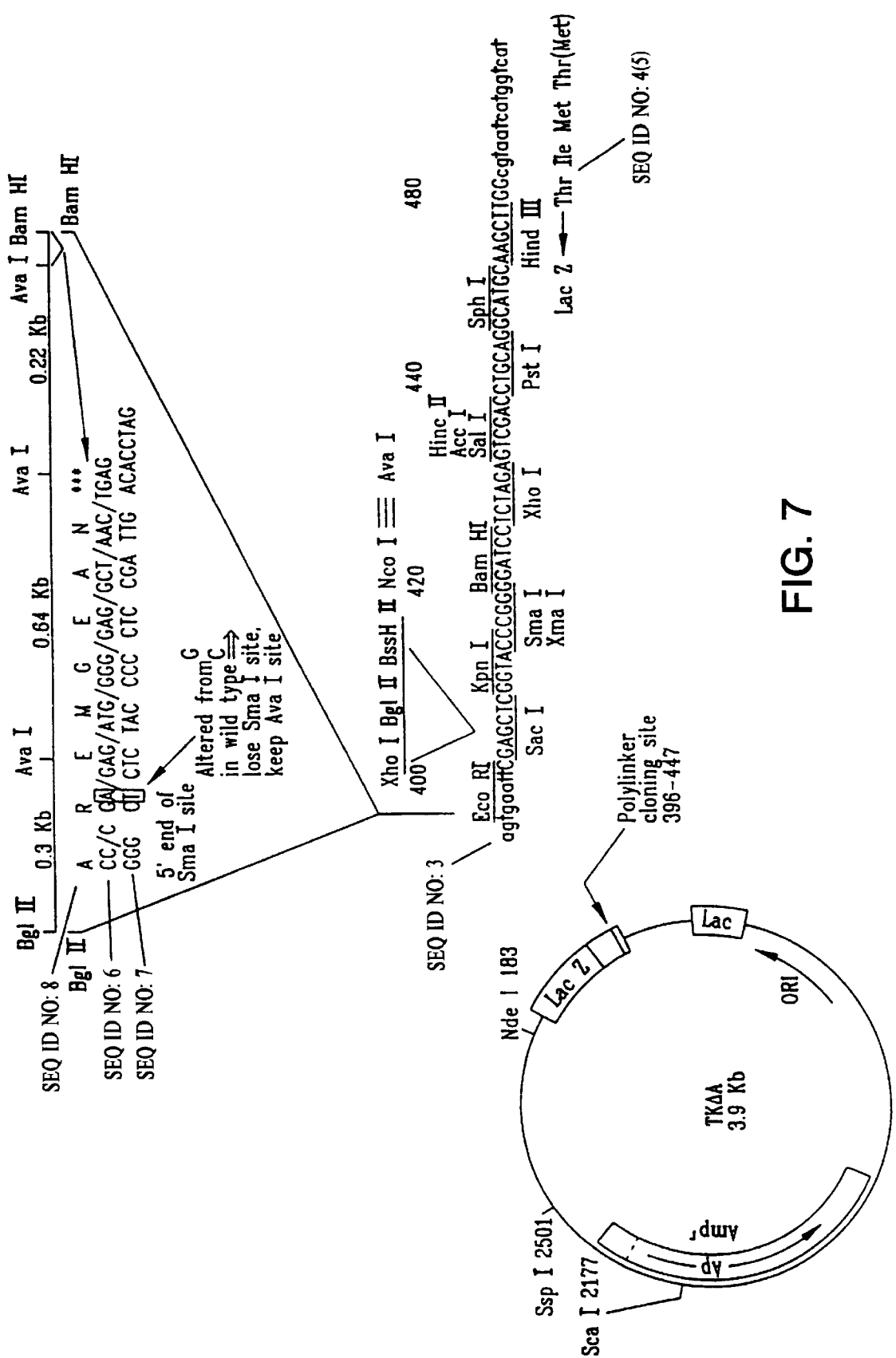
FIG. 7 is a schematic illustration of pTKΔA.

The resulting construct is designated pTK Δ A, FIG. 7.

For diagnostic purposes, the oligos are designed to destroy the Sma I site while maintaining the Ava I site without changing the translated protein.

The plasmid pPrTKΔA (FIG. 8), which contains the HSVTK promoter and coding sequence (lacking an $(A)_n$ signal), is constructed as follows.

1. pTKΔa is linearized with Bgl II treated with alkaline phosphatase, and gel purified.

Figure 8:
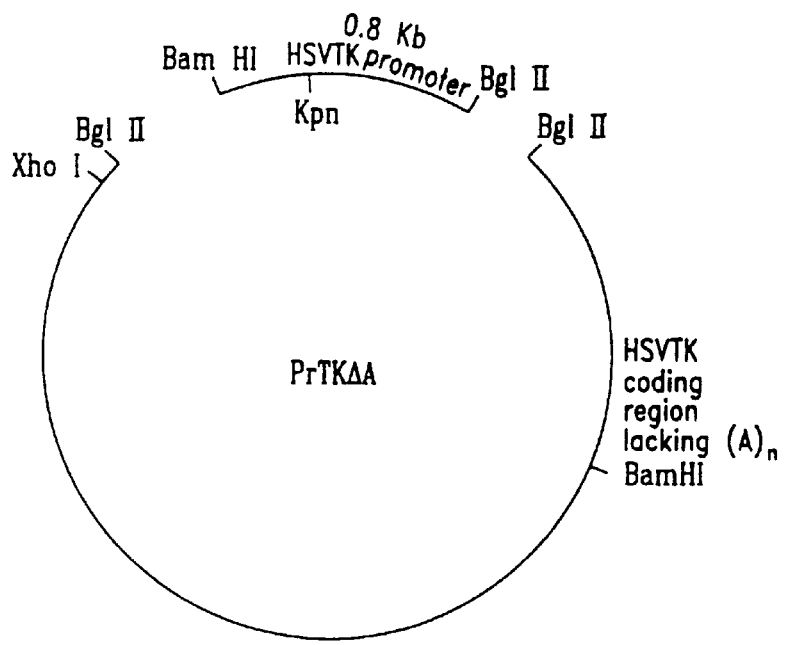
FIG. 8 is a schematic illustration of pPrTKΔA.

2. A 0.8 kg fragment contained the HSVTK transcriptional promoter is isolated as a Bam HI/Bgl II fragment from p322TK 3. Products from (1) and (2) are ligated, transformed into bacteria, and positive clones are screened for the proper orientation of the promoter region. A resultant clone is designated pPrTKΔA (FIG. 8).

The 0.6 kb HIV promoter sequences are cloned as a Dra I/Hind III fragment from pCV-1 (Arya et al., *Science* 229:69–73, 1985) into Hinc II/Hind III-cut SK⁺. The resulting construct is designated pSKHL.

C. Construction of Retroviral Provectors Expressing HSVTK from a Constitutive Promoter The retroviral provectors pTK-1, pTK-2 and pTK-3 are constructed essentially as described below.

1. The 5 kb Xho I/Hind III 5' LTR and plasmid sequences are isolated from p31N2R5(+) (FIG. 1).

2. HSVTK coding sequences lacking transcriptional termination sequences are isolated as a 1.2 kb Xho I/Bam HI fragment from pTKΔA (FIG. 2).

Figure 2:
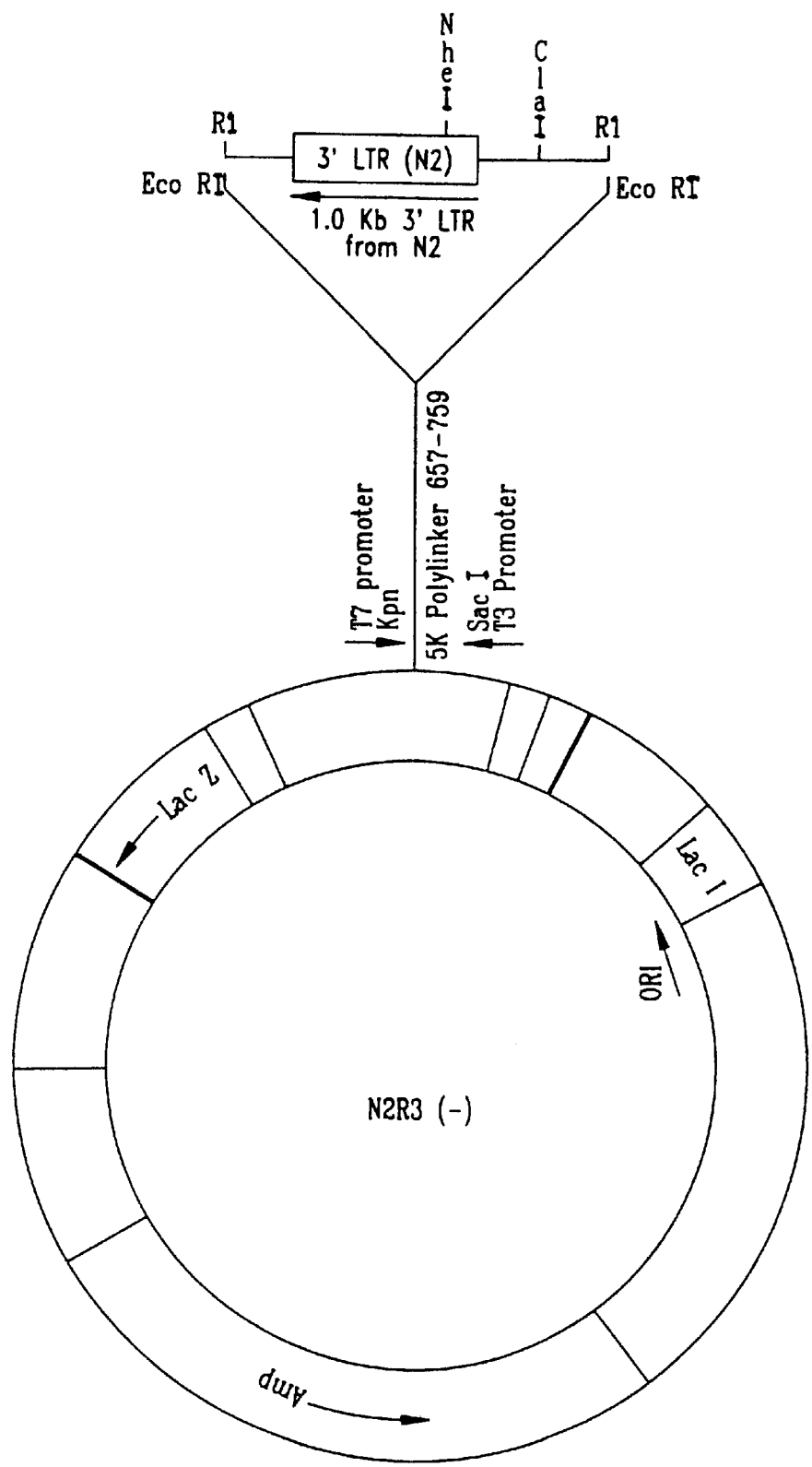
FIG. 2 is a schematic illustration of pN2R3(−).
Figure 3:
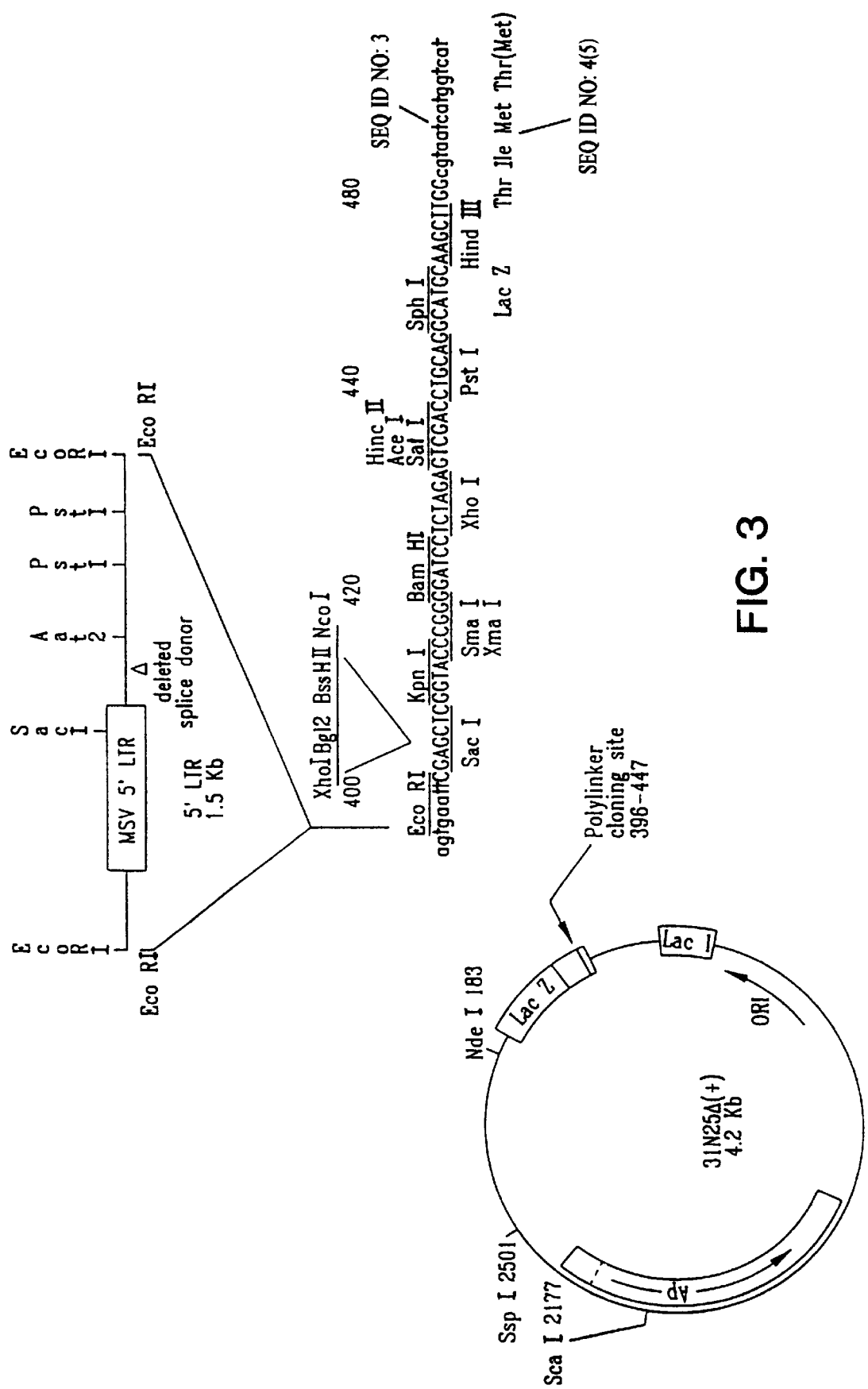
FIG. 3 is a schematic illustration of p31N25Δ(+).

3. 3' LTR sequences are isolated as a 1.0 kb Bam HI/Hind III fragment from pN2R3(−) (FIG. 2).

Figure 9:
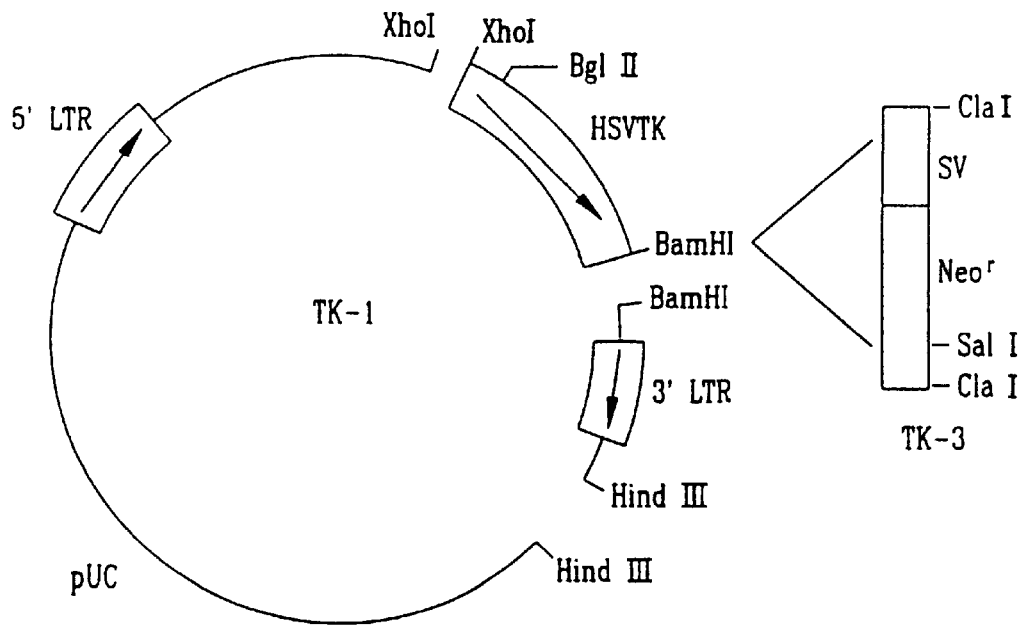
FIG. 9 is a schematic illustration of pTK−1 and pTK−3.

4. The fragments from steps 1–3 are mixed, ligated, transformed into bacteria, and individual clones identified by restriction enzyme analysis. The construct is designated TK-1 (FIG. 9).

Figure 10:
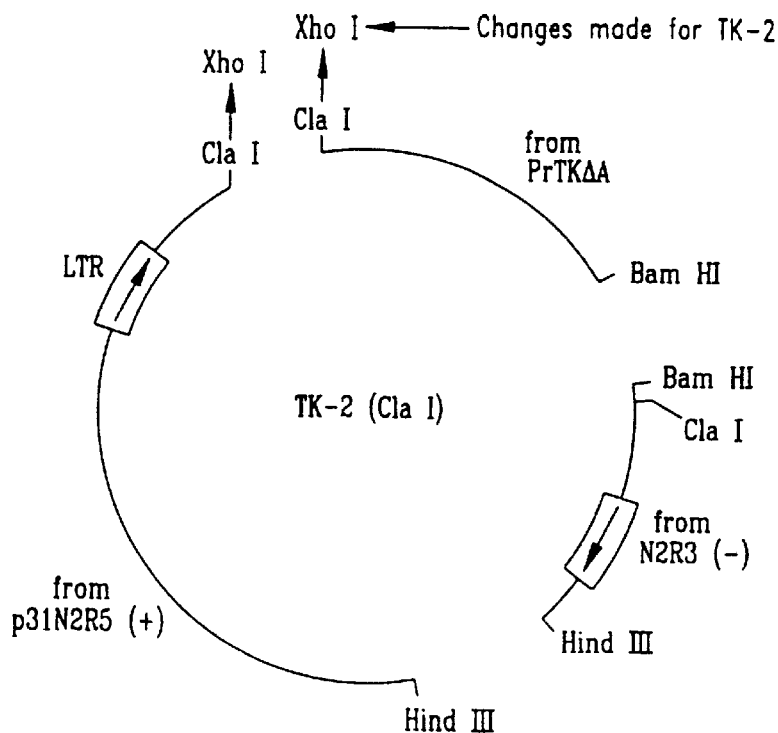
FIG. 10 is a schematic illustration of pTK2 and pTK−2 (ClaI).

5. pTK-3 is constructed by linearizing TK-1 with Bam HI, filling in the 5' overhang and blunt-end ligating a 5'-filled Cla I/Cla I fragment containing the bacterial lac UV5 promoter, SV40 early promoter, plus Tn5 Neo$^r$ gene obtained from pAFVXM retroviral vector (Krieger et al., *Cell* 39:483, 1984; St. Louis et al., *PNAS* 85:3150, 1988). Kanamycin-resistant clones are isolated and individual clones are screened for the proper orientation by restriction enzyme analysis (see FIG. 9).

pTK-2 is constructed essentially as follows (see FIG. 10):

1. The plasmid p31N2R5(+) (FIG. 1) is cut with Xho I and Hind III.

2. A 2.0 kb fragment containing the HSVTK coding sequence (lacking its $(A)_n$ sequence) and the HSVTK transcriptional promoter is isolated from Xho I/Hind III cut pPrTKΔ (FIG. 8).

3. Isolating the 3' LTR as a 1.0 kb fragment from Bam HI/Hind III cut pN2R3(−) (FIG. 2).

4. The fragments from 1, 2 and 3 above are ligated, transformed into bacteria, and amp$^r$ clones of the appropriate structure identified by restriction enzyme analysis.

These constructs are used to generate infectious recombinant vector particles in conjunction with a packaging cell line.

D. Construction of pKTVIHAX

Figure 11:
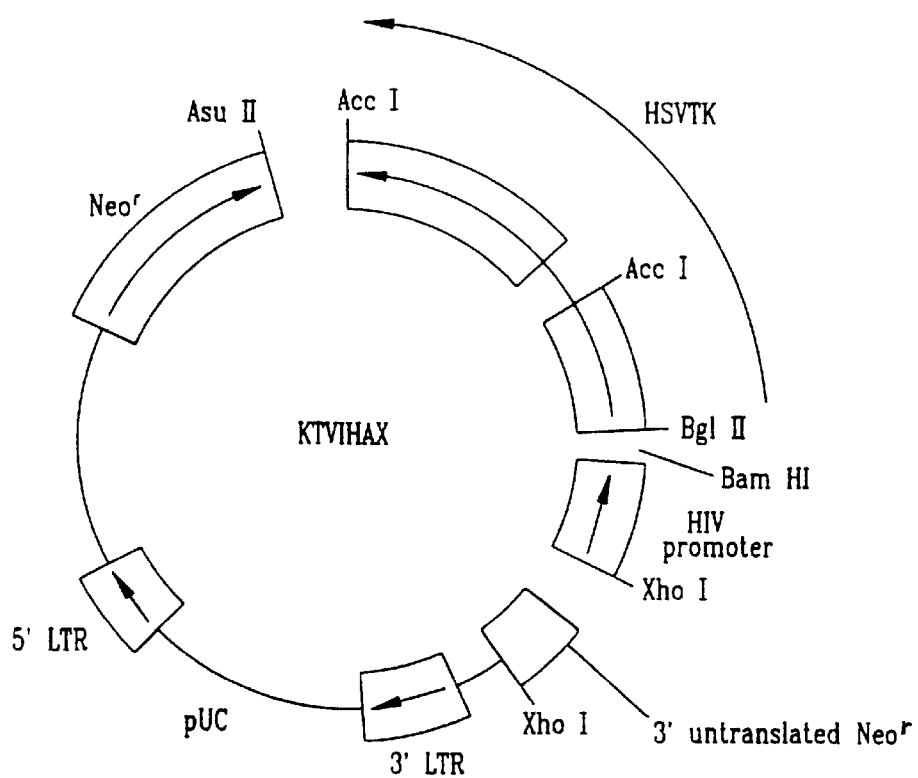
FIG. 11 is a schematic illustration of pKTVIHAX.

The retroviral vector pKTVIHAX is constructed essentially as described below (see FIG. 11).

1. The 9.2 kb Asu II/Xho I fragment is isolated from N2 vector DNA (Keller et al., *Nature* 318:149, 1985).

2. The 0.6 kb Xho I/Bam HI promoter fragment is isolated from plasmid pSKHL from Example 1B.

3. The 0.3 kb Bgl II/Acc I and 1.5 kb Acc I/Acc I fragment are purified from pUCTK from Example 1B.

4. The fragments from 1, 2, and 3 are ligated, transformed into bacteria, and appropriate ampicillin resistant clones of the given structure identified by restriction enzyme analysis.

E. Construction of pKTVIH-5 and pKTVIH5 Neo Retroviral Vectors

Figure 12:
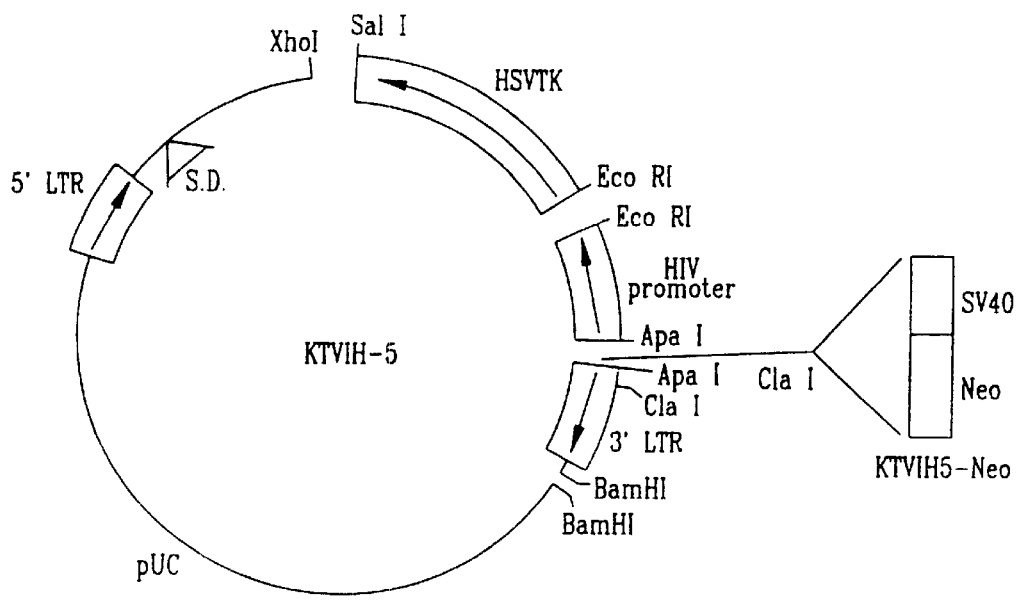
FIG. 12 is a schematic illustration of pKTVIH−5 and pKTVIH5 Neo.

The retroviral vectors pKTVIH-5 and pKTVIH5 Neo are constructed essentially as described below (see FIG. 12).

Figure 6:
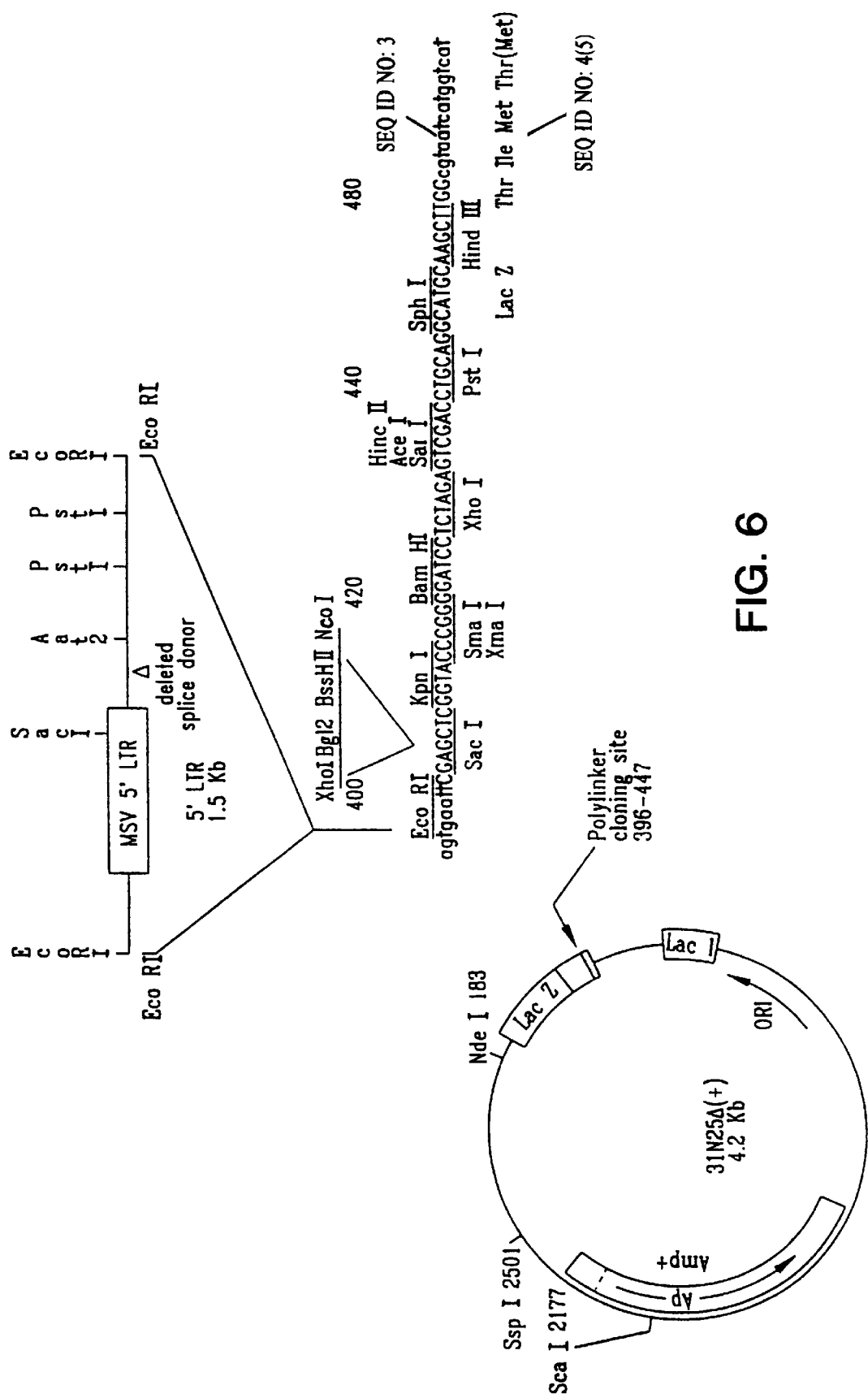
FIG. 6 is a schematic illustration of p31N25Δ(+).

1. The 5' LTR and vector fragment is isolated as a 4.5 kb Xho I/Bam HI fragment from vector p31N25Δ(+) (FIG. 6).

Figure 4:
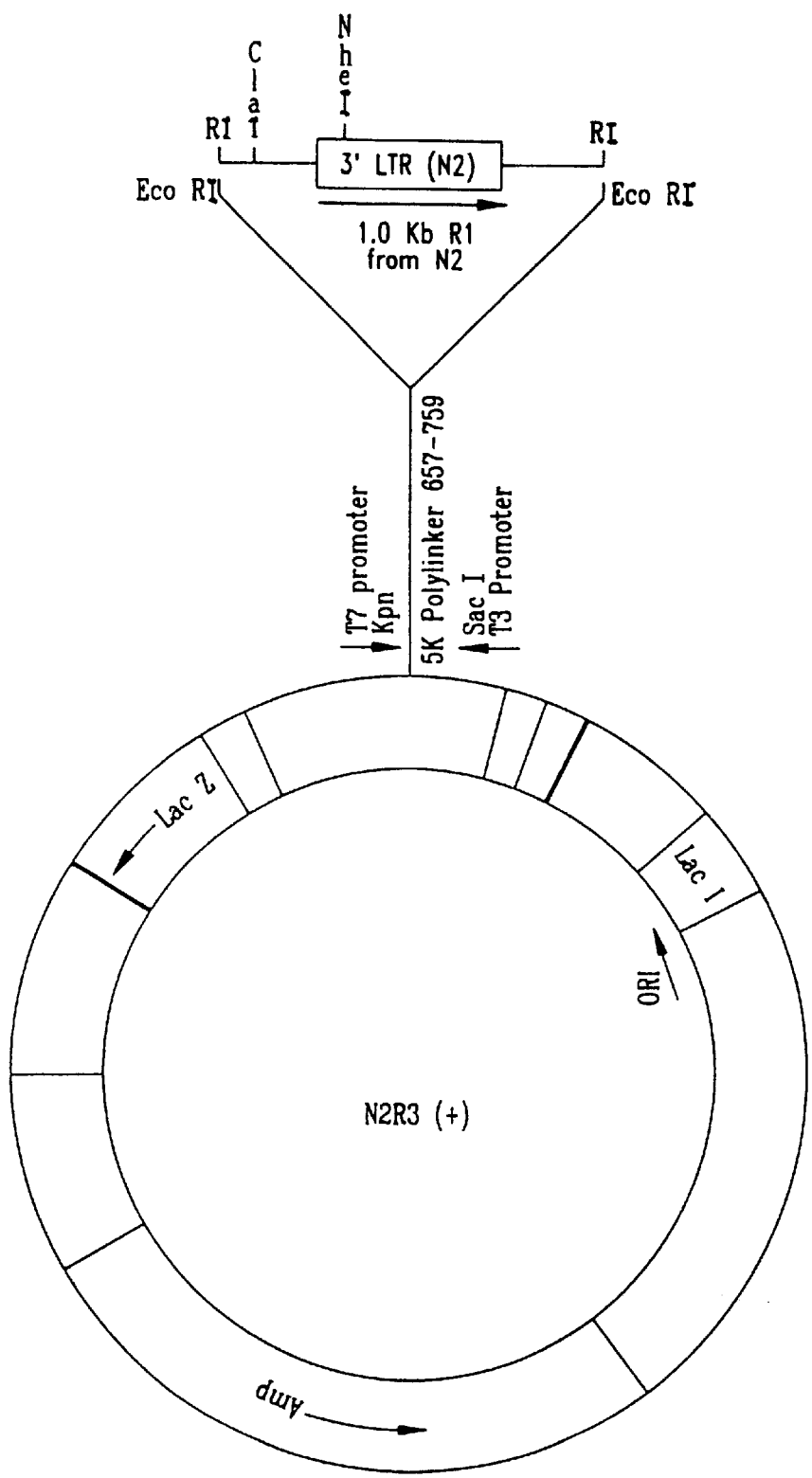
FIG. 4 is a schematic illustration of pN2R3(+).
Figure 5:
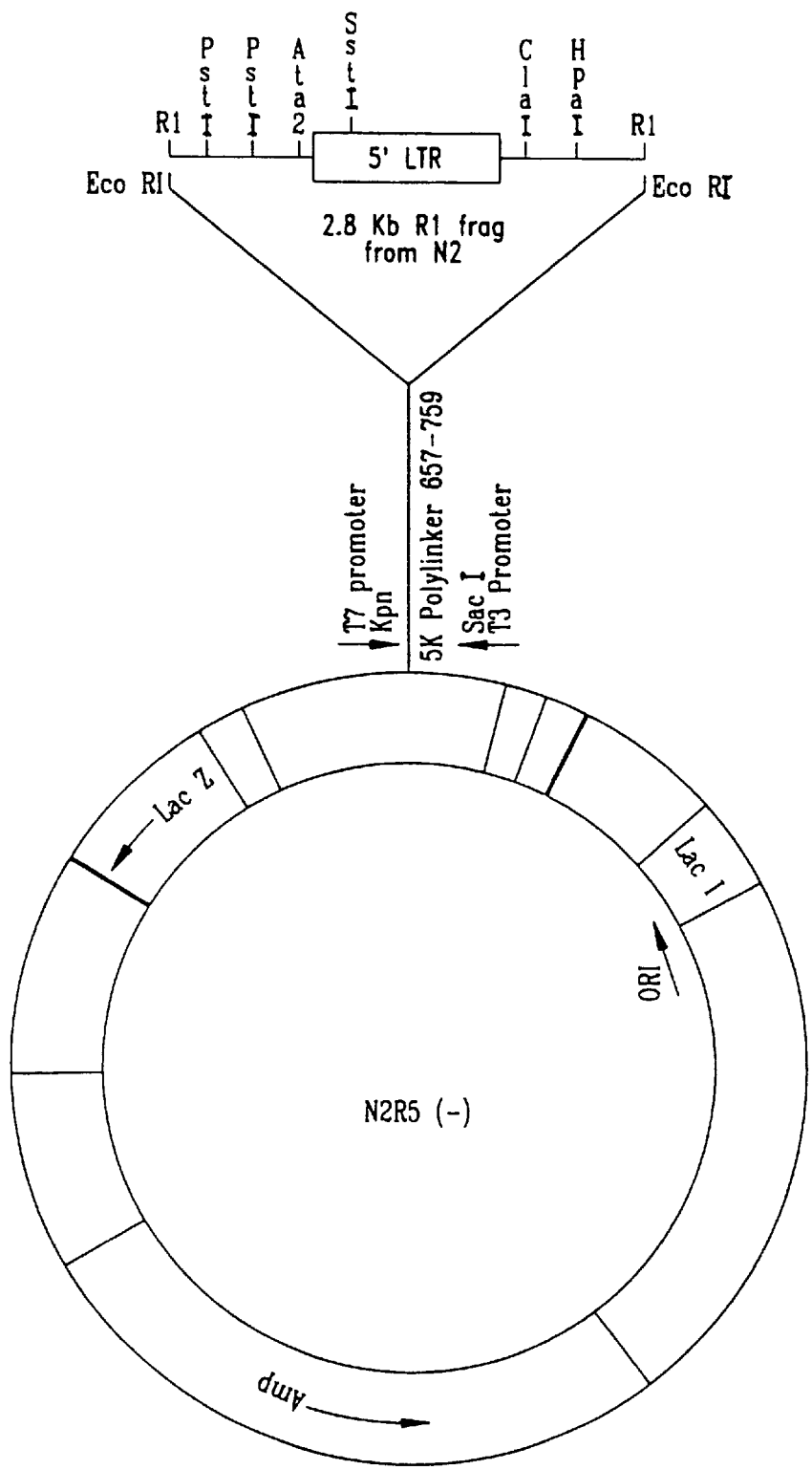
FIG. 5 is a schematic illustration of pN2R5(−).

2. The 3' LTR is isolated as a 1.0 kb Apa I/Bam HI fragment from pN2R3(+) (FIG. 4).

3. The 0.6 kb HIV promoter element is isolated from pSKHL as an Apa I/Eco RI fragment from Example 1B.

4. The HSVTK coding sequence and transcriptional termination sequences are isolated as a 1.8 kb Eco RI/Sal I fragment from pUCTK from Example 1B.

5. The fragments from 1–4 are combined, ligated, transformed into bacteria, and clones of the desired construct are identified by restriction enzyme analysis. The construct is designated pKTVIH-5, FIG. 12.

6. Plasmid pKTVIH5 Neo is constructed by linearizing pKTVIH5 with Cla I; mixing with a 1.8 kb Cla I fragment containing the bacterial lac UV5 promoter, SV40 early promoter, and Tn5 Neo$^r$ marker obtained from pAFVXM, ligating, transforming bacteria and selecting for kanamycin resistance. Clones with the insert in the indicated orientation are identified by restriction analysis (FIG. 12).

F. Construction of MHMTK Neo Retroviral Vector

Figure 14:
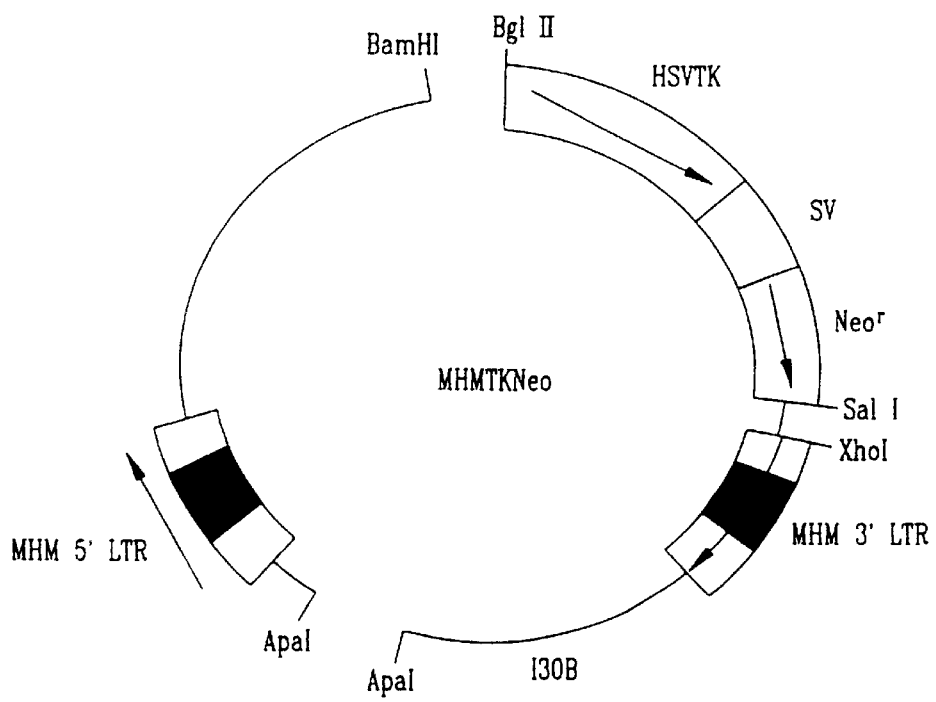
FIG. 14 is a schematic illustration of pMHMTKNeo.

The retroviral vector MHMTK Neo is constructed essentially as described below (see FIG. 14).

Figure 13:
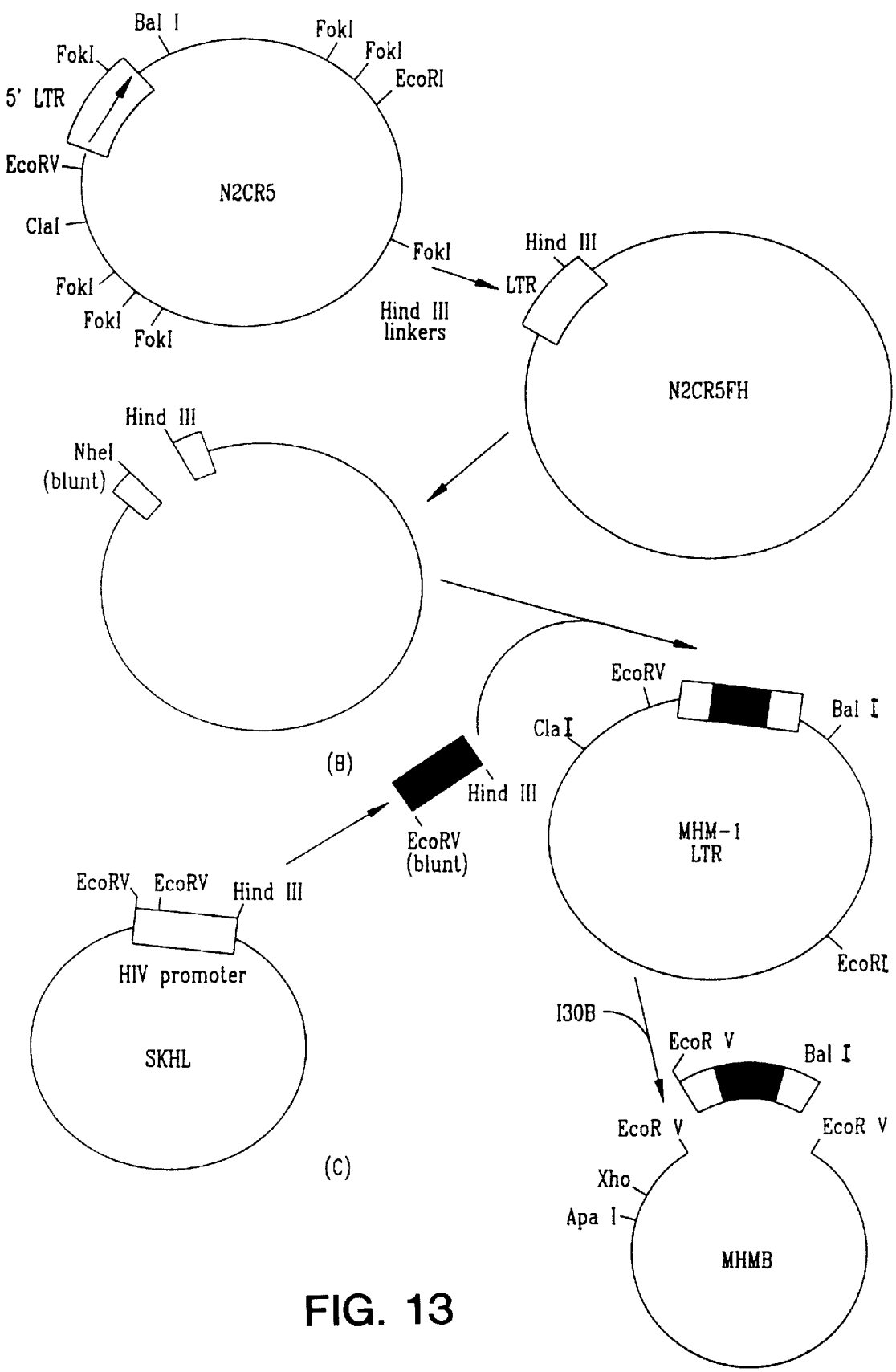
FIG. 13 is a schematic illustration of the construction of pMHM−1 LTR and pMHMB.

1. Construction of intermediate plasmid MHM-1 LTR.
  a) Plasmid pN2CR5 from Example 1A is linearized by partial digestion with Fok I, the 5' overhang filled in with deoxynucleotide triphosphates using Klenow DNA polymerase, and Hind III linkers inserted. After transformation into bacteria, a clone with a Hind III linker inserted in the MLV LTR Fok I site is identified by restriction enzyme analysis. This plasmid is designated pN2CR5FH.
  b) Plasmid pN2CR5FH is linearized with Nhe I, the 5' overhang filled in with Klenow polymerase digested with Hind III, and the 4.3 kb fragment with promoterless LTR sequences isolated.
  c) 0.5 kb Eco RV/Hind III HIV promoter sequences are isolated from pSKHL from Example 1B.
  d) b and c are mixed, ligated, used to transform bacteria, and the structure of MHM-1 is confirmed by restriction enzyme analysis (see FIG. 13).
2. The 0.7 kb Eco RV/Bal I fragment isolated from MHM-1 is repaired and subcloned into the Eco RV site of plasmid I30B. I30B is a modified IBI30 plasmid containing additional Bgl II, Bst II, Nco I and Nde I sites in the polylinker). After transformation into bacteria, clones with the desired orientation are identified by restriction enzyme analysis. This construct is designated pMHMB.
3. Plasmid pMHMB is digested with Apa I and Xho I and the 0.8 Kb fragment (to be used as the 3' LTR) was gel purified.
4. MHM-1 LTR is digested with Apa I/Bam HI and the 1.8 kb MHM-1 LTR (FIG. 13) packaging sequence gel purified.
5. The 2.8 kb Bgl II/Sal I fragment containing the HSVTK coding region upstream of the SV40 early promoter driving Neo$^r$ obtained from pTK-3 (see FIG. 9).
6. 3–5 are mixed, ligated, used to transform bacteria, and desired clones are identified by restriction enzyme analysis.

This vector and similar vectors which contain inducible elements in their LTR's result in an added safety feature. Briefly, since the LTR is inactive in the absence of HIV, insertional downstream activation of undesirable host genes (such as proto-oncogenes) does not occur. However, tat expression in the packaging cell line allows facile manipulation of the virion in tissue culture.

G. Construction of RRKTVIH Retroviral Vector

Figure 15:
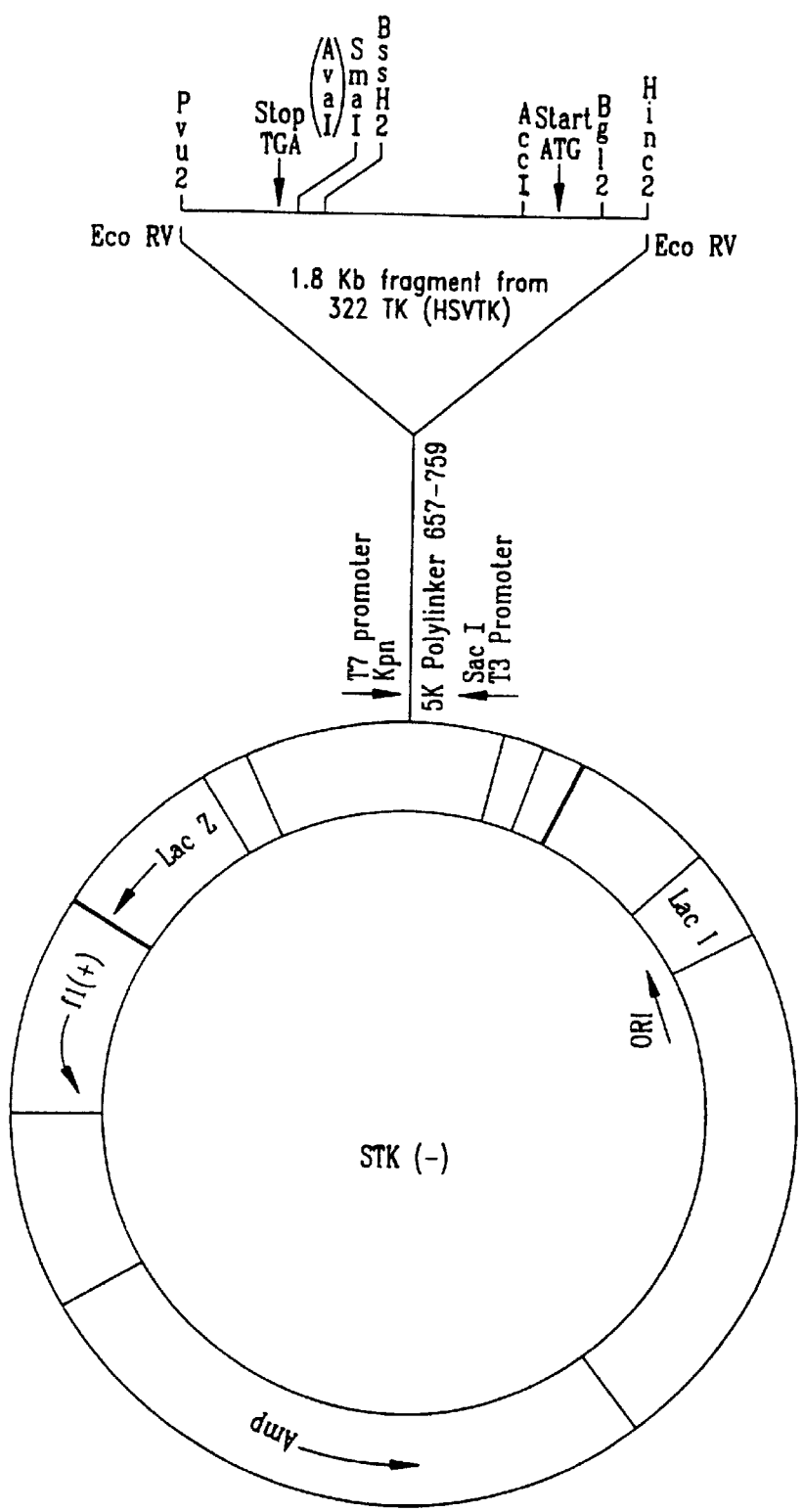
FIG. 15 is a schematic illustration of pSTK(−).
Figure 16:
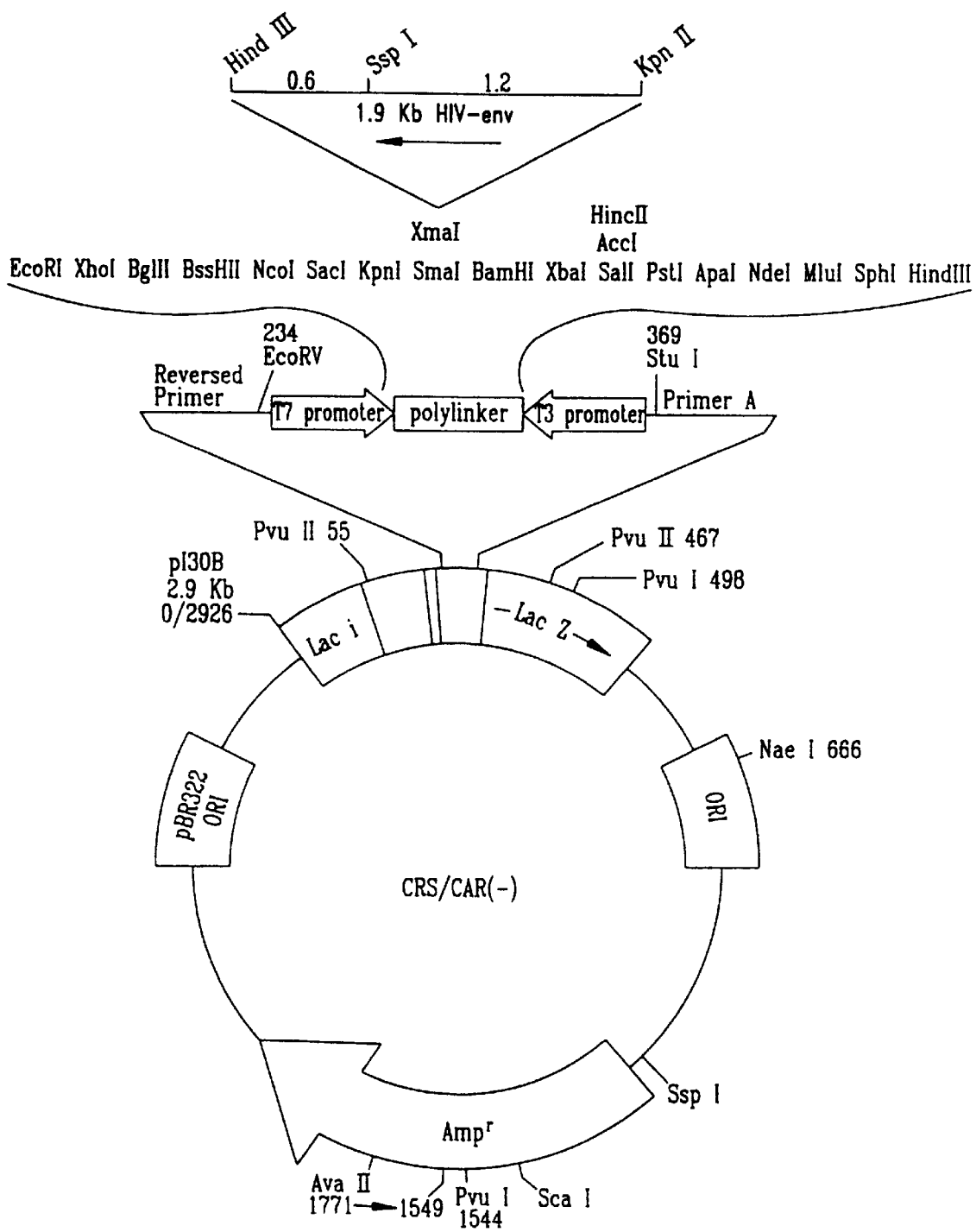
FIG. 16 is a schematic illustration of pCRS/CAR(−).

The retroviral vector RRKTVIH is constructed essentially as described below (see FIG. 17).
1. The 9.2 kb Asu II/Xho I fragment is isolated from N2 vector DNA (Keller et al., Nature 318:145, 1985).
2. The 0.6 kb Xho I/Eco RI HIV promoter fragment is isolated from plasmid pSKHL from Example 1B.
3. The HIV rev responsive HSVTK (RRTK) is constructed in the following manner:
  a) The HSVTK gene is subcloned as a 1.8 kb Hinc II/Pvu II fragment into the Eco RV site of vector SK$^+$. This construct is designated pSTK(-). (FIG. 15.)
  b) The 1.8 kb Kpn I/Hind III fragment which contains the CRS/CAR elements from HIV IIIB env is repaired and blunt-end ligated into the Sma I site of vector I30B. This construct is designated pCRS/CAR(-). I30B is a modified IBI30 plasmid containing the same additional restriction sites as for pUC31 with an Nde I site instead of the IBI30 Xho I site.
  c) The 3.6 kb BssH II/Eco RI fragment containing vector and HSVTK polyadenylation signals is isolated from pSTK-,
  d) The 1.8 kb Bam HI/BssH II CRS/CAR fragment is isolated from pCRS/CAR- (FIG. 16).
  e) The 1.2 Eco RI/Bam HI coding sequence fragment is isolated from pTKΔA (FIG. 7).
  f) c, d and e are ligated and desired recombinant vector constructs are screened by restriction enzyme analysis.
4. Rev-responsive HSVTK is isolated as a 3.6 kb Eco RI/Cla I fragment.
5. 1, 2 and 4 are ligated and appropriate recombinants identified by restriction enzyme analysis.

H. Construction of Tat and Anti-tat Expression Vectors.

Figure 18:
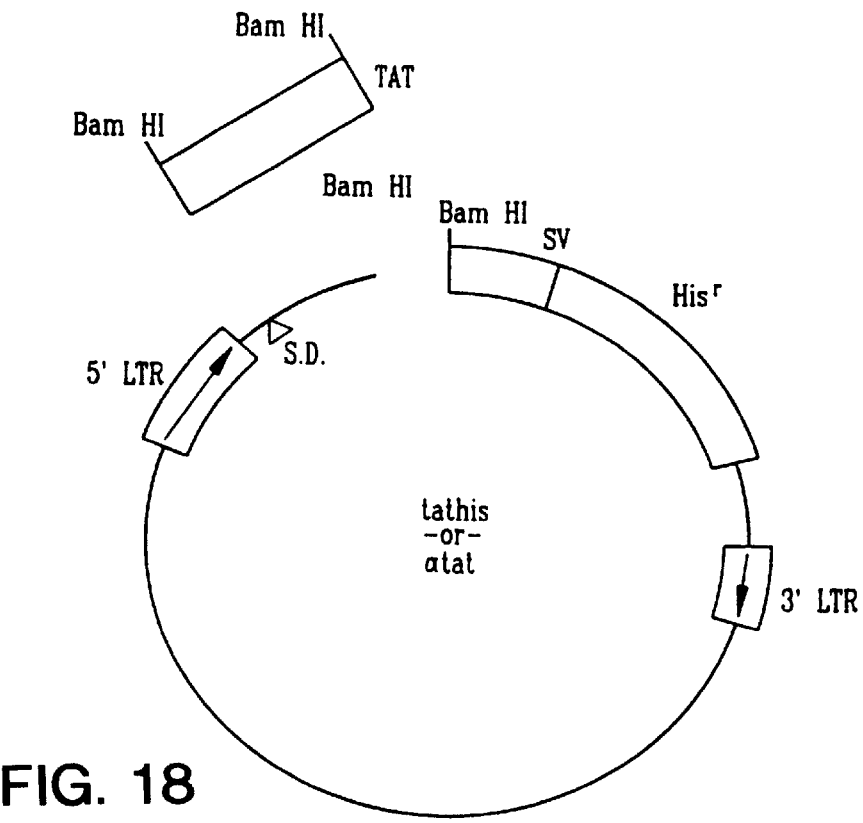
FIG. 18 is a schematic illustration of tathis and anti-tat.

The expression vector tat and anti-tat are constructed essentially as described below (see FIG. 18). These vectors are used as pseudo-HIV to test-activate tat-dependent HSVTK vectors.
1. The His$^r$ expression vector pBamHis is linearized with Bam HI and treated with calf intestinal alkaline phosphatase.
2. The Sac I site of pCV-1 (Arya et al., Science 229:69–73, 1985) is mutagenized to a Bam HI site and the 350 bp Bam HI coding sequence of HIV tat is isolated.
3. The fragments purified in steps 1 and 2 are mixed, ligated, used to transform bacteria, and clones with tat in both orientations (expressing tat or the "anti-sense" tat) are identified by restriction enzyme analysis.

These constructs are used to generate infectious recombinant vector particles in conjunction with a packaging cell line such as PA317 (ATCC No. 9078) essentially as follows. Briefly, 10 μg of plasmid provector is transfected by calcium phosphate precipitation onto ψ2 cells, and the supernatents used to infect PA317 cells. These vectors are genetically stable and result in predictable proviral structure as judged by Southern blot analysis of restriction-enzyme-digested genomic DNA from individual clones of infected cells (39/40 clones tested had proviruses of the expected size).

Example 2

Packing of the Vector Constructs

Figure 21:
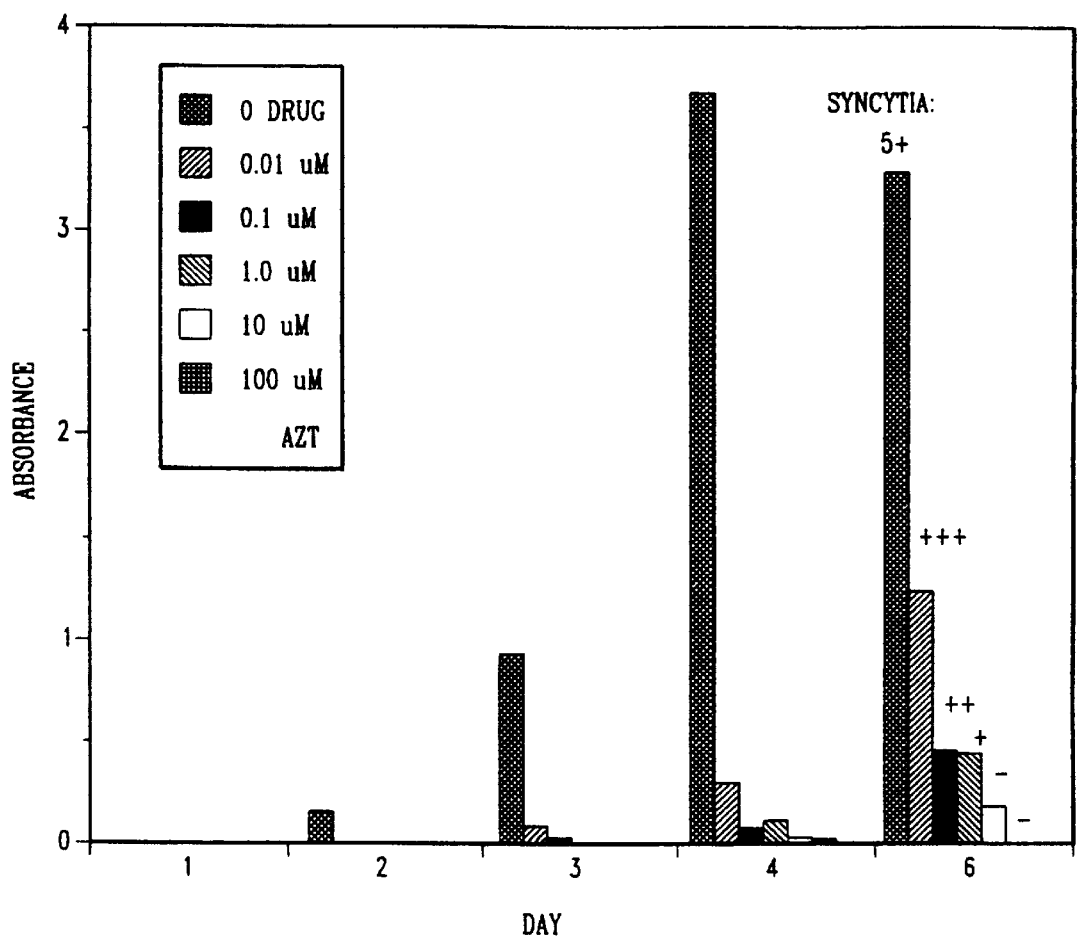
FIG. 21 is a bar graph which illustrates the effect of AZT on HIV infection.

The biological properties of these retroviral vectors are described hereinafter. The HIV tat gene ("tathis" vector— see FIG. 18) is transfected into mouse PA317 cells. Five individual histidinol-resistant subclones are obtained, designated TH 1–5 which express HIV tat. These cells are thus an experimental approximation of HIV infected cells. The vectors KTVIHAX (from Example 1D), KTVIH5Neo (from Example 1E), and MHMTKNeo (from Example 1F), are subsequently introduced by infection into these tat-expressing cell lines as well as their parent cell line lacking tat. Cell viability is then determined in various concentrations of the HSVTK-specific cytotoxic drug, acyclovir (ACV). The data are reported here as LD50 (the drug concentration at which 50% toxicity is observed) interpolated from graphs of viable cells vs ACV concentration. The parental cell line containing the HSVTK vectors but lacking tat (non-HIV-infected model) showed no detectable toxicity by ACV at the concentrations tested. These cells thus require 100 μM ACV or greater for cytotoxicity. This is true also for these cells lacking the vectors. Thus the vectors alone, ACV alone, or even the vector +ACV is not cytotoxic. However, cell lines which express HIV tat (the experimental representation of an HIV infection) are effectively killed by ACV (FIG. 21). This is true to varying degrees for all three vectors tested. These data indicate that HIV-infected cells will be killed in the presence of ACV and "potentiator" vectors.

In an analogous experiment, vectors KTVIHAX and KTVIH5 Neo are introduced by infection into human T-cell and monocyte cell lines Sup T1 (Science 234:1123), H9, HL60(ATCC No. CCL240), H9 (ATCC No. HTB176), and U937 (ATCC No. CRL1593) cells. Subsequently, these cells are infected with tathis or anti-tat vectors, selected in histidinol, and cell viability determined at various concentrations of the ACV analog, Fluoro-iodo-arabinoside-uridine (FIAU). The $LD_{50}$ reported in Table 1 (below) indicate that a vector dependent increase in FIAU toxicity occurs in the absence of HIV tat but is increased an additional ten- to twentyfold when tat is present. This indicates that although there is a baseline HSVTK expression in all but HL60 cells, expression is even greater in the presence of HIV tat. Addition of the HSVTK vectors alone had no detectable increase in ACV toxicity in HL60 cells in the absence of HIV tat.

TABLE 1

HIV tat inducibility of FIAU cytotoxicity in human monocyte and T-cell lines infected with conditionally lethal recombinant retroviral vectors

| Cell Type | Vectors | tat | LD5OFIAU(1M) |
|---|---|---|---|
| HL60 | — | − | 50 |
| ("monocyte") | — | + | 50 |
| | KTVIHAX | − | 50 |
| | KTVIHAX | + | <0.2 |
| | KTVIH5Neo | − | 50 |
| | KTVIH5Neo | + | <0.2 |
| U937 | — | − | 10 |
| ("monocyte") | KTVIHAX | − | 0.5 |
| | KTVIHAX | + | 0.05 |
| | KTVIH5Neo | − | 0.5 |
| | KTVIH5Neo | + | 0.05 |
| Sup T1 | — | − | 10 |
| ("T-cell") | — | + | 5 |
| | KTVIHAX | − | 0.5 |
| | KTVIHAX | + | 0.05 |
| | KTVIH5Neo | − | 0.5 |
| | KTVIH5Neo | + | 0.05 |
| H9 | — | − | 10 |
| ("T-cell") | KTVIHAX | − | 2 |
| | KTVIHAX | + | 0.2 |
| | KTVIH5Neo | − | 1 |
| | KTVIH5Neo | + | 0.05 |

Similarly, HIV infection of human T-cell line H9 containing HSVTK vector KTVIHAX +/− FIAU show a fivefold preferential inhibition of infection (through cell killing) in the presence of FIAU. Cultures are first treated with vector, then challenged with HIV for 4 days with or without FIAU. Viral supernatants are then titered using the soluble alkaline phosphatase assay described below.

Soluble Alkaline Phosphatase Assay

Medium was removed from infected cells, microfuged for 10 seconds, and then heated to 68° C. for 10 minutes to destroy endogenous phosphatases. The medium was then microfuged for 2 minutes and an aliquot (10–50 µl) removed for assay. 100 µl of buffer (1 M diethanolamine, pH 9.8; 0.5 Mm $MgCl_2$; 10 mM L-homoarginine) was added and then 20 µl of 120 mM p-nitrophenylphosphate (in buffers) was added. The $A_{405}$ of the reaction mixture was monitored using an automatic plate reader.

Figure 20:
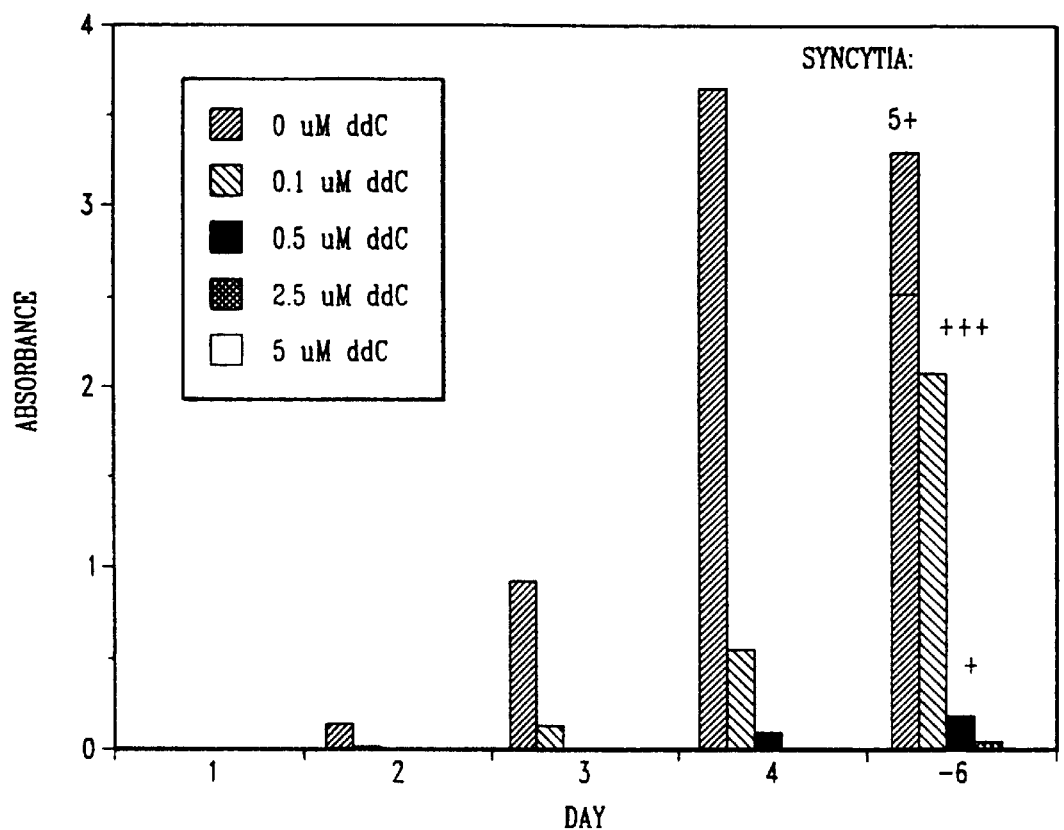
FIG. 20 is a bar graph which illustrates the effect of ddC on HIV infection.

FIGS. 20 and 21 depict typical results of a time course of HIV infection of Sup T1 cells using the alkaline phosphatase assay in the presence of varying concentrations of antiviral drugs. The "+" and "−" on day 6 indicate the presence or absence of syncytia respectively.

Example 3

Construction of pBH-1 and pMγ-IFN/TK Vectors pRRTK from Example 1G is digested with Xho I and Bam HI in order to obtain a 1.2 Kb fragment containing the HSVTK gene. This fragment is ligated into pSP72 (Promega Corp., Madison, Wis.) at the Xho I and Bam HI restriction sites found in the polylinker. This plasmid is designated pRRTK-B. pRRTK-B is digested with Xho I and Cla I to obtain a 1.2 Kb fragment containing the HSVTK gene. This fragment is then ligated into KT-3 (the construction of this vector is described in WO 91/02805) after digestion with Xho I and Cla I site removal of the Kb HIV gag/prot fragment by gel purification. This plasmid is designated pBH-1.

Example 4

Construction of DA/TK-3, DA/BH-1. DA mγ-IFN/ TK, and HA hγ-IFN/TK Producer Cell Lines Ten micrograms of pTK-3 DNA (FIG. 9) and 10 µg of pMLP-G DNA (the construction of this vector is described in WO 92/14829) is cotransfected into 293 2-3 (a cell line derived from 293 cells ATCC No. CRL 1573, WO 92/05266) using a standard $CaPO_4$ method. Forty-eight hours after transfection, the supernatant is collected and filtered through a 0.45 µm syringe filter. This supernatant contains G-pseudotyped TK-3 vector which is used to infect freshly prepared DA (a cell line derived from D-17 ATCC No. CCL 183, WO 92/05266) cells. Twenty-four hours after adding the viral supernatant, the DA cells are placed under G-418 selection (800 µg/ml). After 7–9 days, a G-418 selected non-clonal pool is obtained and designated DA/TK-3. High titer clones can be identified by limited dilution cloning and screening individual isolates for the highest titer whose vector also expresses HSVTK This can be accomplished by determiniing Neo colony forming units by transducing a cell line which lacks cellular thymidine kinase such as 3T3TK⁻ or Hela TK⁻ and placing the cells in geneticin and HAT medium. The number of colonies growing under these conditions would reflect the number of transduced cells expressing Neo and HSVTK.

DA/BH-1 VCL was generated identically to DA/TK-3 with pBH-1 substituted for pTK-3. The generation of VCL for mγ-IFN/TK and hγ-IFN/TK is complicated by the fact that the vector does not contain a readily selectable drug resistance marker (such as Neo). The only known selection for HSVTK utilizes HAT medium with cells that lack endogenous TK (TK-). There are several ways by which VCLs for provectors such as mγ-IFN/TK and hγ-IFN/TK can be generated.

1. The PCL used to generate the VCL may be TK-. For instance, DA cells (TK+) could be grown in the presence of bromodeoxy uridine. This nucleotide analog is toxic specifically for cells that express TK and thus a rare mutant in the TK gene of DH would be selected for in culture. The frequency of this mutant could be increased by prior mutagenesis by physical means such as UV or γ irradiation or by chemical means such as exposure to chemical mutagen. Once the TK− variant of DA is generated, cells transduced with vectors such was mγ-IFN/TK or hγ-IFN/TK are selected for in HAT medium.

2. Selection in TK+ cells may be possible in some cell lines that contain relatively low levels of endogenous TK and may express the vector HSVTK at relatively high levels. This may be particularly true if HSVTK is expressed using a very active transcriptional promoter, e.g., the TK expressed from the LTR or CMV immediate early promoter. In this case, a modified HAT medium with below standard levels of thymidine may preferentially rescue transduced cells from the aininoperterin toxicity of HAT medium.

3. Selection for cells that express HSVTK may occur even in cells that express cellular TK ("dominant selection") since the substrate specificity of HSVTK is much broader than that of cellular TK. This difference can be exploited to select for HSVTK by using a selective medium similar to that used for the selection of Eco gpt (Stuhlmann et al., *PNAS* 81:7151, 1984). This selective medium utilized mycophenolic acid (Sigma Chem. Co., St. Louis, Mo.) to inhibit purine nucleotide biosynthesis resulting in cell death. If the cell expresses HSVITK, purine nucleosides such as xanthosine, may be phosphorylated by HSVTK to yield XMP, a precursor to both AMP and GMP. Thus, cells which express HSVTK may be selected in the same medium used for Eco gpt selection, with xanthosine substituted for xanthine.

4. VCLs may also be generated by selecting for the expression of vector genes other than the HSVTK gene. For example, VCLs containing vectors (KT1/TK) which express membrane bound proteins such may be sorted by fluorescence activated cell sorting. Alternatively, hγ-IFN/TK transduced VCLs may be sorted by the known increase of MHC class I and class II (as long as the PCL is human, since γ-IFN is highly species specific).

5. Further, clonal VCLs may be generated and identified in the absence of selection. This approach utilized the VSVG pseudotyped vector generated on 293 2-3 as described above, except that the DA cells will be transduced at high M.O.I. For example, 1 ml of vector generated by transient transfection (approximately $1 \times 10^5$ cfu/ml on 3T3TK–) is used to transduce $1 \times 10^4$ cells 1 time, 3 times, or 10 times to ensure that the majority of cells are transduced in at least 1 culture. The cells are then cloned by limiting dilution and individual isolates screened for high titer on 3T3TK– cells (or Hela TK– if xenotropic vector) in HAT medium.

Example 5

Determination of the effect of Ganciclovir on CT26 With or Without TK-3

Figure 22:
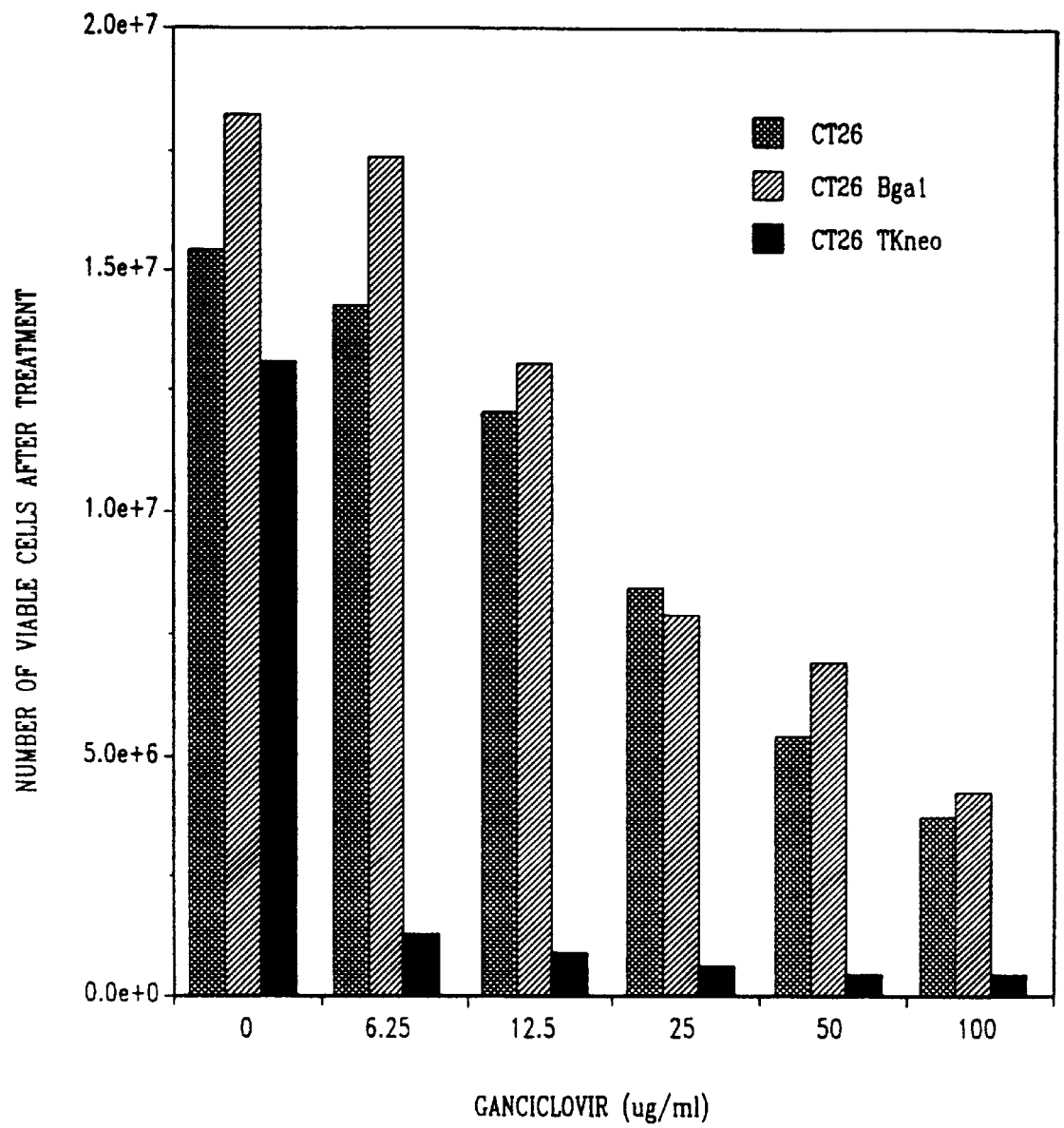
FIG. 22 is a bar graph which illustrates the effect of Ganciclovir on CT26, CT26 βgal and CT26TK Neo cells.

In order to determine whether or not ganciclovir had an effect on CT26 cells that were transduced with DA/TK-3 (CT26 TKneo), CT26 TKneo cells were seeded into six 10 cm² plates at a density of $2.5 \times 10^6$ per plate. As contrasts, each of two other cell types, CT26 and CT26 Bgal (this cell line was transduced with a virus carrying the reporter gene β-galactosidase from *E. coli*.), were also seeded into six 10 cm² plates as controls. Five plates of each cell type were treated twice per day for four consecutive days with medium containing ganciclovir concentrations of 100 ug/ml, 50 ug/ml, 25 ug/ml, 12.5 ug/ml and 6.25 ug/ml. One plate of each cell type was left untreated. Afterwards, the cells were removed from each dish using trypsinedta, resuspended in DMEM with 10% FBS and counted. The data in FIG. 22 shows that even the lowest dose of ganciclovir had a dramatic cytotoxic effect on the CT26 TKneo cells. This dose of ganciclovir (6.25 ug/ml) or even the next higher dose (12.5 ug/ml) did not have an effect on either the CT26 or CT26 Bgal cells. However, beginning at a ganciclovir dose of 25 ug/ml, a dose-dependent decrease in cell growth could be seen, although CT26 TK Neo cells were always more sensitive to the drug.

Example 6

Determination of a Ganciclovir Dose for the Treatment of Mice Injected With CT26 TK Neo Cells In order to test whether in vivo transduction of a murine tumor could be used to treat the disease, an experiment was performed to determine the optimal concentration of ganciclovir necessary to eliminate a tumor that was transduced and selected in vitro to assure 100% transduction. Colon tumor 26, CT26, (Brattain, Baylor College of Medicine, Houston, Tex.) cells are transduced with G-pseudotyped TK-3 vector. Twenty-four hours after adding the viral supernatant, the CT26 cells are placed under G-418 selection (450 Ag/ml). After 10 days incubation, a G-418 selected pool is obtained and designated CT26TK Neo. Twelve groups of 3 mice each are injected with $2 \times 10^5$ CT26TK Neo cells. Six groups of mice are injected with these cells intraperitoneally (I.P.) and six groups of mice are injected subcutaneously (S.C.). Two other groups of 3 mice each are injected with $2 \times 10^5$ unmodified CT26 cells (as a control) either I.P. or S.C.

Ten days after the injection of the CT26 or CT26TK Neo cells into these groups of mice, several concentrations of ganciclovir treatment are initiated. Each dose regimen consists of 2 daily AM and PM I.P. injections of ganciclovir. The experiment is summarized in Table A below.

TABLE A

| Group | Innoculum | Injection Route | Concentration of Ganciclovir (Mg/Kg) |
|---|---|---|---|
| 1 | CT26 | I.P. | 0 |
| 2 | CT26 TKneo | I.P. | 0 |
| 3 | CT26 TKneo | I.P. | 15.63 |
| 4 | CT26 TKneo | I.P. | 31.25 |
| 5 | CT26 TKneo | I.P. | 32.5 |
| 6 | CT26 TKneo | I.P. | 125.0 |
| 7 | CT26 TKneo | I.P. | 250.0 |
| 8 | CT26 TKneo | I.P. | 500.0 |
| 9 | CT26 | Subq. | 0 |
| 10 | CT26 TKneo | Subq. | 0 |
| 11 | CT26 TKneo | Subq. | 15.63 |
| 12 | CT26 TKneo | Subq. | 31.25 |
| 13 | CT26 TKneo | Subq. | 62.5 |
| 14 | CT26 TKneo | Subq. | 125.0 |
| 15 | CT26 TKneo | Subq. | 250.0 |
| 16 | CT26 TKneo | Subq. | 500.0 |

Figure 23:
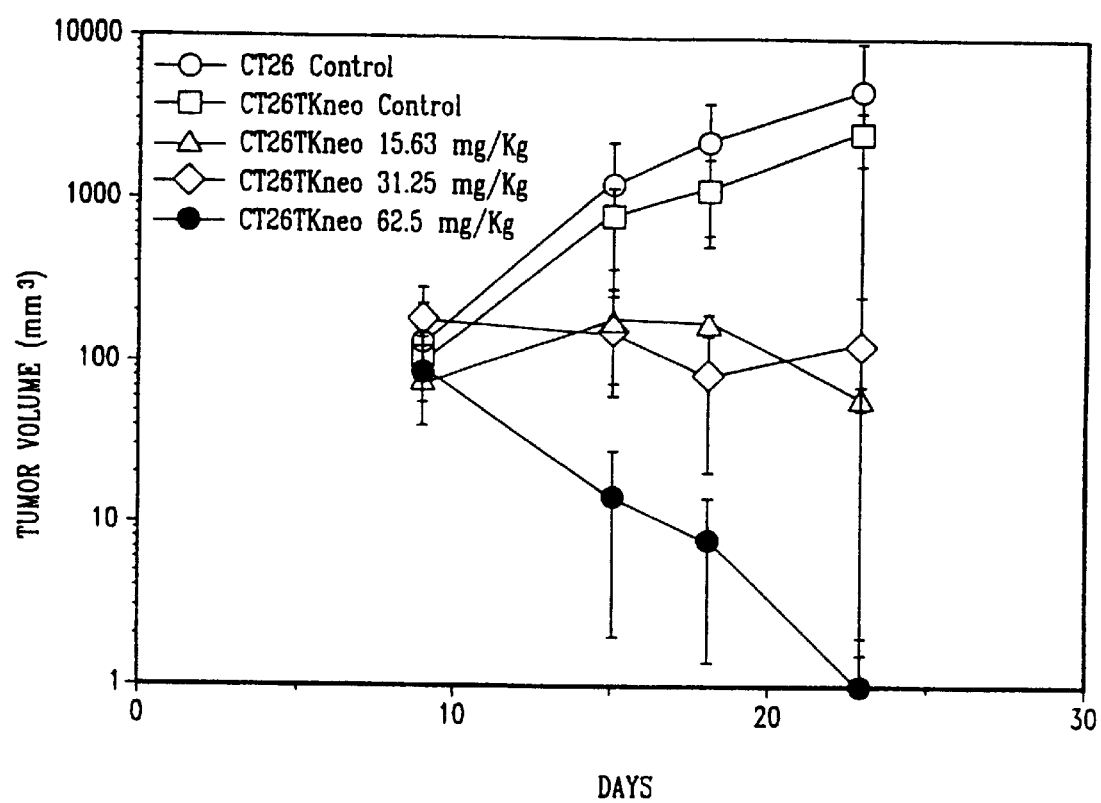
FIG. 23 is a graph which illustrates the effect of tumor volume over time in a Ganciclovir dose study of mice injected with CT26TK Neo.
Figure 24:
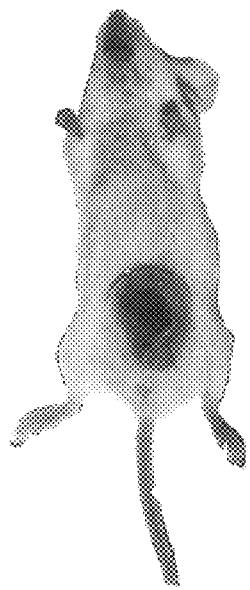
FIG. 24 is a series of four photographs of mice, illustrating the effect of different dose regimens of Ganciclovir on intraperitoneal tumor growth.
Figure 24:
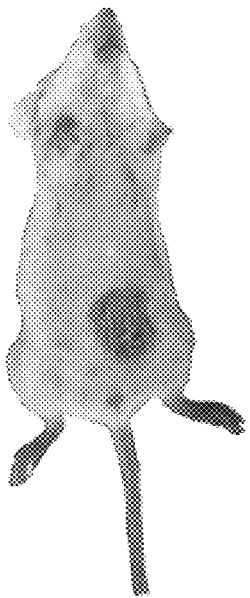
Figure 24:
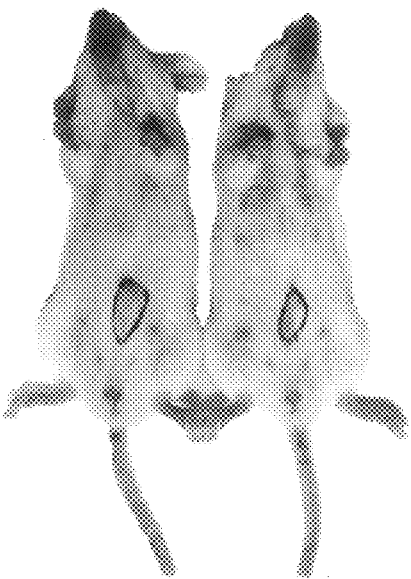
Figure 24:
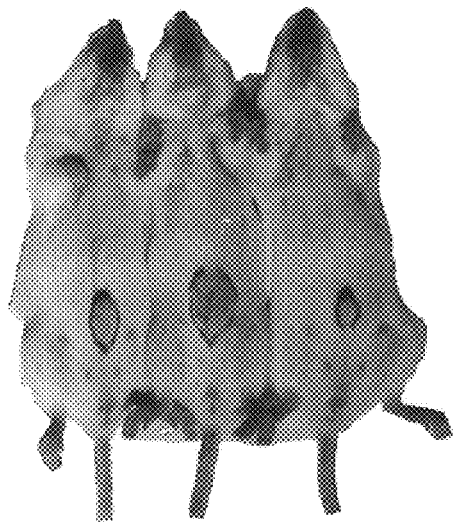
Figure 24:
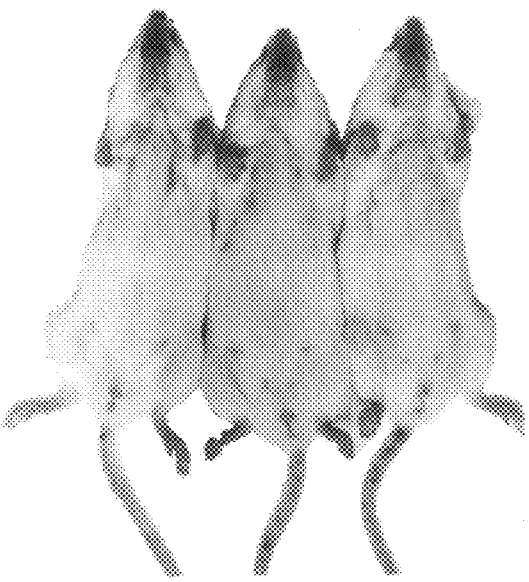
Figure 25:
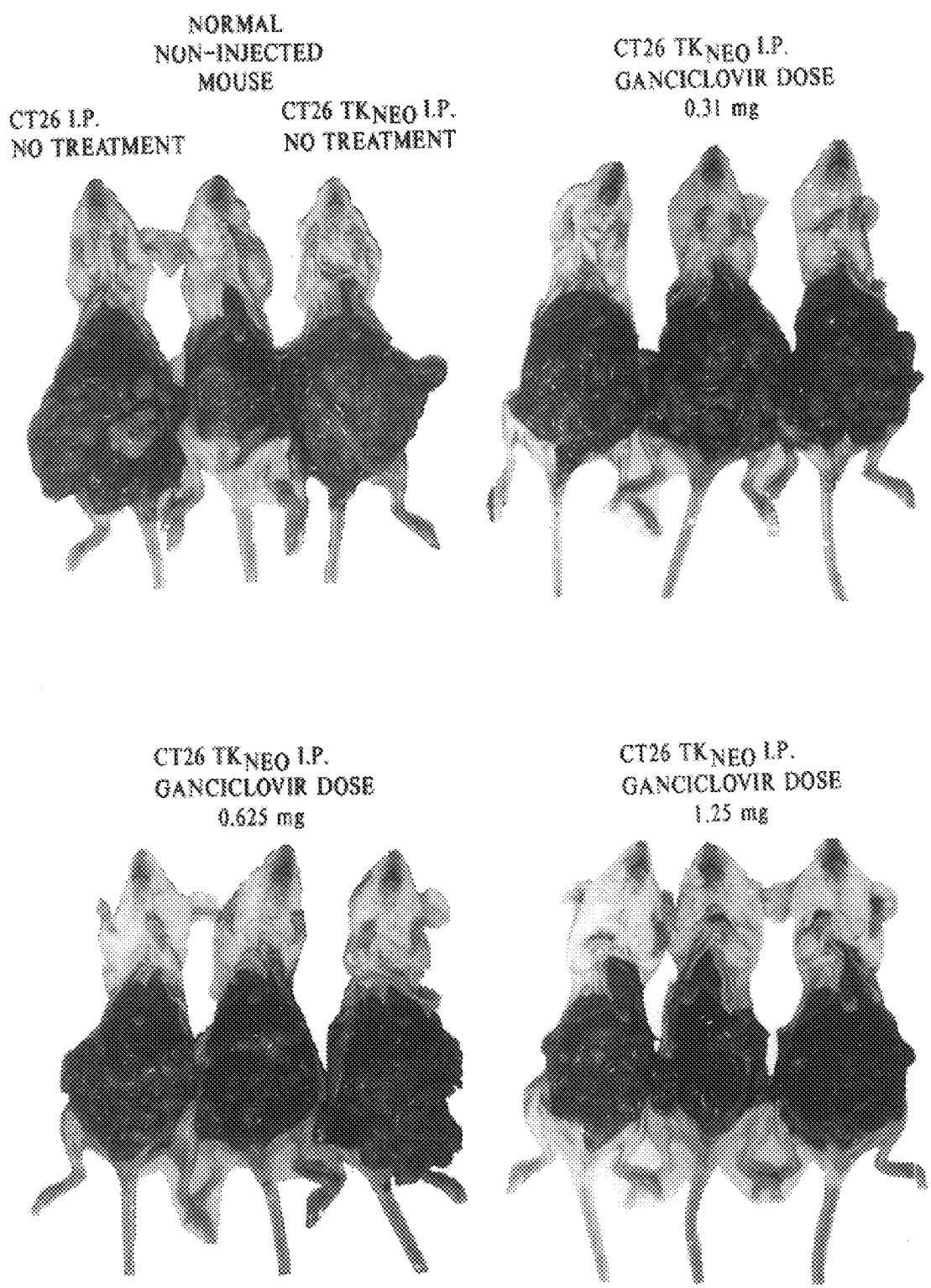
FIG. 25 is a series of four photographs of mice, illustrating the effect of different dose regimens of Ganciclovir on subcutaneous tumor growth.

After 5 days, all of the mice in the 125 mg/Kg, 250 mg/Kg and 500 mg/Kg treated groups were dead due to the toxic effects of ganciclovir. Mice in the 15.63 mg/Kg, 31.25 mg/Kg and 62.5 mg/Kg treated groups were treated for an additional 7 days and were able to tolerate the treatment. Tumor measurements were made for 23 days (FIG. 23). CT26TK Neo grew only slightly slower than unmodified CT26. Complete tumor regression was seen in the groups of mice treated with the 62.5 mg/Kg regimen. Partial tumor regression was seen in the 31.25 mg/Kg treated groups. Little or no effect was seen in the 15.63 mg/Kg treated groups as compared to the 2 untreated control groups. Even though there was some toxicity observed in the 62.5 mg/Kg groups, it was not life threatening and reversible upon the discontinuation of the treatments so this concentration was used for future studies (FIG. 23). After 24 days, the I.P. injected animals were sacrificed and evaluated. As seen in FIGS. 24 and 25 the optimal concentration for anti-tumor effect was similar whether the tumor was grown I.P. or S.C.

Example 7

Comparison of Cytotoxicity CT26 and CT26TK Neo In Vivo Tumor Growth

Figure 26:
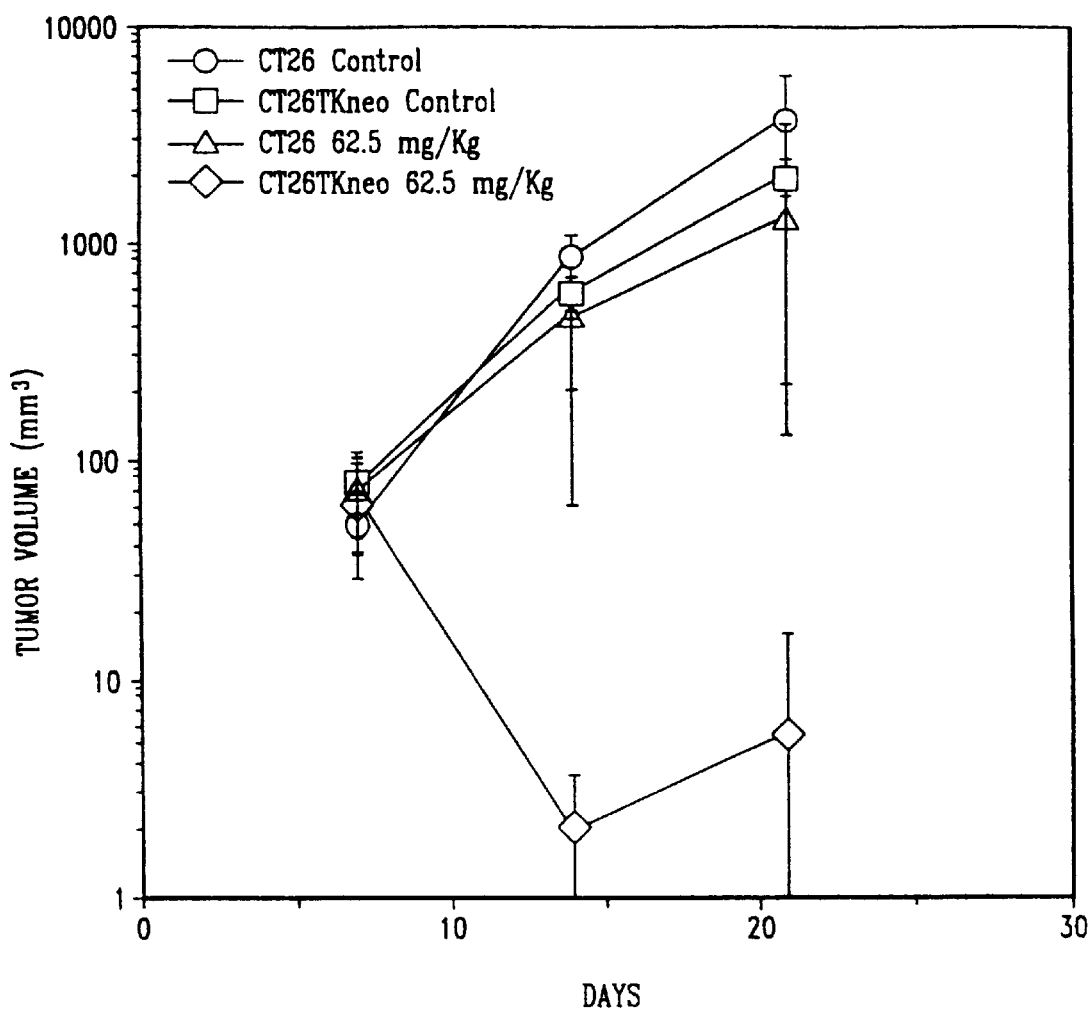
FIG. 26 is a graph illustrating the effect of Ganciclovir in CT26 versus CT26TK Neo cells.

In order to determine whether ganciclovir has an effect on the growth of unmodified CT126 tumor cells in vivo, 2 groups of 7 mice are injected S.C. with $2 \times 10^5$ unmodified CT26 cells and 2 groups of 7 mice are injected S.C. with $2 \times 10^5$ CT26TK Neo cells. Seven days after tumor implantation, one group of CT26 injected mice and one group of CT26TK Neo injected mice are placed on a twice daily (AM and PM) regimen of I.P. ganciclovir at 62.5 mg/Kg. These mice are treated for 12 days or until the CT26TK Neo injected animals have no detectable tumor burden. Tumor growth is monitored over a three week period. Mice injected with CT26 and treated with ganciclovir had tumors that were somewhat smaller than untreated mice injected with CT26, indicating a small HSVTK-independent inhibition of tumor growth (FIG. 26). However, a dramatic decrease in tumor burden was observed if, and only if, CT26 TKneo containing mice were treated with ganciclovir (FIG. 26).

Example 8

Injection of β-gal Direct Vector Into Mice Injected With CT26 Tumor Cells

To assess whether tumor cells could become transduced in vivo by the direct injection of vector, a reporter vector that expresses the *E. coli* β-galatosidase gene (CB (γ-gal)) was used. Five groups of two mice each are injected S.C. with $2\times10^5$ CT 26 tumor cells. Another group of two mice are S.C. injected with the $2\times10^5$ CT 26 β-gal-expressing cells as a control for γ-gal staining. The injection area on each mouse was circled with water-resistant marker. Two days after tumor cell inoculation, mice are injected with 0.2 ml of either PBS plus polybrene (4 μg/ml), CB β-gal ($5\times10^6$ colony forming units (CFU) ml) with and without polybrene, or DAhγ-IFN #15 with and without polybrene. Mice in each group are injected with their respective inoculant every two days within the area marked by water-resistant marker. Each group receives a total of four injections. Two days after the last injections, tumors from each of the groups of mice are removed, minced, and seeded into two 10 cm² plates containing DMEM plus 10% FBS and antibiotics. These tumor explants are allowed to grow in vitro for one week. After one week the cells are harvested, fixed with 2% formaldehyde and stained with X-gal overnight. The results of this experiment are presented below:

| Tumor Type and Treatment | Total Number of Cells | Number of Blue Cells | % Blue |
| --- | --- | --- | --- |
| 1. CT26 (PBS + polybrene) | $7.4 \times 10^6$ | $2.4 \times 10^5$ | 3.2% |
| 2. CT26 β-gal | $6.2 \times 10^6$ | $2.0 \times 10^6$ | 31.6% |
| 3. CT26 + β-gal vector w/o poly | $6.6 \times 10^6$ | $8.8 \times 10^5$ | 13.3% |
| 4. CT26 + β-gal vector w/poly | $6.4 \times 10^6$ | $1.3 \times 10^6$ | 20.0% |
| 5. CT26 + DA hγIFN #15 w/o poly | $6.9 \times 10^6$ | $2.0 \times 10^5$ | 2.9% |
| 6. CT26 + DA hγIFN #15 w/poly | $1.3 \times 10^6$ | $3.0 \times 10^4$ | 2.7% |

Due to the overnight staining, there was a substantial background staining of the unmodified CT26 or CT26 injected with hγ-IFN vector as a staining control (3%). Under these conditions, a maximum net of 17% of the cells stained (20 minus the 3% background). Given that the positive control (100% transduced) was only 28.6% stained itself, the 17% stain indicates that $(17/28.6)\times100$ or 60% of the cells were transduced in vivo. It is important to note that the tumor cells being transduced were in log phase and that the multiplicity of infection (M.O.I.) therefore decreased with tumor growth. These results from this experiment were used to design the next experiment.

Example 9

In Vivo Transduction of CT26 Tumor Cells by TK-3 Direct Vector

Figure 27:
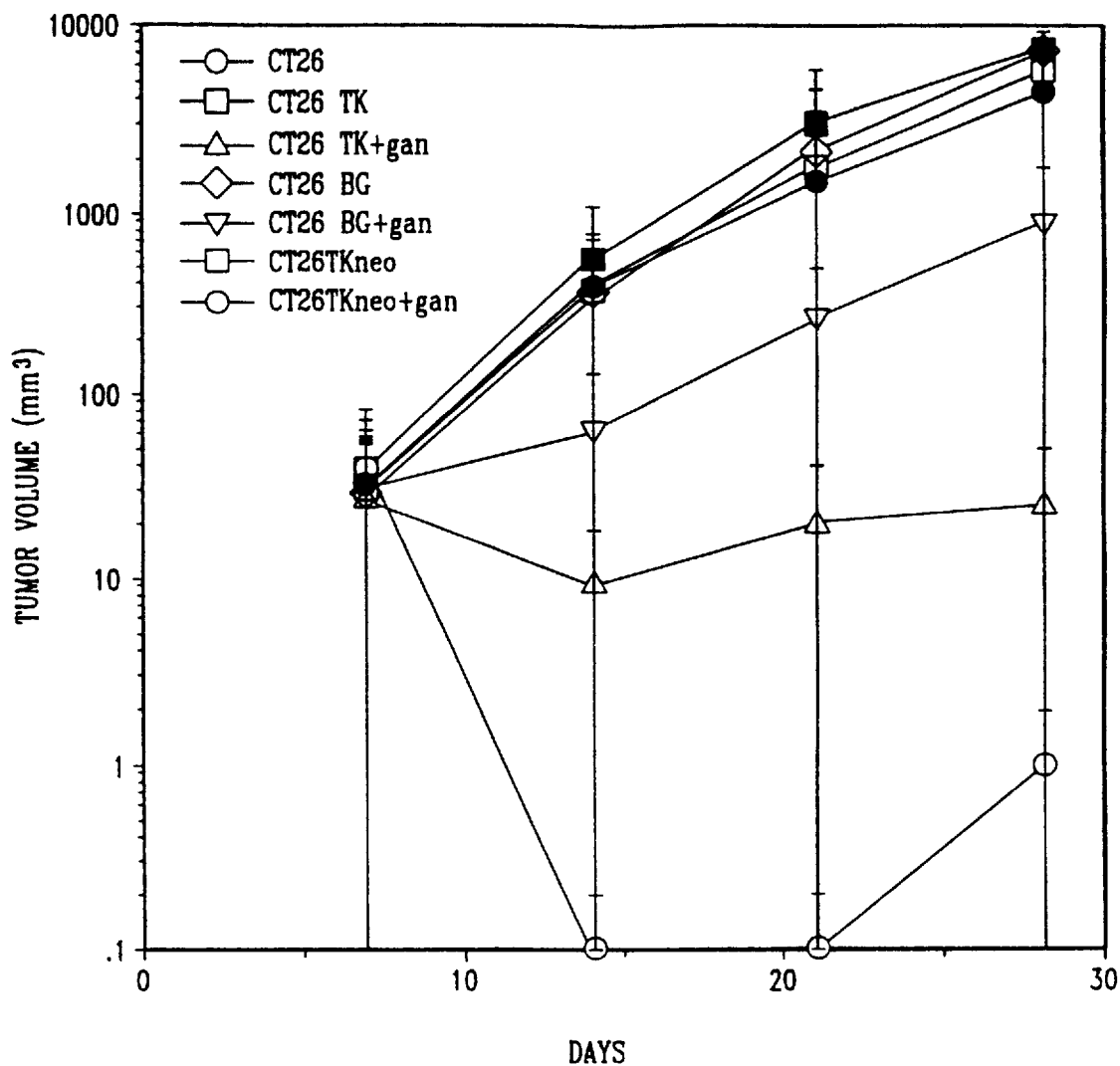
FIG. 27 is a graph illustrating the effect of Ganciclovir on in vivo transduced CT26 cells by injection of TK−3 virus containing the HSVTK gene.

This experiment is designed to demonstrate that TK-3 vector can deliver the HSVTK gene to a target cell in vivo and inhibit tumor growth in the presence of ganciclovir. Briefly, six groups of 10 mice are injected S.C. with $1\times10^5$ CT26 tumor cells. In addition, one group of 10 mice is injected S.C. with $1\times10^5$ CT26TK Neo cells as a control. The area of the S.C. injection is circled with a water-resistant marker. Twenty-four hours after tumor implantation, TK-3 or β-gal viral supernatants (0.2 ml) formulated with polybrene (4 μg/ml) are injected within the area marked by the water-resistant marker. Vector administration is continued for four consecutive days with one dose of the vector per day. Each vector dose contained $2\times10^5$ CFU/ml. Twenty-four hours after the last vector treatment, these mice are placed on a twice daily (AM and PM) injections of I.P. ganciclovir at 62.5 mg/Kg for 8 days. Finally, the mice receive a single dose of ganciclovir at 62.5 mg/Kg until the end of the experiment. Tumor growth was measured over a 4 week period (FIG. 27). The experiment is summarized in Table B below.

| Group | Innoculum | Retroviral Vector | Ganciclovir |
| --- | --- | --- | --- |
| 1 | CT26 | None | None |
| 2 | CT26 TKneo | None | None |
| 3 | CT26 TKneo | None | 62.5 Mg/Kg |
| 4 | CT26 | TK-3 | None |
| 5 | CT26 | TK-3 | 62.5 Mg/Kg |
| 6 | CT26 | CB Bgal | None |
| 7 | CT26 | CB Bgal | 62.5 Mg/Kg |

The data indicate that a substantial rate of growth of CT26 occured only when the animal was injected with both TK-3 and ganciclovir. The level of inhibition was not substantial as that observed for CT26 TKneo in vitro transduced and selected presumably in due to less than 100% in vivo transduction. Surprisingly, there was also a decrease in tumor growth when treated with the control vector, CB-β-gal and ganciclovir. This may indicate some inhibition of tumor growth due to the vector cell free supernatant itself, added with the previously observed small decrease caused by ganciclovir alone (FIG. 26). Regardless of that observation, the average tumor size is significantly smaller in the TK-3/ganciclovir treated animals than that of the CB-γ-gal/ganciclovir treated animals (7 fold and 10 fold and 75-fold smaller, at the 14 and 21 day time points, respectively). Thus, it appears that in vivo transduction by direct injection of HSVTK expressing retroviral vectors can result in inhibition of tumor growth in combination with ganciclovir administration.

In addition to delivering a gene of interest in vivo using direct injection of vector, mice can be treated by injecting the vector producer cell line from a PCL such as DA into or around the tumor (or both). Varying numbers of irradiated or unirradiated vector producer cells can be injected with and without a polycationic reagent to improve transduction efficiencies. Control mice would be injected with diluent D17 (Parent, non-PCL) transduced with TK-3 and a CB-γ-gal VCL. After sufficient time for in vivo transduction (approximately 2 weeks) ganciclovir injections would commence and efficacy would be determined by tumor measurements and/or overall survival.

Example 10

Construction of HSVTK Vector Containing Companion Genes Other Than a Resistance Marker The purpose for designing retroviral vectors with fail-safe capabilities containing a conditionally lethal gene such as HSVTK is to allow control of expression of the therapeutic gene after it has been administered to patients. Cells expressing the herpes simplex thymidine kinase gene become sensitive to ganciclovir, whereas normal cells are unaffected (Moolten et al., *Cancer Res.* 46:5276, 1986). The length of time the therapeutic gene is expressed can be limited or shut down in case the modified cells become harmful.

Expression of HSVTK by the vector also confers sensitivity (e.g. to ganciclovir upon the vector producing cell line). If VCLs are directly injected for in vivo transduction, they can then be destroyed by ganciclovir after their purpose is accomplished.

Figure 28:
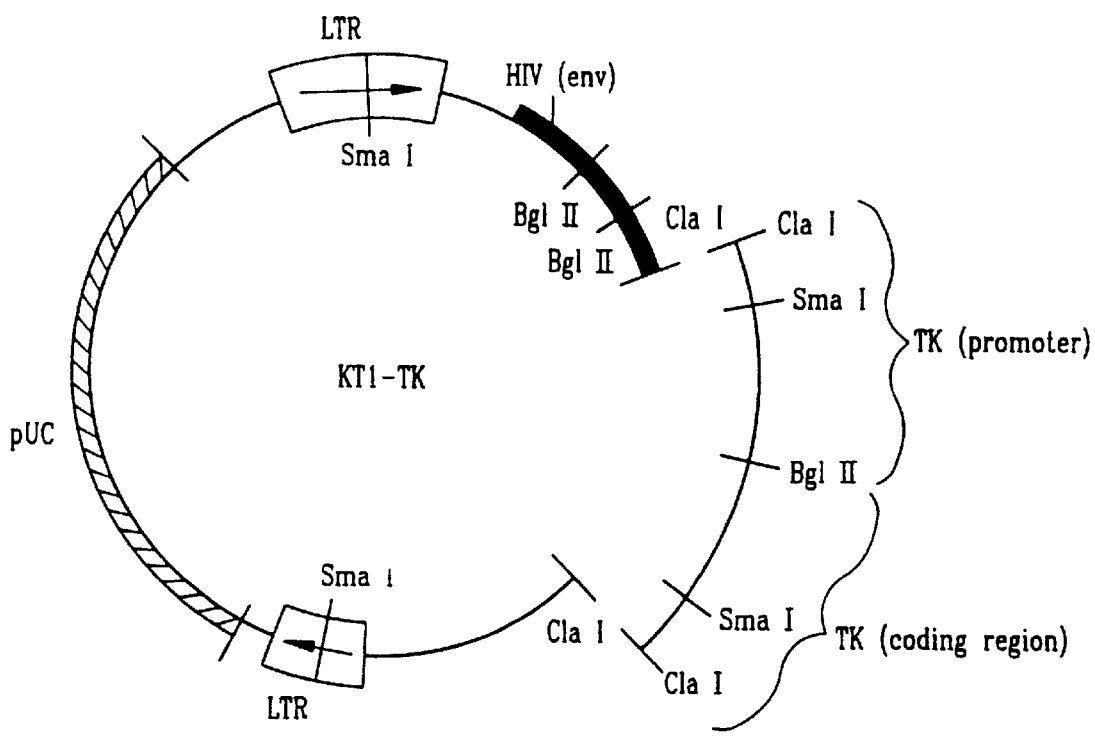
FIG. 28 is a schematic illustration of pKT1−TK.
Figure 19:
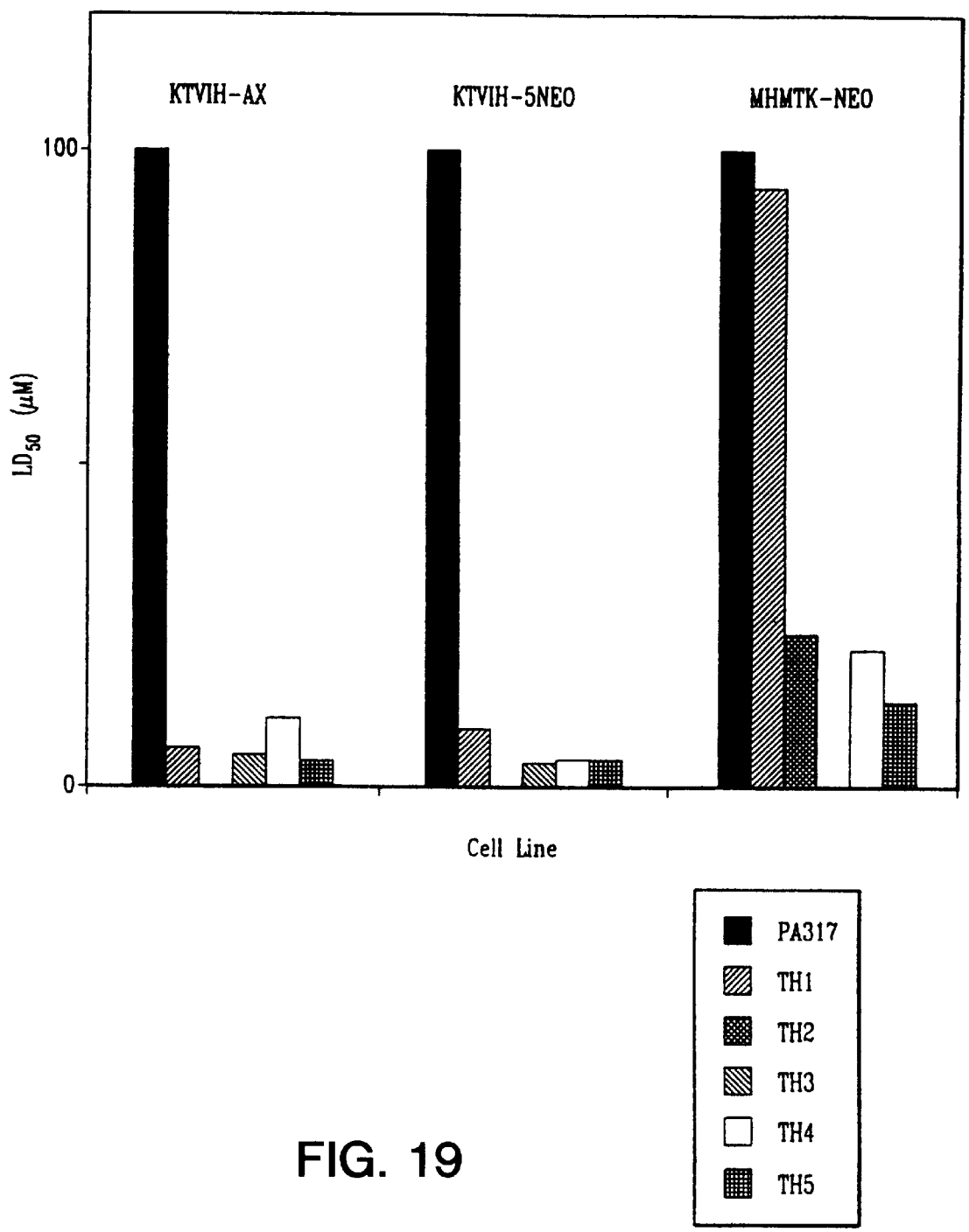
FIG. 19 is a bar graph which illustrates the effect of ACV toxicity in cells containing conditionally lethal vectors.

A. Construction of the Retroviral Provector pKT1-TK Expressing HIV III/Benv and HSVI Thymidine Kinase The retroviral provector pKT1-TK was constructed by first digesting TK-2 with Xho I, followed by Klenow treatment and dephosphorylation with calf intestine alkaline phosphatase. The treated linearized TK-2 was then ligated to phosphorylated Cla I linkers followed by transformation of bacteria. The correct individual clone was identified by restriction enzyme analysis and referred to as TK-2 (Cla I (FIG. 10)). A 2.0 kb Cla I fragment, containing both the TK promoter and TK coding sequences, was then isolated from TK-2 (Cla I). The KT1 retroviral vector (Recombinant Retroviruses Patent Application # 586,603) containing the HIV IIIB env was prepared by digesting with Cla I, followed by treatment with calf intestine alkaline phosphatase, and gel purified on a 1% agarose gel. The isolated 2.0 kb Cla I fragment from TK-2 was then ligated to the pretreated KT1 vector, transformed into bacteria, and correct individual clones identified by restriction enzyme analysis. The resulting retroviral vector was named KT1-TK (see FIG. 28). Of course, other promoters such as the CMV immediate early promoter could be used instead of the HSVTK promoter. A vector of this nature may be used to induce immune responses against HIV env while allowing the investigator to destroy transduced cells at any time by administration of ganciclovir.

Figure 29:
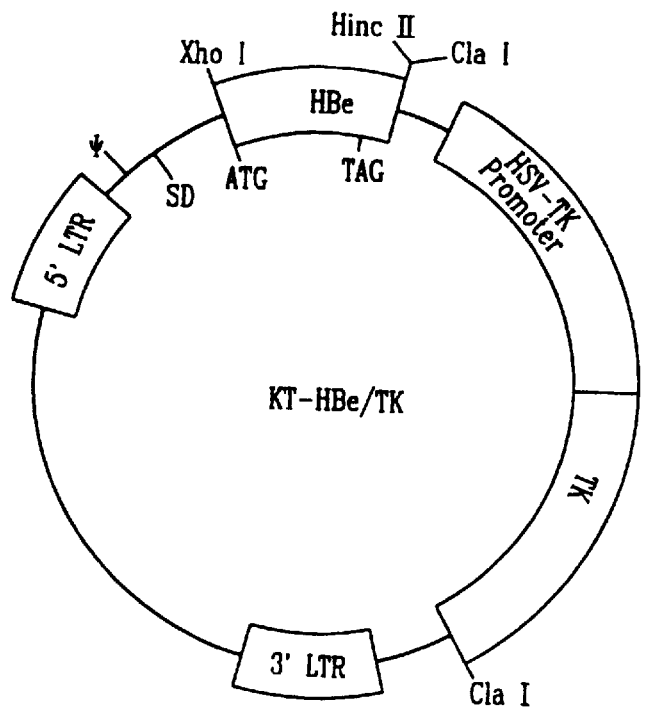
FIG. 29 is a schematic illustration of pKT1/Hbe/TK.

B. Construction of the Retroviral Provector, pKT-HBc/TK, Expressing the HBV Core Gene and HSV-1 Thymidine Kinase A retroviral provector pKT-HBc/TK was generated by cutting the pKT1-HBc "Neoless" provector DNA (see U.S. application Ser. No. 08/102,132, filed Aug. 4, 1993) with Cla I. This was then ligated with the 2.0 kb Cla I fragment from pTK-2 (Cla I), used to transform bacteria, and individual isolates were screened for the correct orientation. See FIG. 29.

C. Construction of the Retroviral Vector, phγTK and pmγTK, Expression of Human or Murine γ-IFN, Respectively, and the HSVTK Gene The retroviral provectors, pmγTK and phγTK, could be generated in the following steps.

1. pKT-1 is cut with Cla I. The linearized plasmid is then treated with calf intestinal phosphatase (CIP) to remove the phosphoryl moiety at the Cla I site. After extraction of the CIP by phenol:chloroform extraction, the plasmid is cut with Xho I. The resultant 5 kb fragment containing the pUC vector, 5' and 3' LTRs, and packaging sequence would be gel purified from the smaller HIVenv and SVNeo$^r$ fragments.

2. The coding sequences for murine or human γ-IFN are gel purified after cutting the plasmids pSP72mγ-IFN or pSP72hγ-IFN (see U.S. application Ser. No. 08/032,846, filed Mar. 17, 1993), respectively, with Cla I. The linearized plasmid is then treated with CIP to remove the phosphoryl moiety from the Cla I site. After extraction of the CIP by phenol:chloroform, the plasmid is cut with Xho I and the resultant 0.5 kb fragment purified by gel electrophoresis.

3. The HSVTK promoter and coding region will be isolated from Cla I cut pTK-2 (Cla I).

Figure 30:
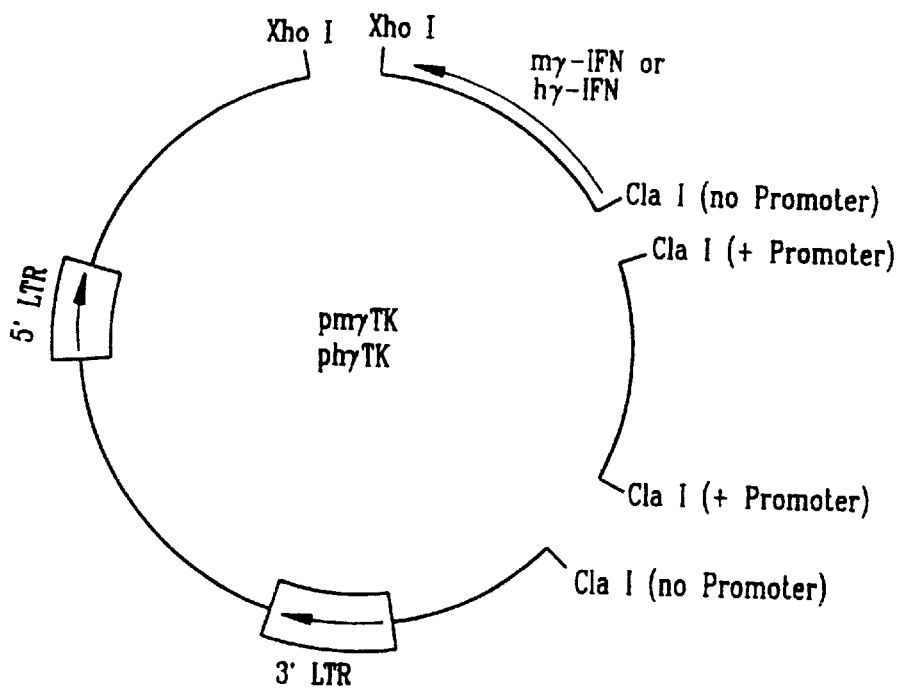
FIG. 30 is a schematic illustration of pmγTK and phγTK.

4. 1, 2 and 3 well mixed, ligated, used to transform bacteria, and plasmid is clonal transformants will be screened for the proper orientation of the HSVTK promoter/ gene. See FIG. 30.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An adenoviral vector that infects human cells, said adenoviral vector comprising a first and a second recombinant gene operably linked to a control sequence, said first recombinant gene being a conditionally lethal gene which encodes a conditionally lethal gene product, said conditionally lethal gene product converting a prodrug to a cytotoxic agent, said second recombinant gene encoding a human cytokine.

2. The vector of claim 1, wherein said prodrug is a purine-based or pyrimidine-based drug.

3. The vector of claim 2, wherein said conditionally lethal gene product is selected from the group consisting of a thymidine kinase, a cytosine deaminase, and *E. coli* guanine phosphoribosyl transferase.

4. The vector of claim 1, wherein said cytokine is selected from the group consisting of IL-1, IL-2, IL-3, IL-4, IL-5, IL-6, IL-7, IL-8, IL-9, IL-10, IL-11, IL-12, GM-CSF, and gamma-interferon.

5. The vector of claim 3, wherein said gene product is a thymidine kinase.

6. The vector of claim 5, wherein said thymidine kinase is a herpes simplex thymidine kinase.

7. The vector of claim 6, wherein said prodrug is selected from the group consisting of ganciclovir, acyclovir, FIAU, FIAC, DHPG, AZT and ddC.

8. The vector of claim 3, wherein said gene product is cytosine deaminase.

9. The vector of claim 8, wherein said prodrug is 5-fluorocytosine.

10. The vector of claim 3, wherein said gene product is *E. coli* guanine phosphoribosyl transferase.

11. The vector of claim 10, wherein said prodrug is thioxanthine.

12. The vector of claim 4, wherein said cytokine is gamma-interferon.

13. An adenoviral vector that infects human cells comprising a first and a second recombinant gene operably linked to a control sequence, said first recombinant gene comprising a gene encoding a thymidine kinase, said thymidine kinase activating a prodrug into a cytotoxic agent, said second recombinant gene encoding a human cytokine.

14. The vector of claim 13, wherein said prodrug is a purine-based or pyrimidine-based drug.

15. The vector of claim 13, wherein said thymidine kinase is herpes simplex thymidine kinase.

16. The vector of claim 13, wherein said cytokine is gamma-interferon.

17. A replication defective and recombinant adenoviral vector that infects human cells, said replication defective and recombinant adenoviral vector comprising a first and a second recombinant gene operably linked to a control sequence, said first recombinant gene encoding a thymidine kinase which activates a prodrug to a cytotoxic agent, said second recombinant gene encoding a human cytokine, said genes being expressed when said adenoviral vector infects a human cell.

18. The vector of claim 17, wherein said thymidine kinase is herpes simplex virus thymidine kinase.

19. The vector of claim 18, wherein said prodrug is selected from the group consisting of ganciclovir, acyclovir, FIAU, FIAC, DHPG, AZT and ddC.

20. The vector of claim 17, wherein said control sequence is a tissue or event specific promoter.

21. The vector of claim 17 wherein said cytokine is gamma interferon.

22. The vector of claim 4, wherein said cytokine is GM-CSF.

23. The vector of claim 4, wherein said cytokine is IL-2.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:1:

GAGAGATGGG GGAGGCTAAC TGAG                                    24

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (xi) SEQUENCE DESCRIPTION: SEQ ID NO:2:

GATCCTCAGT TAGCCTCCCC CATCTCTC                                             28

(2) INFORMATION FOR SEQ ID NO:3:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:3:

AGTGAATTCG AGCTCGGTAC CCGGGGATCC TCTAGAGTCG ACCTGCAGGC ATGCAAGCTT           60

GGCGTAATCA TGGTCAT                                                         77

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:4:

Thr Ile Met Thr
1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:5:

Thr Ile Met Met
1

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:6:

CCCGAGAGAT GGGGGAGGCT AACTGAG                                              27

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:7:

GGGCTCTCTA CCCCCTCCGA TTGACACCTA G                                         31

(2) INFORMATION FOR SEQ ID NO:8:

(i) SEQUENCE CHARACTERISTICS:
        (A) LENGTH: 8 amino acids
        (B) TYPE: amino acid

```
        (C) STRANDEDNESS:
        (D) TOPOLOGY: linear (xi) SEQUENCE DESCRIPTION: SEQ ID NO:8:

Ala Arg Glu Met Gly Glu Ala Asn
1               5
```